US008039686B2

(12) United States Patent
Podlich et al.

(10) Patent No.: US 8,039,686 B2
(45) Date of Patent: Oct. 18, 2011

(54) QTL "MAPPING AS-YOU-GO"

(75) Inventors: Dean Podlich, Des Moines, IA (US); Mark Cooper, Johnston, IA (US); Chris Winkler, Urbandale, IA (US)

(73) Assignee: Pioneer Hi-Bred International, Inc., Johnson, IA (US)

( * ) Notice: Subject to any disclaimer, the term of this patent is extended or adjusted under 35 U.S.C. 154(b) by 1658 days.

(21) Appl. No.: 10/874,813

(22) Filed: Jun. 22, 2004

(65) Prior Publication Data

US 2005/0015827 A1 Jan. 20, 2005

Related U.S. Application Data

(60) Provisional application No. 60/485,497, filed on Jul. 7, 2003.

(51) Int. Cl.
*A01H 1/00* (2006.01)
*A01H 1/02* (2006.01)
*A01H 1/04* (2006.01)
(52) U.S. Cl. ......... 800/267; 800/260; 800/266; 800/278
(58) Field of Classification Search .................. 800/266, 800/267, 260, 278
See application file for complete search history.

(56) References Cited

U.S. PATENT DOCUMENTS

| 5,437,697 A * | 8/1995 | Sebastian et al. ............ 800/266 |
| 6,368,806 B1 | 4/2002 | Openshaw et al. |
| 6,399,855 B1 | 6/2002 | Beavis |

FOREIGN PATENT DOCUMENTS

WO WO 01/49104 7/2001

OTHER PUBLICATIONS

Han et al. "Data Mining: Concepts and Techniques" Aug. 2000, Morgan Kaufmann Publishers, p. 418-420.
Stella et al. "Strategies for continual application of marker-assisted selection in an open nucleus population" Journal of Dairy Science, Sep. 2002, 85(9): 2358-2367.
Beavis (1998) QTL Analyses: Power, Precision and Accuracy, in *Molecular Analysis of Complex Traits*, AH Paterson (ed) pp. 145-161, CRC Press.
Bernardo, R. (2001) "What if we knew all the genes for a quantitative trait in hybrid crops?" *Crop Science*, 41:1-4.
Boer et al. (2002) "A penalized likelihood method for mapping epistatic quantitative trait Loci with one-dimensional genome searches," *Genetics*, 162: 951-960.
Chapman et al. (2002) "Linking Biophysical and Genetic Models to Integrate Physiology, Molecular Biology and Plant Breeding" In *Quantitative Genetics, Genomics and Plant Breeding*, M.S. Kang (ed.), 167-187.
Chapman et al. (2002) "Using crop simulation to generate genotype by environment interaction effects for sorghum in water-limited environments" *Australian Journal of Agricultural Researchi*, 53: 379-389.
Chapman et al. (2003) "Evaluationg Plant Breeding Strategies by Simulating Gene Action and Dryland Environment Effects" *Agronomy Journal*, 95: 99-113.
Clark (2000) "Limits to Prediction of Phenotypes from Knowledge of Genotypes" in *Evolutionary Biology*, vol. 32, Michael T. Clegg et al (eds.), 205-224.
Cooper et al. (1999) "Modelling plant breeding programs" *Trends in Agronomy*, 2:33-64.
Cooper et al. (2002) "Complexity, Quantitative Traits and Plant Breeding: a Role for Simulation Modelling in the Genetic Improvement of Crops" In *Quantitative Genetics, Genomics and Plant Breeding*, M.S. Kang (ed.), 143-166.
Cooper & Podlich (2002) "The E(*NK*) Model: Extending the *NK* Model to Incorporate Gene-by-Enviroment Interactions and Epistasis for Diploid Genomes" *Complexity*, 7(6): 31-47.
Cooper et al. (2002) "The GP Problem: Quantifying Gene-to-Phenotype Relationships" *In Silico Biology 2*, 151-164.
Crossa et al. (1999) "Interpreting genotype X environment interaction in tropical maize using linked molecular markers and environmental covariables" *Theor. Appl. Genet.*. 99:611-625.
Haley and Knott (1992) "A simple regression method for mapping quantitative trait loci in line crosses using flanking markers" *Heredity*, 69:315.
Hammer et al. (2002) "Future contributions of crop modeling—from heuristics and supporting decision making to understanding genetic regulation and aiding crop improvement" *European Journal of Agronomy*, 18: 15-31.
Harris et al. (2002) "A Model of Transcriptional Regulatory Networks Based on Biases in the Observed Regulation Rules" *Complexity*, 7(4): 23-40.
Holland, J.B., (2001) "Epistasis and Plant Breeding" in *Plant Breeding Reviews* Julies Janick (ed) 21:27-92.
Jannink & Jansen (2001) "Using complex plant pedigrees to map valuable genes," *Trends Plant Sci.*, 6:337-342.
Jannink et al. (2001) "Mapping epistatic quantitative trait loci with one-dimensional genome searches," *Genetics*, 157:445-454.
Jansen (1992) "A general mixture model for mapping quantitative trait loci by using molecular markers" *Theor. Appl. Genet.*, 85:252-260.
Jansen (1993) "Maximum likelihood in a generalized linear finite mixture model by using the EM algorithm." *Biometrics*, 49:227-231.
Jansen (1994) "Controlling the type I and type II errors in mapping quantitative trait loci" *Genetics* 138:871.
Jansen and Stam (1994) "High Resolution of quantitative trait into multiple loci via interval mapping." *Genetics*, 136:1447-1455.
Jansen (1994) "Mapping of quantitative trait loci by using genetic markers: an overview of biometrical models" in *Biometrics in Plant breeding: applications of molecular markers*, J.W. van Ooijen and J. Jansen (eds.), pp. 116-124.
Jansen (1996) "A general Monte Carlo method for mapping multiple quantitative trait loci." *Genetics*, 142:305-311.

(Continued)

*Primary Examiner* — David T Fox
*Assistant Examiner* — Keith Robinson
(74) *Attorney, Agent, or Firm* — Potter Anderson & Corroon LLP; Travis W. Bliss

(57) ABSTRACT

This invention provides methods for monitoring QTL effects and marker assisted selection (MAS) involving providing a recursively determined correlation between one or more markers and a phenotype of interest.

6 Claims, 24 Drawing Sheets

OTHER PUBLICATIONS

Jansen (1996) "Complex plant traits: time for polygenic analysis" *Trends in Plant Science*, 1(3): 89-94.

Jansen & Nap (2001) "Generical genomics: the added value from segregation" *Trends in Generics*, 17(7): 388-391.

Jansen et al. (2003) "Mapping Quantitative Trait Loci in Plant Breeding Populations: Use of Parental Haplotype Sharing" *Crop Sci.*, 43:829-834.

Jansen et al. (2003) "Studying complex biological systems using multifactorial perturbation." *Nat Rev Genet,*. 4(2):145-51.

Kuhnlein et al. (2003) "The dynamics of the genotype-phenotype association" *Poultry Science*, 82: 876-881.

Lande and Thompson (1990) "Efficiency of marker-assisted selection in the improvement of quantitative traits." *Genetics*, 124:743-756.

Lander and Botstein (1989) "Mapping mendelian factors underlying quantitative traits using RFLP linkage maps." *Genetics*, 121:185-199.

Mallepaard et al. (2001) "Bayesian versus frequentist analysis of multiple quantitative trait loci with an application to an outbred apple cross" *Theor. Appl. Genet*, 103:1243-1253.

Meuwissen and Goddard (2000) "Fine mapping of quantitative trait loci using linkage disequilibria with closely linked marker loci." *Genetics*, 155:421-430.

Nelson et al. (2001) "A combinatorial partitioning method to identify multilocus genotypic partitions that predict quantitative trait variation." *Genome Research*, 11:458-470.

Openshaw and Frascaroli (1997) "QTL Detection and Marker-Assisted Selection for Complex Traits in Maize" *52$^{nd}$ Annual corn and sorghum research conference*, pp. 44-53.

Peleman & Rouppe van der Voort (2003) "Breeding by design" *Trends Plant Sci.* 8:330-334.

Podlich & Cooper (1998) "QU-Gene: a simulation platform for quantitative analysis of genetic models" *Bionformatics*, 14(7): 632-653.

Podlich & Cooper (1999) "Modelling Plant Breeding Programs as Search Strategies on a Complex Response Surface" in *Seal '98. LNCS*, X. Yao et al. (eds.), 1585: 171-178.

Podlich et al. (1999) "Computer simulation of a selection strategy to accommodate genotype-environment interactions in a wheat recurrent selection programme" *Plant Breeding*, 118:17-28.

Podlich et al. (2004) "Mapping As You Go" *Crop Science*, 44:1560-1571.

Rebai and Goffinet (1993) "Power of tests for QTL detection using replicated progenies derived from a diallel cross" *Theor Appl Genet*, 86:1014.

Reymond et al. (2003) "Combining quantitative trait Loci analysis and an ecophysiological model to analyze the genetic variability of the responses of maize leaf growth to temperature and water deficit." *Plant Physiology*, 131: 664-675.

Soller et al. (1978) "The Efficiency of Experimental Designs for the Detection of Linkage between a Marker Locus and a Locus Affecting a Quantitative Trait in Segregating Populations" *Biometrics* 34:47.

Spelman et al. (1996) "Quantitative trait loci analysis for five milk production traits on chromosome six in the Dutch Holstein-Friesian population." *Genetics*, 144:1799.

van Eeuwijk et al. (2002) "Analysing QTL-Environment Interaction by Factorial Regression, with an Application to the CIMMYT Drought and Low-nitrogen Stress Programme in Maize" in Kang, M.S. (ed). *Quantitative Genetics, Genomics and Plant Breeding*, pp. 245-256. CAB International, Wallingford).

Van Ooijen (1992) "Accuracy of mapping quantitative trait loci in autogamous species" *Thor. Appl. Genet.*, 84:803-811.

Wang et al. (2001) "Power of the joint segregation analysis method for testing mixed major-gene and polygene inheritance models of quantitative traits" *Theor. Appl. Genet*, 103:804-816.

Wade (2002) "A gene's eye view of epistasis, selection and speciation" *J. Evol. Biology*, 15:337-346.

Yi and Xu (2001) "Bayesian mapping of quantitative trait loci under complicated mating designs" *Genetics*, 157:1759-1771.

Zeng (1994) "Precision mapping of quantitative trait loci." *Genetics*, 136:1457.

\* cited by examiner (a)

(b)

QTL "MAPPING AS-YOU-GO"

CROSS REFERENCE TO RELATED APPLICATIONS

This application claims priority to and benefit of U.S. Provisional Application No. 60/485,497, filed Jul. 7, 2003, the disclosure of which is incorporated herein for all purposes.

FIELD OF THE INVENTION

The present invention relates to the mapping of phenotypic traits, e.g., QTL in plants. More particularly the present invention provides a method for efficiently mapping and selecting plants for phenotypic traits which are subject to the effects of epistasis and gene x environment interaction.

BACKGROUND OF THE INVENTION

Over the last 60 to 70 years, the contribution of plant breeding to agricultural productivity has been spectacular (Smith (1998) 53$^{rd}$ Annual corn and sorghum research conference, American Seed Trade Association, Washington, D.C.; Duvick (1992) Maydica 37: 69). This has happened in large part because plant breeders have been adept at assimilating and integrating information from extensive evaluations of segregating progeny derived from multiple crosses of elite, inbred lines. Conducting such breeding programs requires extensive resources. A commercial maize breeder, for example, may evaluate 1,000 to 10,000 $F_3$ topcrossed progeny derived from 100 to 200 crosses in replicated field trials across wide geographic regions. Despite such significant investments of resources, there is evidence that the gains of the past will be difficult to sustain with current methods (Smith (1998), supra).

The primary motivation for developing molecular marker technologies from the point of view of plant breeders has been the possibility to increase breeding efficiency through marker assisted selection (MAS). The key components to the implementation of this approach are: (i) the creation of a dense genetic map of molecular markers, (ii) the detection of quantitative trait loci (QTL) based on statistical associations between marker and phenotypic variability, (iii) the definition of a set of desirable marker alleles based on the results of the QTL analysis, and (iv) the use and/or extrapolation of this information to the current set of breeding germplasm to enable marker-based selection decisions to be made. To date, this approach has been effective for relatively simple traits that are controlled by a small number of genes (e.g. disease resistance; Flint-Garcia et al., (2003) Theor. Appl. Genet. 107:1331-1336) but less effective for more complex traits that are controlled by many genes that are under the influence of epistasis (gene-by-gene interaction) and gene-by-environment interaction effects (Openshaw & Frascaroli (1997) Proc. Annu. Corn Sorghum Res. Conf. 52:44-53; Melchinger et al. (1998) Genetics 149:383-403; Utz et al. (2000) Genetics 154:1839-1849).

Conventional mapping approaches are typically predicated on the assumption that any QTL act in an additive manner, assuming that the effects of epistasis and genotype x environment interactions are negligible or nonexistent (for a recent review see, Bernardo, R. (2001) What if we knew all the genes for a quantitative trait in hybrid crops? Crop Science 41:1-4). In the absence of epistasis, there is no advantage to marker assisted selection for a quantitative trait (that is, knowing the effects of all genes contributing to the trait) over phenotypic selection. However, current understanding suggests that context dependent factors, such as epistasis, are important aspects of the genetic architecture of quantitative traits (See, e.g., Holland, J. B., Epistasis and Plant Breeding (2001) Plant Breeding Reviews 21:27-92).

A number of factors increase the difficulty of successfully employing a marker-based selection scheme for complex traits. One major problem has been the effective detection, estimation and utility of QTL and their effects. This is especially the case for traits governed by "context dependent" gene effects (i.e. interaction with other genes and/or environment).

Analysis methods have been developed in an attempt to address the effects of context dependency (e.g., Crossa et al. (1999) Theor. Appl. Genet. 99:611-625; Jannink & Jansen (2001) Trends Plant Sci. 6:337-342; Nelson et al. (2001) Genome Research 11:458-470; Boer et al. (2002) Genetics 162: 951-960; van Eeuwijk et al. (2002) In Kang, M. S. (ed). Quantitative Genetics, Genomics and Plant Breeding. pp. 245-256. CAB International, Wallingford). For example, in the case of epistasis, Holland (2001; Plant Breeding Reviews 21:27-92) outlined an approach that was based on the identification of preferred allele configurations across interacting genes. Similar approaches have been suggested by others (e.g., Jansen et al. (2003) Crop Sci. 43:829-834; Kuhnlein et al. (2003) Poultry Science 82: 876-881). Other advances in methodology include the use of multiple line crosses among related individuals (Jannink et al. (2001) Genetics 157:445-454; Yi and Xu (2001) Genetics 157:1759-1771; Bink et al. (2002) Theor. Appl. Genet 103:1243-1253) and/or haplotype information to increase the power to accurately estimate QTL and their effects (Meuwissen and Goddard (2000) Genetics 155:421-430; Jansen et al. (2003) Crop Sci. 43:829-834). In all cases, the analysis methods assume that the mapping studies can be conducted with sufficient power to adequately account for all, or at least the important, context dependencies that may exist.

Regardless of what assumptions are made, a common outcome of all QTL analysis methods is the estimation of QTL allele effects, whether at an individual gene level or across multiple interacting gene complexes (Jansen (1996) Trends in Plant Science 1:89-94). A target combination of marker alleles is defined from these estimates, forming the basis of selection in the application of MAS in a breeding program. More advanced applications of MAS may weight specific marker alleles based on the amount of genetic variation they explain in the analysis (Lande and Thompson (1990) Genetics 124:743-756).

However, in essence, the approach to MAS in plant breeding has been to develop accurate estimates of QTL effects within a relatively narrow reference population and use those estimates in the application of marker-based selection. This approach assumes that the desirable QTL alleles once identified will remain relevant over many cycles of selection. That is, the estimates of QTL effects that are calculated at the beginning will still apply as new germplasm is created during the breeding process (e.g., Peleman & Rouppe van der Voort (2003) Trends Plant Sci. 8:330-334). Additional QTL analyses may be conducted on new germplasm, but the purpose of such an approach is to validate or refine the initial estimates by making them 'more accurate'. The assumption that the value of QTL alleles should stay relatively fixed or static is appropriate for traits controlled solely by additive genes (e.g., Bernardo (2001) Crop Sci. 41:1-4). In this way, the effects of QTL are consistent across all or most germplasm (both current and future) and hence MAS can be implemented by independently assembling or 'stacking' desirable alleles. However, when context dependencies are present, the value of QTL alleles can differ depending on the genetic structure of the current set of germplasm in the breeding program (Wade (2002) *J. Evol. Biology* 15:337-346). That is, the value of a given QTL allele can change over cycles of selection due to changes in the background (i.e. context dependent) effects at any given time in the breeding process. Therefore, when these background effects are important, the stacking of desirable alleles by MAS becomes inadequate because it is possible that the initial target combination of alleles is no longer the best target, or even a relevant target, for increased trait performance in subsequent breeding cycles.

The methods of the present invention provide a novel approach, designated "Mapping As-You-Go" that are applicable, not only where the target genotype can be defined prior to selection, but also in situations in which it is not possible to define the target genotype at the commencement of the breeding program; the definition of the target genotype will be developed and refined with each cycle of selection in the breeding program. Thus, the definition of the target genotype can change with time as selection changes the genetic structure of the breeding population. These and other features will be apparent upon complete review of the following.

SUMMARY OF THE INVENTION

The present invention provides a novel approach to monitoring QTL effects in plant populations and performing marker assisted selection in the context of plant breeding programs. The methods of the invention, designated "Mapping As-You-Go," involve recursively reestimating and validating estimates of the effects of various alleles of a QTL throughout the breeding process ensuring that the estimates of QTL effects, i.e., QTL allele effects, remain relevant across germplasm throughout the course of the breeding program. These methods result in substantial increases in efficiency compared to conventional approaches, which evaluate QTL estimates at the initiation of the breeding program and use these same estimates for the duration of the breeding process, i.e., "Mapping Start Only" approaches, especially in situations where epistasis and/or genotype x environment interactions play a significant role in determining phenotype.

Accordingly, in a first embodiment, the present invention provides methods for ensuring the validity of the correspondence between at least one allele of a molecular marker and a phenotype. Typically the method involves monitoring a series of markers linked to putative QTL associated with a phenotype or trait of interest. The markers can span the genome of the plant species, or be selected to correspond to a particular chromosome, region or linkage group associated with the phenotype. The methods involve providing a recursively determined estimate of correlation between alleles of the marker (or markers) and a phenotype across a plurality of plant populations including the progeny of a number of bi-parental crosses. A first estimate of correlation between an allele of at least one marker and the phenotype, constituting a first estimate of QTL allele effects, is updated to provide a new or revised estimate of QTL allele effects by estimating a correlation between the allele of the marker and the phenotype in the progeny of a plant with the desired marker allele. For example, a first estimate of QTL allele effects is provided by estimating the correlation between the marker and a phenotype in a population of plants. The population of plants can include the progeny of a single breeding cross or a plurality of breeding crosses, and can be either actual plants or plant derived material, or in silico representations of the plants. At least one plant possessing the marker allele is selected from the population in which the correlation was established, or from a different population of plants. Optionally, in addition to marker selection, phenotypic information can be employed in the selection process. The first estimate of QTL allele effects is then updated by estimating (re-estimating) the correlation between the allele of the marker and the phenotype in a population of progeny of the selected plant derived by self-crossing, crossing with another selected plant bearing the marker, or by crossing the selected plant with a member of another line or population of plants, e.g., lacking or untyped with respect to the marker. This generates an updated estimate of QTL allele effects. The selection and re-estimation process is then repeated at each cycle, or at intervals of breeding cycles, over the course of the breeding program.

Updating the estimate of QTL allele effects can be accomplished by either replacing the values of the first or prior estimate with the values of a subsequent estimate in a subsequent population of plants. Alternatively, the updating can be performed by combining the data underlying the first correlation between a marker and a phenotype with data from subsequent populations to generate a combined estimate of QTL allele effects. In some embodiments, the updating includes data from the original correlation provided at the start of the breeding program (i.e., contributing to the first estimate of QTL allele effects). Alternatively, the data over a selected window (or subset) of breeding cycles can be combined during the re-estimation to provide an updated estimate of QTL allele effects that is less significantly biased by the genotype of the initial population as the germplasm evolves under the influences of selection during the breeding process. If desired, the window can slide or travel with each subsequent cycle of the breeding process.

The recursively determined estimate of correlation between the marker allele and the phenotype (or recursively determined estimate of QTL allele effects) is typically determined using at least one statistical analysis. Such a statistical analysis favorably accounts for one or more of additive effects, dominance effects, over-dominance effects, epistasis and genotype x environment interactions, within and among QTL (QTL markers). The correlation can be established using any of the statistical methods known in the art for the purpose of identifying QTL markers and estimating QTL effects. For example, such statistical methods include: single point marker analysis, interval mapping, composite interval mapping, penalized regression analysis, complex pedigree analysis, MCMC analysis, MQM analysis, HAPLO-IM$^+$ analysis, HAPLO-MQM analysis, and HAPLO-MQM$^+$ analysis, Bayesian MCMC, ridge regression, identity-by-descent analysis, Haseman-Elston regression. Typically, the statistical analysis is performed with the assistance of a computer, e.g., comprising statistical software for performing the relevant statistical analyses.

In an exemplary embodiment, correspondence between a marker and a phenotype is monitored, e.g., during a breeding program, by providing a first estimate of QTL effects demonstrating a correlation between the marker and a phentoype in a plurality of plants. At least one plant with the marker is selected, optionally from the plurality in which the correlation is established. The selected plant is then crossed to generate a population of progeny. A second estimate of QTL effects is generated by estimating the correlation between the marker and the phenotype in the population of progeny and the first estimate of QTL effects is updated by replacing the first estimate of QTL effects with the second estimate of QTL effects, or by combining the first and second estimates of QTL effects to generate a first updated estimate of QTL effects. At least one plant with the desired marker is selected from among the population of progeny, and the process is optionally repeated one or more times to generate additional generations of progeny selected based on subsequently updated estimates of QTL effects.

Marker assisted selection (MAS) is performed according to the invention by selecting plants with markers demonstrating a correspondence with a desired phenotype based on the recursively determined correlation of QTL effects. Typically a plant or plants selected by MAS is crossed to generate a population of progeny for further analysis and breeding, either for continuing selection or for production of plants with desired phenotypes. Progeny can be generated by self-crossing the selected plant, or by backcrossing or outcrossing the selected plant. Plants selected according to the methods of the invention are also a feature of the invention.

In another embodiment, the invention provides methods for cloning or isolating nucleic acid fragments in linkage disequilibrium with the at least one marker. Such nucleic acids can include additional markers, chromosome intervals and/or nucleic acids comprising QTL. Optionally, the isolated nucleic acid is transformed into a plant to produce a transgenic plant. Typically, the isolated nucleic acid is introduced into a host plant in the context of an expression vector or cassette, in which the nucleic acid is operably linked to a promoter and/or additional expression sequences, e.g., enhancers, and the like. If desired the transgenic plant can be crossed to generate additional plants bearing the introduced nucleic acid. Such transgenic plants and their offspring are also a feature of the invention.

While the methods of the present invention are generally applicable to any plant or animal species of interest, crop plants including corn (maize), soybean, sunflower, sorghum, wheat, rice, flax, cotton, millet and canola are particularly appropriate.

Similarly, essentially any measurable phenotype or trait of interest is amenable to the methods of the present invention. Such a phenotype can be assessed directly, e.g., by visual inspection, or indirectly using appropriate means. For example, with respect to plants, yield (e.g., grain yield, silage yield), stress (e.g., mid-season stress, terminal stress, moisture stress, heat stress, etc.) resistance, disease resistance, insect resistance, resistance to density, kernel number, kernel size, ear size, ear number, pod number, number of seeds per pod, maturity, time to flower, heat units to flower, days to flower, root lodging resistance, stalk lodging resistance, plant height, ear height, grain moisture content, test weight, starch content, oil content, grain composition, starch composition, oil composition, protein composition, nutraceutical content, and the like are all suitable phenotypes in the context of the invention. Other relevant phenotypes will be apparent to those of skill in the art. The phenotype can be a molecular phenotype, such as an expression profile. Alternatively, the phenotype can be an indirect measure of a physical or molecular phenotype represented by a mathematical relationship.

Integrated systems including computers, a user interface, a database including population data and an instruction set for recursively estimate and updating QTL effects are also a feature of the invention.

DETAILED DESCRIPTION

Introduction

Figure 1:
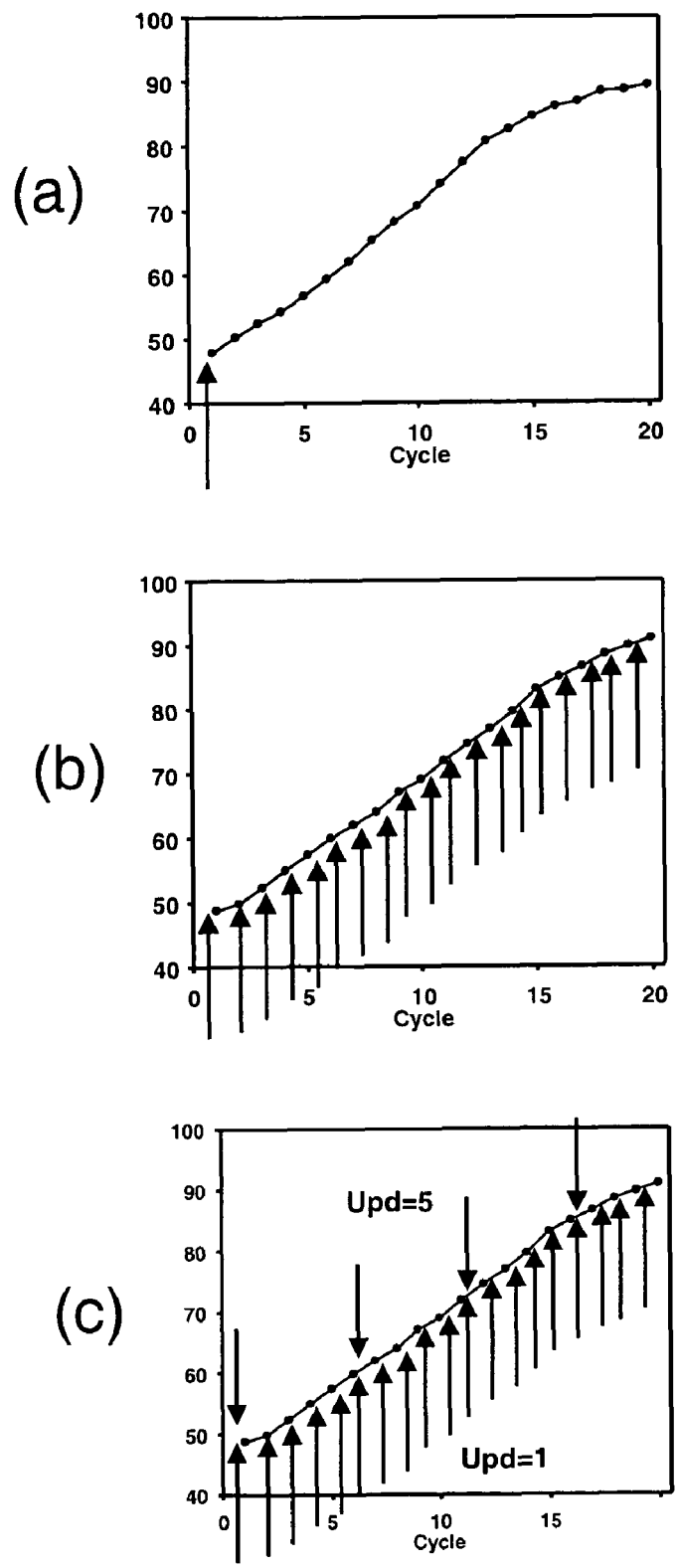
FIG. 1 (*a-c*): Schematic representation of the (a) Mapping Start Only and (b) Mapping As-You-Go approaches to marker assisted selection. Performance of a trait (phenotype) is indicated on the vertical axis. Cycle of the breeding program is indicated on the horizontal axis. (c) Illustrates updating QTL estimate at each cycle and every 5 cycles. Arrows indicate independent estimation of QTL effects.

The present invention provides a novel approach for mapping and selecting quantitative traits that takes into consideration the complex context dependent effects of epistasis and genotype x environment interactions to accelerate generation of desired plant (and/or animal) variants. In brief, the method of the invention involves applying a "Mapping As-You-Go" strategy to the analysis of complex traits, e.g., traits of agronomic interest. The Mapping As-You-Go strategy differs from prior mapping procedures in that the estimates of QTL effects are regularly reevaluated to ensure that the genetic model remains relevant as new germplasm is generated during the breeding process. In conventional marker-assisted selection, QTL effects are estimated only once (i.e., at the "start only") and selection for the duration of the breeding process is based on these fixed estimates.

In practice, the single-estimation or Mapping Start Only approach may be based on the results of a single mapping study or the aggregation of multiple mapping studies. However, for purposes of discussion in this document, the Mapping Start Only approach adopted a single set of QTL estimates in the application of MAS over all cycles of the breeding program to enable forward selection for a fixed target genotype. An example of a Mapping Start Only method is the so-called "Breeding by Design" concept described by Peleman and Rouppe van der Voort (2003) *Trends Plant Sci.* 8:330-334.

The recursive re-estimation of QTL effects throughout a breeding program of the present invention should not be confused with simply improving the resolution of a genetic map, e.g., as occurs by placing additional markers on an established map, or increasing the sample size within the initial population. In conventional marker assisted selection (MAS) programs, the genetic model is fixed at the outset for the duration of the breeding program. That is, numbers, positions, and effects of QTL are estimated at the start and these estimates are used to evaluate, select and intermate germplasm in the breeding program. To the extent that adjustments to the estimate are made, it is for the purpose of increasing the accuracy of the initial estimate.

In contrast, in Mapping-As-You-Go, QTL effects are recursively determined, that is, estimated and re-estimated across populations (e.g., plant populations), as new germplasm is generated during the breeding process, to ensure that the QTL markers and alleles used for evaluation and selection remain relevant as the germplasm evolves under selection. In this way, due to the presence of context dependent effects, the estimated value of a QTL allele may change in magnitude over cycles of the breeding program, and in the extreme case, a different QTL allele may be identified as favorable. Thus, selection pressure on one allele type (or haplotype) may be interspersed with selection pressure on alternative allele types (or haplotypes) over the duration of the breeding program.

These updated estimates are used to inform the model (e.g., by adding or removing markers and/or altering allele preferences), as well as determine which members of a population (e.g., of plants or animals of agronomic interest) are selected and intermated. While many variants can be considered within the context of the Mapping As-You-Go approach, the key steps used described herein are as follows:

i) Estimate the effects of QTL alleles from an initial set of breeding crosses.

ii) Use the information from the initial QTL analysis to construct a target configuration of marker alleles and conduct marker or marker-assisted selection on germplasm representative of that used in the QTL mapping study.

iii) Create a new set of crosses among the selected lines.

iv) Re-estimate the effects of QTL alleles in the set of germplasm created from the new set of crosses.

v) Update the estimates of the QTL effects that will be used in the next cycle of selection.

vi) Select within the new set of crosses on the basis of the updated estimates of QTL effects.

vii) Continue this cyclical process by evolving the estimates of QTL effects as new germplasm is created over cycles of the breeding process.

FIGS. 1(a and b) and 2 show the distinction between the conventional "Mapping Start-Only" approach and the "Mapping As-You-Go" approach to marker-assisted selection.

The Mapping As-You-Go method also provides an effective treatment for the types of errors that can be easily introduced in the estimation of QTL effects in mapping populations. Two common types of error that can occur in QTL mapping studies are: (1) the designation of significant QTL effects when in fact no QTL actually exists in that linkage position (i.e. Type I errors), and (2) the non-identification of significant QTL that do in fact exist (i.e. Type II errors). In both cases, the errors can compromise the definition of the favorable marker configuration and hence reduce the effectiveness of MAS. A third type of error can occur in mapping studies when a true QTL position is correctly identified but the wrong allele is designated as the favorable allele (i.e. Type III errors). In the application of the Mapping As-You-Go method, the impact of these types of errors is confined to a single cycle of the breeding program. That is, any selection pressure on non-QTL, or lack there-of on true QTL, will only apply until the next round of QTL estimates. Thus, errors generated in any given mapping study will have little impact over a longer period of time in the breeding program.

The process of Mapping As-You-Go is initiated by evaluating the association between one or more QTL markers, e.g., the association between identified alleles of one or more marker loci, and one or more phenotypes or traits of interest. For example, a comprehensive molecular marker map can be used to identify one or more polymorphic markers (i.e., markers with more than one distinguishable allele) correlating with variability in the trait under evaluation. Alternatively, a subset of molecular markers corresponding to a subset of the genome, such as a chromosome, a chromosomal region or a linkage group can be employed. A marker demonstrating an initial correlation with the trait of interest, that is, having two or more alleles that segregate in linkage disequilibrium with a measure of variability of the trait of interest, is designated a QTL marker, or simply as a marker.

The association between the marker(s) and the phenotype is evaluated across progeny arising from a single breeding cross, or from multiple related or unrelated breeding crosses. It will be appreciated that the association between the polymorphic marker and the trait of interest may be observed in the progeny of one cross or population, whereas the correlation may not be established in the progeny of another cross or population. The presence or absence of an identifiable effect of a gene associated with a QTL marker is influenced by the genetic background of the individual or individuals in the breeding population, as well as by environmental influences. For example, in the context of a plant breeding program, such environmental variables as soil composition, stress, heat, drought, days of sunshine, pest (e.g., bacterial, fungal or insect) load, etc., can have a significant impact on the growth characteristics and phenotypic attributes of a population under selection.

The influence of genetic background on the phenotypic expression of a gene, such as a QTL, is loosely referred to as "epistasis." In contrast, the influence of the organism's external environment on the phenotypic expression of a gene is referred to as "genotype x environment" interactions. The present invention provides methods for identifying QTL (and QTL markers) that account for the role of epistasis and genotype x environment interactions on a "multi-factorial" phenotypic trait. While the most significant improvements in performance relative to conventional Mapping Start Only methods are achieved where epistasis and genotype x environment interactions are significant, one of skill in the art will recognize that the methods herein described are equally applicable to the situation in which neither epistasis nor genotype x environment interactions have a significant influence on the heritability of a trait of interest. The effects of multiple genes independently contributing to expression of a "polygenic" phentoypic trait are generally referred to as "additive."

Establishing an association between one or more alleles of a QTL marker (or a putative QTL marker, or indeed a QTL) with the trait of interest in a group of organisms, e.g., plants or animals of agronomic interest, generates a first estimate of QTL effects, or QTL allele effects. As discussed above, that estimate of QTL allele effects may be specific to the group or population sampled or may be generalized across a variety of populations. Following generation of the first estimate of QTL allele effects for the QTL marker, at least one organism with the desired marker allele (i.e., the allele exhibiting an association with the phenotype of interest) is selected as the subject of subsequent breeding crosses. The plant can be selected from the same population providing the basis for the estimate of QTL allele effects, or may be chosen from a different group arising from the same or a different breeding population. Indeed, the identified organism can be selected from any available collection of germplasm.

Optionally, in addition to the QTL marker, the organism can be selected on the basis of phenotypic information. The use of additional information relating to phenotype is particularly useful in circumstances where epistasis and/or gene-by-environment interactions play a significant role in expression of the phenotypic trait. While the use of phenotypic data is most frequently used in early stages of a Mapping As-You-Go analysis, it will be understood that the use of phenotypic data, in addition to detection of the QTL marker can be utilized with favorable results at any stage of the mapping or selection process.

The selected organism is then crossed to generate a population of progeny. The cross can be between selected individuals, each of which possesses the QTL marker of interest, or between a selected individual and one or more individuals chosen from another line or population, which may or may not also have the QTL marker of interest. Such a new line or population can optionally also be evaluated for the presence or absence of the QTL marker of interest.

Using the same or a different molecular marker map, the association between one or more QTL markers, which can be identical to or different from the QTL marker(s) previously evaluated, is evaluated to again generate an estimate of QTL allele effects, i.e., a second estimate of QTL allele effects. The second estimate of QTL allele effects is then used to update the first estimate of QTL allele effects, either by replacing the first estimate, or by combining the first and second estimates to generate an updated estimate of QTL allele effects. This updated estimate of QTL allele effects is then utilized to select progeny of the cross with a QTL marker of interest.

This process of crossing and selecting using recursively updated estimates of QTL allele effects provides the basis of the Mapping As-You-Go strategy, and can be continued for as many cycles of selecting and breeding as desired based on the particular population or populations, and the particular trait of interest and application.

The Mapping As-You-Go strategy provides a greater rate of response to selection than either phenotypic selection strategies, or marker assisted selection (MAS) strategies based on a single estimate of QTL effects. The enhanced rate of response is particularly marked for quantitative traits that are influenced by the effects of epistasis and/or genotype x environment interactions. Thus, improved varieties, e.g., inbreds and hybrids, can be created more rapidly within a breeding program applied to a single population or to multiple related or unrelated populations.

The development of the Mapping As-You-Go strategy arose from a series of investigations into the mapping of quantitative traits using a model that explicilty accounted for the effects of epistasis and genotype x environment interactions. These investigations used the E(NK) model to simulate the effects of epistasis and genotype x environment interaction effects in the QTL analysis and selection processes. However, while the E(NK) model is particularly well suited to the methods of the present invention, any statistical model or method which takes into consideration these effects is also suitable. Additionally, the generalized Mapping As-You-Go strategy can be favorably applied in circumstances where the only observable gene effects act in an additive manner, e.g., where epistasis and genotype x environment interactions play an insignificant or negligible (or undetectable or non-existant) role in expression of the phenotypic trait.

The Mapping As-You-Go strategy differs from existing approaches in that in all other QTL mapping approaches the emphasis is placed on conducting a single mapping study to estimate QTL effects, in effect producing a "snap-shot" of QTL numbers, positions, and effects. This same estimate is then used throughout the mapping and selection process. These existing approaches are useful if the genes associated with the QTL act in an additive manner, as these effects are expected to be consistent within and among crosses, regardless of the environment in which the organisms are grown or the conditions under which the organisms are raised, and over the course of selection. Indeed, these existing mapping approaches are typically predicated on assuming the absence of epistasis and genotype x environment interactions. However, in the presence of epistasis and/or genotype x environment interactions, the effects of the QTL alleles are context dependent. The Mapping As-You-Go strategy, by reevaluating the effects and updating the estimate of QTL effects as the context changes, in parallel with the selection process, makes it possible to apply the appropriate selection pressure (i.e., on the basis of the appropriate QTL marker or markers) regardless of changes in the environmental or genetic context.

Definitions

The terminology used herein is for the purpose of describing particular embodiments only, and is not intended to be limiting. As used in this specification and the appended claims, the singular forms "a," "an" and "the" include plural referents unless the content clearly dictates otherwise. Thus, for example, reference to "a phenotype" or "an attribute" includes a combination of two or more phenotypes or attributes; reference to "progeny" or "germplasm" includes mixtures of progeny or germplasms, e.g., from the same or different sources, and the like.

Unless defined otherwise, all technical and scientific terms used herein have the same meaning as commonly understood by one of ordinary skill in the art to which the invention pertains. Although any methods and materials similar or equivalent to those described herein can be used in the practice of the present invention, preferred materials and methods are described herein. In describing and claiming the present invention, the following terminology will be used in accordance with the definitions set out below. The terms defined below are more fully defined by reference to the specification as a whole. Section headings provided throughout the specification are provided for convenience and are not limitations to the various objects and embodiments of the present invention.

An "estimate of correlation" is a mathematical representation of a statistical relationship between a marker allele or haplotype and a phenotype of interest. The correlation can be established using any statistical methods known in the art for the purpose of identifying a genetic marker and evaluating the strength of the association between the marker and the phenotype, e.g., determining the magnitude of the contribution of the gene to phenotypic expression and/or determining the proximity of linkage between the marker and the gene influencing the phenotype of interest. An "estimate of QTL effects" is an estimate of correlation between a QTL marker or haplotype and a phenotype.

The term "recursively determined" indicates that the, e.g., estimate of correlation or estimate of QTL allele effects, is produced by repeatedly evaluating the statistical relationship between the marker or haplotype and the phenotype of interest. Each repetition is an independent analysis of the strength of correlation between the marker or haplotype and the phenotype in a sampled population. Thus, in the context of a plant breeding program, an estimate of QTL allele effects is recursively determined when the correlation between the marker or haplotype and the phenotype is determined in a population of progeny selected from the breeding population at successive intervals (generations) during the breeding process.

The term "phenotype," or "phenotypic trait" or "trait" refers to one or more observable traits of an organism. The phenotype can be observable to the naked eye, or by any other means of evaluation known in the art, e.g., microscopy, biochemical analysis, genomic analysis, etc. As used herein, the term phenotype also includes an indirect measure of a trait expressed as a mathematical relationship. In some cases, a phenotype is directly controlled by a single gene or genetic locus, i.e., a "single gene trait." In other cases, a phenotype is the result of several genes, or "quantitative trait loci" ("QTL"), acting together. Such a phenotype can generally be described in quantitative terms, e.g., height, weight, oil content, days to germination, etc, and, therefore, can be assigned a "phenotypic value" which corresponds to a quantitative value for the phenotypic trait.

A "molecular phenotype" is a phenotype detectable at the level of a population of (one or more) molecules. Such molecules can be nucleic acids, most commonly RNA (e.g., detected as crude RNA, polyA RNA, mRNA, amplification products, cDNA products, and the like), proteins, or metabolites. For example, a molecular phenotype can be an expression profile for one or more gene products, e.g., at a specific stage of plant development, in response to an environmental condition or stress, etc. Expression profiles are typically evaluated at the level of RNA or protein, e.g., on a nucleic acid array or "chip" or using antibodies or other binding proteins.

An "expression product" is any product transcribed in a cell from a DNA (e.g., from a gene) or translated from an RNA (e.g., a protein). Example expression products include mRNAs and proteins.

An "expression profile" is the result of detecting a representative sample of expression products from a cell, tissue or whole organism, or a representation (picture, graph, data table, database, etc.) thereof. For example, many RNA expression products of a cell or tissue can simultaneously be detected on a nucleic acid array, or by the technique of differential display or modification thereof such as Curagen's "GeneCalling™" technology. Similarly, protein expression products can be tested by various protein detection methods, such as hybridization to peptide or antibody arrays, or by screening phage display libraries. A "portion" or "subportion" of an expression profile, or a "partial profile" is a subset of the data provided by the complete profile, such as the information provided by a subset of the total number of detected expression products.

The term "genotype" refers to the genetic constitution, as contrasted with the observable trait (the phenotype). The term genotype can be used to refer to an individual's genetic constitution at a single locus, at multiple loci, or, more generally, the term genotype can be used to refer to an individual's genetic make-up for all the genes in its genome.

The term "haplotype" refers more specifically to an individual's genotype at multiple, generally linked, loci. For example, a haplotype can be an individual's genotype for multiple loci or genetic markers on a single chromosome. In this case, the term "chromosomal haplotype" is, alternatively, used. Similarly, an individual's genotype for multiple loci (or markers) within a defined region of a chromosome is, optionally, referred to as a "regional haplotype."

The term "quantitative trait locus" or "QTL" refers to a polymorphic genetic locus with at least two alleles that differentially affect the expression of a multifactorial or polygenic phenotypic trait (e.g., a polygenic "quantitative trait") on at least one genetic background, e.g., in at least one breeding population or sample of progeny.

"Genetic markers" are loci, or DNA sequences which both vary (are polymorphic) between individual's in a population, and can be detected by one or more analytic methods, e.g., RFLP, AFLP, isozyme, SNP, SSR, and the like. A "genetic marker" or "molecular marker" refers to a genetic locus (a "marker locus") that can be used as a point of reference when identifying a genetically linked locus such as a QTL. Such a marker is also referred to as a QTL marker. The term also refers to nucleic acid sequences complementary to the genomic sequences, such as nucleic acids used as probes.

The term "associated with" or "associated," when referring to a nucleic acid (e.g., a genetic marker) and a phenotype in the context of the present invention, refers to a nucleic acid and a phenotypic trait that are in linkage disequilibrium. The term "linkage disequilibrium" refers to a non-random segregation of genetic loci. This implies that such loci are in sufficient physical proximity along a length of a chromosome that they tend to segregate together with greater than random frequency.

The term "genetically linked" refers to genetic loci (including genetic marker loci) that are in linkage disequilibrium and statistically determined not to assort independently.

The term "additive effects" or "additive" when referring to a quantitative trait indicates that the individual genetic components of the trait, that is, the genes contributing to a phenotype, act independently of each other and of other genes in the genetic background of the plant or animal, and that the effects of each contributing gene can be measured quantitatively. In contrast, "non-additive effects" result from epistasis and/or genotype x environment interactions. In a non-additive system, the individual genes act in an interdependent manner, in which the contribution of each gene is not quantitatively detectable irrespective of alleles at other loci.

The term "epistasis" traditionally refers to the ability of one gene or genetic locus to alter or mask the expression of a gene at a second genetic locus. More generally, "epistasis" refers to the effect of genetic background or genetic environment on the expression of an allele at a locus, such as a QTL. That is, an epistatic effect means that the expression or effect on a trait of an allele at one locus is dependent upon the expression or effect of at least one other gene at another locus. The term epistasis, or "genotype x genotype interaction," is contrasted with the phrase "genotype x environment" interactions, which refers to extra-genic interactions influencing the expression of a gene or genes.

"Marker Assisted Selection" or "MAS" refers to the practice of selecting for desired phenotypes among members of a breeding population using genetic markers.

The term "plant population" or "population of plants" indicates a group of plants, for example, from which samples are taken for evaluation, e.g., estimation of QTL effects, and/or from which plants are selected for breeding purposes. Most commonly, the term plant population relates to a breeding population of plants. That is a plant population from which members are selected and crossed to produce progeny in a breeding program. Nonetheless, the population members from which the estimate of QTL effects is obtained need not be identical to the population members ultimately selected for breeding to obtain progeny plants, e.g., progeny plants used for subsequent cycles of analysis. In some instances, a plant population may include parental plants as well as one or more progeny plants derived from the parental plants. In some instances, a plant population is derived from a single biparental cross, e.g., a population of progeny of a cross between two parental plants. Alternatively, a plant population includes members derived from two or more crosses involving the same or different parental plants.

The term "crossed" or "cross" in the context of this invention means the fusion of gametes, e.g., via pollination to produce progeny (i.e., cells, seeds, or plants) in the case of plants. The term encompasses both sexual crosses (the pollination of one plant by another) and, in the case of plants, selfing (self-pollination, i.e., when the pollen and ovule are from the same plant).

The phrase "hybrid plants" refers to plants which result from a cross between genetically different individuals.

The phrase "tester parent" refers to a parent that is genetically different from a set of lines to which it is crossed. The cross is for purposes of evaluating differences among the lines in topcross combination. Using a tester parent in a sexual cross allows one of skill to determine the association of the environment on the phenotypic trait with expression of quantitative trait loci in a hybrid combination.

The phrases "topcross combination" and "hybrid combination" refer to the processes of crossing a single tester parent to multiple lines. The purposes of producing such crosses is to evaluate the ability of the lines to produce desirable phenotypes in hybrid progeny derived from the line by the tester cross.

The term "introgression" refers to the transmission of a desired allele of a genetic locus from one genetic background to another. For example, introgression of a desired allele at a specified locus can be transmitted to at least one progeny via a sexual cross between two parents of the same species, where at least one of the parents has the desired allele in its genome. Alternatively, for example, transmission of an allele can occur by recombination between two donor genomes, e.g., in a fused protoplast, where at least one of the donor protoplasts has the desired allele in its genome. The desired allele can be, e.g., a transgene or a selected allele of a marker or QTL.

The terms "nucleic acid," "polynucleotide," "polynucleotide sequence" and "nucleic acid sequence" refer to single-stranded or double-stranded deoxyribonucleotide or ribonucleotide polymers, or chimeras thereof. As used herein, the term can additionally or alternatively include analogs of naturally occurring nucleotides having the essential nature of natural nucleotides in that they hybridize to single-stranded nucleic acids in a manner similar to naturally occurring nucleotides (e.g., peptide nucleic acids). Unless otherwise indicated, a particular nucleic acid sequence of this invention optionally encompasses complementary sequences, in addition to the sequence explicitly indicated. The term "gene" is used to refer to, e.g., a cDNA and an mRNA encoded by the genomic sequence, as well as to that genomic sequence.

The term "homologous" refers to nucleic acid sequences that are derived from a common ancestral gene through natural or artificial processes (e.g., are members of the same gene family), and thus, typically, share sequence similarity. Typically, homologous nucleic acids have sufficient sequence identity that one of the sequences or its complement is able to selectively hybridize to the other under selective hybridization conditions. The term "selectively hybridizes" includes reference to hybridization, under stringent hybridization conditions, of a nucleic acid sequence to a specified nucleic acid target sequence to a detectably greater degree (e.g., at least 2-fold over background) than its hybridization to non-target nucleic acid sequences and to the substantial exclusion of non-target nucleic acids. Selectively hybridizing sequences have about at least 80% sequence identity, preferably at least 90% sequence identity, and most preferably 95%, 97%, 99%, or 100% sequence identity with each other. A nucleic acid that exhibits at least some degree of homology to a reference nucleic acid can be unique or identical to the reference nucleic acid or its complementary sequence.

The term "isolated" refers to material, such as a nucleic acid or a protein, which is partially or substantially free from components that normally accompany or interact with it in its naturally occurring environment. The isolated material optionally comprises material not found with the material in its natural environment, e.g., a cell. In addition, if the material is in its natural environment, such as a cell, the material has been placed at a location in the cell (e.g., genome or subcellular organelle) not native to a material found in that environment. For example, a naturally occurring nucleic acid (e.g., a promoter) is considered to be isolated if it is introduced by non-naturally occurring means to a locus of the genome not native to that nucleic acid. Nucleic acids which are "isolated" as defined herein, are also referred to as "heterologous" nucleic acids.

The term "recombinant" indicates that the material (e.g., a nucleic acid or protein) has been synthetically (non-naturally) altered by human intervention. The alteration to yield the synthetic material can be performed on the material within or removed from its natural environment or state. For example, a naturally occurring nucleic acid is considered a recombinant nucleic acid if it is altered, or if it is transcribed from DNA which has been altered, by means of human intervention, e.g., performed on the cell from which it originates.

The term "introduced" when referring to a heterologous or isolated nucleic acid refers to the incorporation of a nucleic acid into a eukaryotic or prokaryotic cell where the nucleic acid can be incorporated into the genome of the cell (e.g., chromosome, plasmid, plastid or mitochondrial DNA), converted into an autonomous replicon, or transiently expressed (e.g., transfected mRNA). The term includes such nucleic acid introduction means as "transfection," "transformation" and "transduction."

The term "host cell" means a cell that contains a heterologous nucleic acid, such as a vector, and supports the replication and/or expression of the nucleic acid. Host cells may be prokaryotic cells such as *E. coli*, or eukaryotic cells such as yeast, insect, amphibian, or mammalian cells. Host cells also include monocotyledonous or dicotyledonous plant cells. In the context of the invention, an exemplary monocotyledonous host cell is a maize host cell. An exemplary dicotyledonous host cell is a soybean cell.

The term "transgenic" plant or animal refers to a plant or animal which comprises within its genome a heterologous polynucleotide. Generally, the heterologous polynucleotide is stably integrated within the genome such that the polynucleotide is passed on to successive generations. The heterologous polynucleotide may be integrated into the genome alone or as part of a recombinant expression cassette. "Transgenic" is used herein to refer to any cell, cell line, tissue, part or organism, the genotype of which has been altered by the presence of heterologous nucleic acid including those transgenic organisms or cells initially so altered, as well as those created by crosses or asexual propagation from the initial transgenic organism or cell. The term "transgenic" as used herein does not encompass the alteration of the genome (chromosomal or extra-chromosomal) by conventional breeding methods (i.e., crosses) or by naturally occurring events such as random cross-fertilization, non-recombinant viral infection, non-recombinant bacterial transformation, non-recombinant transposition, or spontaneous mutation. Examples of processes by which a transgenic organism can be produced are described below, and include electroporation, microinjection, *Agrobacterium*-mediated transformation, biolistic methods, in planta techniques, and the like.

The term "plant" includes any of: whole plants, plant organs (e.g., leaves, stems, roots, etc.), tissues, seeds, plant cells, and/or progeny of the same. Similarly, "plant cell," as used herein includes, without limitation, seeds, suspension cultures, embryos, meristematic regions, callus tissue, leaves, roots, shoots, gametophytes, sporophytes, pollen, and microspores. In addition, the term "plant" encompasses in silico representations of part or all of a plant's genetic constitution. Similarly the term "animal" encompasses whole animals, animal organs, tissues, cells, gametes, and/or progeny, etc., as well as in silico representations of part or all of the genetic constitution of an animal.

Marker Assisted Selection and Breeding

One significant motivation for development of QTL markers in species of agronomic interest, e.g., crops and domesticated livestock and fowl, is the potential for increased efficiency in breeding through marker assisted selection (MAS). A common goal of commercial breeding efforts is to combine disparate phenotypic traits, originating in different organisms, strains, lines or populations, for example, disease resistance loci and genes for high yield, to develop improved plant (e.g., crop, livestock) varieties. Phenotypic screening for a trait of interest, such as disease resistance, for large numbers of samples can be expensive, as well as time consuming. In addition, phenotypic screening alone is often unreliable due to the effects of epistasis and non-genetic (e.g., environmental) contributions to the phenotype. MAS offers the advantage over field evaluation in that it can be performed at any time of year regardless of the growing season or developmental stage, as well as facilitating evaluation of organisms grown in disparate regions or under different conditions.

For the purposes of clarity and brevity, the following discussion relates to the application of the methods of the invention in the context of plant breeding programs. However, one of skill in the art will immediately recognize that the methods described herein are likewise applicable to breeding of animals, e.g., livestock and domesticated fowl of agronomic importance. Accordingly, the utilization of the term plant is intended to exemplify rather than limit the scope of the invention.

The methods of the present invention are applicable to any phenotype with an underlying genetic component, i.e., any heritable trait. Thus, the methods of the present invention are not to be limited to the mapping and selection of any particular trait or set of traits. Rather, a breeder, of ordinary skill, desiring to breed plants with a particular phenotypic trait or attribute, or with a combination of selected traits, can apply the general methods described herein to select and breed plants meeting specified criteria. The vast majority of phenotypes of agronomic importance in plants and animals are determined by multiple genetic loci, i.e., by QTL. In the context of an exemplary plant breeding program, quantitative phenotypes include, yield (e.g., grain yield, silage yield), stress (e.g., mid-season stress, terminal stress, moisture stress, heat stress, etc.) resistance, disease resistance, insect resistance, resistance to density, kernel number, kernel size, ear size, ear number, pod number, number of seeds per pod, maturity, time to flower, heat units to flower, days to flower, root lodging resistance, stalk lodging resistance, plant height, ear height, grain moisture content, test weight, starch content, oil content, grain composition, starch composition, oil composition, protein composition, nutraceutical content, and the like.

In addition to phenotypes directly assessable by the naked eye, with or without the assistance of one or more manual or automated devices, included, e.g., microscopes, scales, rulers, calipers, etc., many phenotypes can be assessed using biochemical and/or molecular means. For example, oil content, starch content, protein content, nutraceutical content, as well as their constituent components can be assessed, optionally following one or more separation or purification step, using one or more chemical or biochemical assay. Molecular phenotypes, such as metabolite profiles or expression profiles, either at the protein or RNA level, are also amenable to evaluation according to the methods of the present invention. For example, metabolite profiles, whether small molecule metabolites or large bio-molecules produced by a metabolic pathway, supply valuable information regarding phenotypes of agronomic interest. Such metabolite profiles can be evaluated as direct or indirect measures of a phenotype of interest. Similarly, expression profiles can serve as indirect measures of a phenotype, or can themselves serve directly as the phenotype subject to analysis for purposes of marker correlation. Expression profiles are frequently evaluated at the level of RNA expression products, e.g., in an array format, but may also be evaluated at the protein level using antibodies or other binding proteins.

In addition, in some circumstances it is desirable to employ a mathematical relationship between phenotypic attributes rather than correlating marker information independently with multiple phenotypes of interest. For example, the ultimate goal of a breeding program may be to obtain crop plants which produce high yield under low water, i.e., drought, conditions. Rather than independently correlating QTL effects for yield and resistance to low water conditions, a mathematical indicator of the yield and stability of yield over water conditions can be correlated with QTL effects. Such a mathematical indicator can take on forms including; a statistically derived index value based on weighted contributions of values from a number of individual traits, or a variable that is a component of a crop growth and development model or an ecophysiological model (referred to collectively as crop growth models) of plant trait responses across multiple environmental conditions. These crop growth models are known in the prior art and have been used to study the effects of genetic variation for plant traits and map QTL for plant trait responses. See references by Hammer et al. 2002. European Journal of Agronomy 18: 15-31, Chapman et al. 2003. Agronomy Journal 95: 99-113, and Reymond et al. 2003. Plant Physiology 131: 664-675.

While the methods described herein can effectively be used to identify and/or select plants with any desired phenotype, regardless of whether the trait is the result of one or more genes, the methods of the invention provide the greatest increases in efficiency over conventional mapping and marker assisted selection methods where the trait is genetically complex. Furthermore, while little improvement in efficiency is observed with respect to conventional mapping and selection procedures for polygenic traits resulting from multiple genes having purely additive effects, significant improvements in efficiency are obtained using the methods of the present invention in situations in which the genes contributing to the phenotype act in a non-additive manner, i.e., are subject to context dependent effects, e.g., epistatic and/or genotype x environment interactions.

Genetic marker alleles, i.e., QTL markers (or simply markers), or alternatively, identified QTL alleles, are used to identify plants that contain a desired genotype at one or more loci, and that are expected to transfer the desired genotype, along with a desired phenotype to their progeny. Marker alleles (or QTL alleles) can be used to identify plants that contain a desired genotype at one locus, or at several unlinked or linked loci (e.g., a haplotype), and that would be expected to transfer the desired genotype, along with a desired phenotype to their progeny. Similarly, by identifying plants lacking the desired allele, plants with an undesirable phenotype, e.g., disease susceptible plants, can be identified, and, e.g., eliminated from subsequent crosses. It will be appreciated that for the purposes of MAS, the term marker can encompass both marker and QTL loci as both can be used to identify plants with a desired phenotype.

After a desired phenotype and a polymorphic chromosomal locus, e.g., a marker locus or QTL, are determined to segregate together (i.e., are determined to be in linkage disequilibrium), alleles corresponding to the desired phenotype are selected. In brief, a nucleic acid corresponding to the marker nucleic acid is detected in a biological sample from a plant to be selected. This detection can take the from of hybridization of a probe nucleic acid to a marker, e.g., using allele-specific hybridization, Southern analysis, northern analysis, in situ hybridization, hybridization of primers followed by PCR amplification of a product including the marker, or the like. A variety of procedures for detecting markers are described herein, e.g., in the section entitled "DETECTION OF MARKER LOCI." After the presence (or absence) of a particular marker in the biological sample is verified, the plant is selected and, optionally, crossed to produce progeny plants.

When a population is segregating for multiple loci affecting one or multiple traits, e.g., multiple loci involved in resistance to single disease, or multiple loci each involved in resistance to different diseases, the efficiency of MAS compared to phenotypic screening becomes even greater because all the loci can be processed in the lab together from a single sample of DNA. Thus, use of marker information for each of the traits in the breeding process is facilitated.

Because applied breeding programs evaluate large numbers of progeny derived from multiple crosses, they provide the necessary phenotypic data for identifying and selecting favorable alleles at QTL for a wide range of agronomic traits. By integrating QTL analyses into existing breeding programs, the power, precision and accuracy associated with large numbers of progeny can be attained. Furthermore, inferences about QTL can be drawn across the breeding program rather than being limited to the sample of progeny from a single cross. Integrating QTL identification into existing breeding programs makes the information much more valuable for MAS, because the QTL apply to agronomically realistic situations in the field. This is more efficient than conventional strategies involving a series of discrete processes which include the production of progeny from carefully chosen contrasting inbred lines, the identification of QTL, the assembly of QTL, and independent testing and evaluation of these QTL in numerous backgrounds through modified backcrossing strategies.

QTL Mapping

While much of the ensuing discussion relates to the mapping of QTL, it will be appreciated that the methods of the invention are equally applicable to the mapping of other genetic loci, e.g., those underlying single gene traits. Accordingly, even where QTL are referred to exclusively for the sake of clarity and simplicity, genes underlying single gene traits are to be understood to be assessable by essentially similar methods. Similarly, the methods are equally applicable to traits which are continuously variable, such as grain yield, height, oil content, response to stress (e.g., terminal or midseason stress) and the like, or to meristic traits that are multi-categorical, but can be analyzed as if they were continuously variable, such as days to germination, days to flowering or fruiting, and to traits with are distributed in a non-continuous (discontinuous) or discrete manner.

Numerous statistical methods have been developed for QTL mapping in experimental populations (see, e.g., Jansen (1996) *Trends Plant Sci* 1:89), any of which are suitable for identifying QTL markers and/or estimating QTL effects. For example, common statistical methods employed in the context of QTL mapping and accessible to those of skill in the art include standard linear models, such as ANOVA or regression, maximum likelihood methods, such as expectation-maximization algorithms, (e.g., Lander and Botstein (1989) Mapping Mendelian factors underlying quantitative traits using RFLP linkage maps. *Genetics* 121:185-199; Jansen (1992) A general mixture model for mapping quantitative trait loci by using molecular markers. *Theor. Appl. Genet.* 85:252-260, Jansen (1993) Maximum likelihood in a generalized linear finite mixture model by using the EM algorithm. *Biometrics* 49:227-231; Jansen (1994) Mapping of quantitative trait loci by using genetic markers: an overview of biometrical models. In J. W. van Ooijen and J. Jansen (eds.), *Biometrics in Plant breeding: applications of molecular markers*, pp. 116-124. CPRO-DLO Metherlands; Jansen (1996) A general Monte Carlo method for mapping multiple quantitative trait loci. Genetics 142:305-311; and Jansen and Stam (1994) High Resolution of quantitative trait into multiple loci via interval mapping. *Genetics* 136:1447-1455). Exemplary statistical methods include single point marker analysis, interval mapping, composite interval mapping, penalized regression analysis, complex pedigree analysis, MCMC analysis, MQM analysis, HAPLO-IM$^+$ analysis, HAPLO-MQM analysis, and HAPLO-MQM$^+$ analysis, Bayesian MCMC, ridge regression, identity-by-descent analysis, Haseman-Elston regression, any of which are suitable in the context of the present invention. Any of these approaches are typically mathematically intensive and are usually performed by those of skill in the art with the assistance of a computer based system. Appropriate statistical packages are available from a variety of public and commercial sources, and are known to those of skill in the art.

Virtually all published reports on QTL mapping in crop species have been based on the use of the bi-parental cross (Lynch and Walsh (1997) *Genetics and Analysis of Quantitative Traits* Sinauer Associates, Sunderland). Typically, this experimental protocol involves deriving 100 to 300 segregating progeny from a single cross of two divergent inbred lines (e.g., selected to maximize phenotypic and molecular marker differences between the lines). The segregating progeny are genotyped for multiple marker loci and evaluated for one to several quantitative traits in several environments. QTL are then identified as significant statistical associations between genotypic values and phenotypic variability among the segregating progeny. The strength of this experimental protocol comes from the utilization of the inbred cross, because the resulting $F_1$ parents all have the same linkage phase. Thus, after selfing of the $F_1$ plants, all segregating progeny ($F_2$) are informative and linkage disequilibrium is maximized, the linkage phase is known, there are only two QTL alleles, and, except for backcross progeny, the frequency of each QTL allele is 0.5.

Recent efforts have been made to adapt the methods of analysis developed for bi-parental experimental populations to (diallel) breeding populations (Rebai and Goffinet (1993) *Theor Appl Genet* 86:1014). However, the principles that underlie analysis methods for the bi-parental inbred cross are not adequate for application to breeding populations, because the genetic structures of cross and population are different. In contrast to selection of lines in bi-parental experimental populations, the selection of lines for breeding is based on maximizing genetic variability of traits useful for agronomic performance. As a consequence, the crosses are not necessarily informative at all marker loci and QTL, linkage disequilibrium exists among the ($F_2$) progeny within families, but not necessarily across the breeding population. The linkage phase is not consistent across the breeding population, multiple QTL alleles can exist and the frequency of each will vary between 0 and 1.

Theoretical considerations (Soller et al. (1978) *Biometrics* 34:47; Jansen (1994) *Genetics* 138:871; Zeng (1994) *Genetics* 136:1457), Monte Carlo simulations (Van Ooijen (1994) *Theor Appl Genet* 84:517; Beavis (1994) supra; Beavis (1998) *QTL Analyses: Power, Precision and Accuracy*, in *Molecular Analysis of Complex Traits*, AH Paterson (ed) pp 145-161, CRC Press), and recent experimental results (Openshaw and Frascaroli (1997) 52 $^{nd}$ *Annual corn and sorghum research conference*, pp 44-53. American Seed Trade Association, Washington D.C.) have clearly shown that studies in plant species have been inadequate for estimating numbers, magnitudes and distribution of QTL for most quantitative traits. These studies show there is little power to identify markers linked to QTL or to accurately estimate their genetic effects, unless a large number of progeny are evaluated. More importantly, inferences about identified QTL and their estimated genetic effects are limited to the sample of progeny evaluated in the experiment. Additional evaluation in samples of progeny from other crosses is needed before inferences can be extended beyond the initial breeding population. From a breeding perspective, this is a severe limitation.

Recently, approaches for combining multiple line crosses in plant breeding populations based on fixed effects, random effects and mixed effects models for combining multiple line crosses in plant breeding populations have been proposed. (U.S. Pat. No. 6,399,855 to Beavis, issued Jun. 4, 2002; and Xu (1998) *Genetics* 148:517; Xie et al. (1998) *Genetics* 149:1139). These strategies treat QTL effects as nested within families, and provide a straightforward and robust tool for analyzing multiple plant breeding families.

Another simple approach is to apply the existing methods developed for single line crosses and to use computer assisted analysis to analyze multiple populations one-by-one. The QTL likelihood curves are then summed up in order to generate an overall QTL likelihood. This approach is very straightforward, but does not model relationships between families. As for the method, one has a choice of interval mapping (Lander and Botstein (1989) *Genetics* 121:185), regression mapping (Haley and Knott (1992) *Heredity* 69:315) or MQM mapping (Jansen (1994) *Genetics* 138:871). See, e.g., Spelman et al. (1996) *Genetics* 144:1799, for an illustration with multiple dairy cattle families.

Jansen and Beavis describe methods which consider the relationships between related families in a breeding population. Using molecular marker information, identity-by-descent (IBD) from parent to offspring throughout the populations is evaluated, using HAPLO-IM$^+$ and HAPLO-MQM$^+$ and HAPLO-MQM models (WO 01/49104 by Jansen and Beavis, filed Dec. 21, 2000, entitled "MQM Mapping using Haplotyped Putative QTL-Alleles: A Simple Approach for Mapping QTL in Plant Breeding Populations).

The above approaches, regardless of the statistical method employed to assess QTL number, position and effects, were previously applied only at the outset of a breeding program, i.e., these are all Mapping Start Only approaches. That is, markers that segregate in a particular inbred cross, or in a series of related inbred crosses, were identified and found by any of these statistical approaches to correlate with variation in a phenotype, i.e., as QTL markers. These markers were evaluated at a single time point, in a particular population of plants, selected at the outset of the breeding program. Accordingly, these estimates were set for the duration of the breeding program. Any further improvement in the precision of the estimates of QTL effects are made by either adding new markers to the map (i.e., previously unmapped molecular markers) or by evaluating the correspondence between mapped markers and phenotype in another, independent, population of plants. In either case, the estimates were made essentially de novo, disregarding the values of prior estimates.

For example, Jansen (1994), *Genetics* 138:871, described a general two-step MQM procedure to find markers closely linked to QTL and for using these markers as cofactors in QTL analysis. In this approach, a set of markers covering the entire genome is selected, these markers are regressed simultaneously, and a statistical elimination procedure is performed to find markers in plausible QTL regions. Such markers are selected via a backward elimination approach on the basis of a 2% significance threshold per marker test. Second, an approach for precision mapping of QTL within marker intervals is applied. The presence of a QTL for a particular genomic marker interval is tested at a genome-wide 5% significance level, while simultaneously fitting the selected markers from the first step in the model of analysis. Hence, the markers selected in the first step function as cofactors in the model used in the second step. Markers inside a small window around the position under study are not used as cofactors. Genome-wide significance thresholds for MQM mapping can be obtained by simulation ("parametric bootstrapping") as in Jansen (1994), supra. This is a computer-intensive task.

This approach was extended to consider between-family information as well as information regarding phenotype and marker segregation within families derived from a single bi-parental cross. In this approach, the effects of haplotyped QTL-alleles across families, and not the effects of allele substitution within families, are evaluated across families. The latter approach provides methods which can cope with QTL segregating in only a subset of the families and which exploit within-family variation, but in addition also consider between-family variation. The allele effects of segregating and non-segregating QTL contribute to the differences between families, but there can also be other genetic and non-genetic sources of variation (e.g., epistatic interactions). The HAPLO-MQM$^+$ model described by Jansen and Beavis WO 01/49104 includes parameters to account and test for these differences.

The present invention differs from the above approaches, in that the estimates of QTL effects are repeatedly reestimated throughout the breeding program, rather than being set at the outset of the program. Thus, at each cycle in a breeding program (where a cycle is a sequence of marker assisted selection followed by crossing of one or more selected plants to generate progeny), marker and phenotype data are evaluated for correlation and an estimate of QTL allele effects, relevant to the population sampled in the cycle, is generated. Alternatively, the updating by re-estimation can be performed at intervals of greater than 1 cycle, e.g., updating at every other cycle, at every fifth cycle, at every 10th cycle, etc. Updating at each cycle of the breeding program typically offers the greatest increase in efficiency towards a desired phenotype is compared to traditional Mapping Start Only methods. However, because estimating QTL effects from population data carries significant attendant costs, in practice, it is desirable to reduce the frequency at which updating is performed. The length of the interval at which updating optimally occurs will vary with the genetic architecture of the trait, and the relatedness of the constituent populations. For example, where the influence of epistasis is low a long interval between estimates is permissible, e.g., every 5 cycles, every 10 cycles, or more. In contrast, where epistasis is a significant factor in determining phenotype, updating at frequent intervals, e.g., every 1, 2 or 5 cycles, will provide better results. Similarly, where the plants or plant families in the population are substantially related, longer intervals can be employed without sacrificing efficiency of selection. Whereas, in circumstances where the germplasm is derived from numerous and/or disparate sources, more frequent updating intervals are desirable.

The estimates of QTL allele effects can be updated in at least two ways to ensure their relevance at any juncture in a breeding program. Estimates of QTL allele effects can be updated by evaluating the correspondence between alleles at one or more QTL markers and a phenotype in a population, e.g., of progeny of a selected plant, and replacing the values of a prior estimate of QTL allele effects for the next cycle of MAS. For example, a prior estimate of QTL allele effects is favorably replaced by a new estimate when the statistical analysis demonstrates that an allele or marker previously shown to correlate, no longer associates with the phenotype of interest, or when a marker that has not previously been found to segregate in disequilibrium with a phenotype now demonstrates a statistically significant correlation between an allele and the phenotype. Alternatively, the correlation data from the population of progeny can be combined with the data from a previous cycle or cycles to generate a revised estimate of QTL allele effects to revise the model on which selection is based. At each cycle of updating, the same or different statistical analysis can be performed, e.g., selected on the basis of the population structure. Throughout the duration of a breeding program, one or both of these approaches can be employed to revise the estimates of QTL allele effects with the markers utilized in each cycle of selection based on the previously revised estimates of QTL allele effects. This monitoring process results in significant overall improvements in efficiency of selection compared to Mapping Start Only approaches, especially where epistasis and/or genotype x environment interactions play a significant role in determining phenotype.

Additionally, the process can be performed by updating selectively over a subset (or window) of the breeding cycles. For example, where updating is performed by combining estimates of QTL effects, the population data included for purposes of generating a combined estimate of QTL effects can include a subset of the marker and phenotype data obtained from a selected window (designated for clarity by { }). Typically, the subset will include a contiguous series of cycles, such that in cases where the updating is performed each cycle, data from, e.g., {start and cycles 1, 2, 3, 4 and 5} can be included in the fifth cycle, data from {cycles 1, 2, 3, 4, 5, and 6} can be included at the 6$^{th}$ cycle, data from {cycles 2, 3, 4, 5, 6, and 7} at the 7$^{th}$ cycle, and the like. In circumstances where the updating is performed at a 3 cycle interval, the window can travel, e.g., in the following manner: {start}; {start and cycle 3}; {start, cycles 3 and 6}; {start, cycles 3, 6 and 9}; {cycles 3, 6, 9 and 12}; {cycles 6, 9, 12 and 15}; etc. Windows can be similarly determined by sequence regardless of the cycle interval. This offers two significant benefits. In the early stages of a breeding program, e.g., the first five or so cycles, little improvement is observed between Mapping As-You-Go and Mapping Start Only approaches, thus, in many cases, the additional expense of Mapping As-You-Go may not be warranted. Secondly, as the constituent populations change, i.e., as the germplasm evolves, throughout the breeding process, sliding the window forward with sequential cycles of breeding eliminates (or reduces) the bias in the estimates of QTL effects introduced at the start of the breeding program.

Using an approach that combines estimates over several cycles of the breeding program is also an effective way to account for the effects of gene-by-environment interactions. In this case, the Mapping As-You-Go method accumulates information on QTL effects in different types of environment that are sampled over cycles of the breeding program (i.e., year/location combinations). Thus, progress in the target set of environments defined by the scope of the breeding program can be more efficient by taking into consideration the QTL effects for the individual environment types. One way to implement this approach is to conduct selection on a weighted index of QTL information using estimates from previously sampled environments, where the weights that are used are based on the frequency of occurrence of environment types in the target population of environments (e.g., according to the methods described in Podlich et al. (1999) *Plant Breeding* 118:17-28).

The estimation of QTL effects does not necessarily need to be tied to the breeding population as a whole. For example, estimates of QTL allele effects can be considered on an individual cross basis, where each estimate is confined to a single cross between two elite lines. MAS selection is then conducted within each cross separately, based on the QTL effects estimated from each individual cross. A new set of estimates is used when selected lines form the basis of the next round of crossing.

The appropriateness of any of these variants to the Mapping As-You-Go approach depends largely on the extent to which epistasis and gene-by-environment interactions influence the genetic architecture of the trait of interest. Given their potential for impact on response to selection, empirical investigations to quantify the importance of epistasis and gene-by-environment interactions for trait phenotypes is considered to be an important component of the design and optimization of any MAS strategy.

The methods of the present invention for monitoring QTL effects and MAS are applicable to essentially any plant population or species. Preferred plants include agronomically and horticulturally important species. Such species include dicots, e.g., of the families: Leguminosae (including pea, beans, lentil, peanut, yam bean, cowpeas, velvet beans, soybean, clover, alfalfa, lupine, vetch, lotus, sweet clover, wisteria, and sweetpea); and, Compositae (the largest family of vascular plants, including at least 1,000 genera, including important commercial crops such as sunflower), Linaceae (e.g., flax), and Cruciferae (such as *Brassica napa*, i.e., rape or "Canola") as well as monocots including common grains, such as corn, wheat, rice, rye, triticale, millet, oats, and sorghum. It will be appreciated that the lists of commercially preferred plant species are intended to be exemplary, and are not intended to in any way limit application of the methods of the invention, which are applicable to any species of plant capable of sexual reproduction.

Additionally, exemplary plants, as well as those specified above, include plants from the genera: *Agrostis, Allium, Antirrhinum, Apium, Arachis, Asparagus, Atropa, Avena* (e.g., oats), *Bambusa, Brassica, Bromus, Browaalia, Camellia, Cannabis, Capsicum, Cicer, Chenopodium, Chichorium, Citrus, Coffea, Coix, Cucumis, Curcubita, Cynodon, Dactylis, Datura, Daucus, Digitalis, Dioscorea, Elaeis, Eleusine, Festuca, Fragaria, Geranium, Glycine, Helianthus, Heterocallis, Hevea, Hordeum* (e.g., barley), *Hyoscyamus, Ipomoea, Lactuca, Lens, Lilium, Linum, Lolium, Lotus, Lycopersicon, Majorana, Malus, Mangifera, Manihot, Medicago, Nemesia, Nicotiana, Onobrychis, Oryza* (e.g., rice), *Panicum, Pelargonium, Pennisetum* (e.g., millet), *Petunia, Pisum, Phaseolus, Phleum, Poa, Prunus, Ranunculus, Raphanus, Ribes, Ricinus, Rubus, Saccharum, Salpiglossis, Secale* (e.g., rye), *Senecio, Setaria, Sinapis, Solanum, Sorghum, Stenotaphrum, Theobroma, Trifolium, Trigonella, Triticum* (e.g., wheat), *Vicia, Vigna, Vitis, Zea* (e.g., corn), and the Olyreae, the Pharoideae and many others. As noted, plants in the family Graminae are a particularly preferred target plants.

Common crop plants which are targets of the present invention include corn, rice, triticale, rye, cotton, soybean, sorghum, wheat, oats, barley, millet, sunflower, canola, peas, beans, lentils, peanuts, yam beans, cowpeas, velvet beans, clover, alfalfa, lupine, vetch, lotus and sweet clover.

It will be appreciated that plants positive for a marker of the invention can be selected and crossed according to any breeding protocol relevant to the particular breeding program. Accordingly, progeny can be generated from a selected plant by crossing the selected plant to one or more additional plants selected on the basis of the same marker or a different marker, e.g., a different marker for the same or a different phentoype of interest. Alternatively, a selected plant can be back crossed to one or both parents. Backcrossing is usually done for the purpose of introgressing one or a few loci from a donor parent into an otherwise desirable genetic background from the recurrent parent. The more cycles of backcrossing that are performed, the greater the genetic contribution of the recurrent parent to the resulting variety. A selected plant can also be outcrossed, e.g., to a plant or line not present in its genealogy. Such a plant can be selected from among a population subject to a prior round of analysis, or may be introduced into the breeding program de novo. A plant positive for a desired marker can also be self-crossed ("selfed") to create a true breeding line with the same genotype.

Detection of Marker Loci

Although the specific DNA sequences which encode proteins are generally well-conserved across a species, regions of DNA which are non-coding, or which encode proteins or portions of proteins which lack critical function, tend to accumulate mutations, and therefore, are variable between members of the same species. Such regions provide the basis for numerous molecular genetic markers. Markers identify alterations in the genome, which can be insertions, deletions, point mutations, recombination events, or the presence and sequence of transposable elements. Many molecular or genetic markers have been characterized in plant species of interest, and are known to those of skill in the art.

Molecular markers can be detected by numerous methods, well-established in the art (e.g., restriction fragment length polymorphisms, allele specific hybridization (ASH), amplified variable sequences, randomly amplified polymorphic DNA (RAPD), self-sustained sequence replication, simple sequence repeat (SSR), single nucleotide polymorphism (SNP), single-strand conformation polymorphisms (SSCP), amplified fragment length polymorphisms (AFLP) and isozyme markers).

The majority of genetic markers rely on one or more property of nucleic acids for their detection. For example, some techniques for detecting genetic markers utilize hybridization of a probe nucleic acid to nucleic acids corresponding to the genetic marker. Hybridization formats including but not limited to, solution phase, solid phase, mixed phase, or in situ hybridization assays. Markers which are restriction fragment length polymorphisms (RFLP), are detected by hybridizing a probe which is typically a sub-fragment (or a synthetic oligonucleotide corresponding to a sub-fragment) of the nucleic acid to be detected to restriction digested genomic DNA. The restriction enzyme is selected to provide restriction fragments of at least two alternative (or polymorphic) lengths in different individuals, and will often vary from line to line. Determining a (one or more) restriction enzyme that produces informative fragments for each cross is a simple procedure, well known in the art. After separation by length in an appropriate matrix (e.g., agarose) and transfer to a membrane (e.g., nitrocellulose, nylon), the labeled probe is hybridized under conditions which result in equilibrium binding of the probe to the target followed by removal of excess probe by washing.

Nucleic acid probes to the marker loci can be cloned and/or synthesized. Detectable labels suitable for use with nucleic acid probes include any composition detectable by spectroscopic, radioisotopic, photochemical, biochemical, immunochemical, electrical, optical or chemical means. Useful labels include biotin for staining with labeled streptavidin conjugate, magnetic beads, fluorescent dyes, radiolabels, enzymes, and colorimetric labels. Other labels include ligands that bind to antibodies labeled with fluorophores, chemiluminescent agents, and enzymes. Labeling markers is readily achieved such as by the use of labeled PCR primers to marker loci.

The hybridized probe is then detected using, most typically by autoradiography or other similar detection technique (e.g., fluorography, liquid scintillation counter, etc.). Examples of specific hybridization protocols are widely available in the art, see, e.g., Berger, Sambrook, Ausubel, cited in the section entitled "GENERAL MOLECULAR BIOLOGY REFERENCES."

Amplified variable sequences refer to amplified sequences of the plant genome which exhibit high nucleic acid residue variability between members of the same species, e.g., microsatellite sequences. All organisms have variable genomic sequences and each organism (with the exception of a clone) has a different set of variable sequences. Once identified, the presence of specific variable sequences can be used to predict phenotypic traits. Preferably, DNA from the plant serves as a template for amplification with primers that flank a variable sequence of DNA. The variable sequence is amplified and then sequenced.

Randomly amplified polymorphic DNA (RAPD) markers are genomic sequences amplified by PCR using a single short primer of arbitrary sequence at low stringency. During amplification at low stringency a number of PCR products, some of which differ in length (and sequence) between individuals, are generated from random locations throughout the genome. Unlike amplified variable sequences, no prior sequence information is required to identify RAPD markers.

In vitro amplification techniques are well known in the art. Examples of techniques sufficient to direct persons of skill through such in vitro methods, including the polymerase chain reaction (PCR), the ligase chain reaction (LCR), Qβ-replicase amplification and other RNA polymerase mediated techniques (e.g., NASBA), are found in Berger, Sambrook and Ausubel as well as Mullis et al. (1987) U.S. Pat. No. 4,683,202; *PCR Protocols, A Guide to Methods and Applications* (Innis et al., eds.) Academic Press Inc., San Diego Academic Press Inc. San Diego, Calif. (1990) (Innis); Arnheim & Levinson (Oct. 1, 1990) *C&EN* 36-47; *The Journal Of NIH Research* (1991) 3, 81-94; (Kwoh et al. (1989) *Proc. Natl. Acad. Sci. USA* 86, 1173; Guatelli et al. (1990) *Proc. Natl. Acad. Sci. USA* 87, 1874; Lomell et al. (1989) *J. Clin. Chem* 35, 1826; Landegren et al., (1988) *Science* 241, 1077-1080; Van Brunt (1990) *Biotechnology* 8, 291-294; Wu and Wallace, (1989) *Gene* 4, 560; Barringer et al. (1990) *Gene* 89, 117, and Sooknanan and Malek (1995) *Biotechnology* 13: 563-564. Improved methods of cloning in vitro amplified nucleic acids are described in Wallace et al., U.S. Pat. No. 5,426,039. Improved methods of amplifying large nucleic acids by PCR are summarized in Cheng et al. (1994) *Nature* 369: 684, and the references therein, in which PCR amplicons of up to 40 kb are generated. One of skill will appreciate that essentially any RNA can be converted into a double stranded DNA suitable for restriction digestion, PCR expansion and sequencing using reverse transcriptase and a polymerase. See, Ausubel, Sambrook and Berger.

Oligonucleotides for use as primers, e.g., in amplification reactions and for use as nucleic acid sequence probes are typically synthesized chemically according to the solid phase phosphoramidite triester method described by Beaucage and Caruthers (1981) *Tetrahedron Lett.* 22:1859, or can simply be ordered commercially.

Alternatively, self-sustained sequence replication can be used to identify genetic markers. Self-sustained sequence replication refers to a method of nucleic acid amplification using target nucleic acid sequences which are replicated exponentially in vitro under substantially isothermal conditions by using three enzymatic activities involved in retroviral replication: (1) reverse transcriptase, (2) Rnase H, and (3) a DNA-dependent RNA polymerase (Guatelli et al. (1990) *Proc Natl Acad Sci USA* 87:1874). By mimicking the retroviral strategy of RNA replication by means of cDNA intermediates, this reaction accumulates cDNA and RNA copies of the original target.

Amplified restriction fragment polymorphisms or amplified fragment length polymorphisms (AFLP) can also be used as genetic markers (Vos et al. (1995) *Nucl Acids Res* 23:4407. The phrase "amplified restriction fragment polymorphism" refers to selected restriction fragments, which are amplified before or after cleavage by a restriction endonuclease. The amplification step allows easier detection of specific restriction fragments. AFLP allows the detection large numbers of polymorphic markers and has been used for genetic mapping of plants (Becker et al. (1995) *Mol Gen Genet* 249:65; and Meksem et al. (1995) *Mol Gen Genet* 249:74.

Allele-specific hybridization (ASH) can be used to identify the genetic markers of the invention. ASH technology is based on the stable annealing of a short, single-stranded, oligonucleotide probe to a completely complementary single-strand target nucleic acid. Detection is via an isotopic or non-isotopic label attached to the probe.

For each polymorphism, two or more different ASH probes are designed to have identical DNA sequences except at the polymorphic nucleotides. Each probe will have exact homology with one allele sequence so that the range of probes can distinguish all the known alternative allele sequences. Each probe is hybridized to the target DNA. With appropriate probe design and hybridization conditions, a single-base mismatch between the probe and target DNA will prevent hybridization. In this manner, only one of the alternative probes will hybridize to a target sample that is homozygous or homogenous for an allele. Samples that are heterozygous or heterogeneous for two alleles will hybridize to both of two alternative probes.

ASH markers are used as dominant markers where the presence or absence of only one allele is determined from hybridization or lack of hybridization by only one probe. The alternative allele may be inferred from the lack of hybridization. ASH probe and target molecules are optionally RNA or DNA; the target molecules are any length of nucleotides beyond the sequence that is complementary to the probe; the probe is designed to hybridize with either strand of a DNA target; the probe ranges in size to conform to variously stringent hybridization conditions, etc.

PCR allows the target sequence for ASH to be amplified from low concentrations of nucleic acid in relatively small volumes. Otherwise, the target sequence from genomic DNA is digested with a restriction endonuclease and size separated by gel electrophoresis. Hybridizations typically occur with the target sequence bound to the surface of a membrane or, as described in U.S. Pat. No. 5,468,613, the ASH probe sequence may be bound to a membrane.

In one embodiment, ASH data are obtained by amplifying nucleic acid fragments (amplicons) from genomic DNA using PCR, transferring the amplicon target DNA to a membrane in a dot-blot format, hybridizing a labeled oligonucleotide probe to the amplicon target, and observing the hybridization dots by autoradiography.

Single nucleotide polymorphisms (SNP) are markers that consist of a shared sequence differentiated on the basis of a single nucleotide. Typically, this distinction is detected by differential migration patterns of an amplicon comprising the SNP on e.g., an acrylamide gel. In such cases the marker may also be referred to as a single-strand conformation polymorphism or SSCP. However, alternative modes of detection, such as hybridization, e.g., ASH, or RFLP analysis are not excluded.

In yet another basis for providing a genetic linkage map, Simple sequence repeats (SSR), take advantage of high levels of di-, tri-, or tetra-nucleotide tandem repeats within a genome. Dinucleotide repeats have been reported to occur in the human genome as many as 50,000 times with n varying from 10 to 60 or more (Jacob et al. (1991) *Cell* 67:213. Dinucleotide repeats have also been found in higher plants (Condit and Hubbell (1991) *Genome* 34:66).

Briefly, SSR data is generated by hybridizing primers to conserved regions of the plant genome which flank the SSR sequence. PCR is then used to amplify the dinucleotide repeats between the primers. The amplified sequences are then electorphoresed to determine the size and therefore the number of di-, tri-, and tetra-nucleotide repeats.

Alternatively, isozyme markers are employed as genetic markers. Isozymes are multiple forms of enzymes that differ from one another in their amino acid, and therefore their nucleic acid sequences. Some isozymes are multimeric enzymes containing slightly different subunits. Other isozymes are either multimeric or monomeric but have been cleaved from the proenzyme at different sites in the amino acid sequence. Isozymes can be characterized and analyzed at the protein level, or alternatively, isozymes that differ at the nucleic acid level can be determined. In such cases any of the nucleic acid based methods described herein can be used to analyze isozyme markers.

In alternative embodiments, in silico methods can be used to detect the marker loci. For example, the sequence of a nucleic acid comprising the marker can be stored in a computer. The desired marker locus sequence or its homolog can be identified using an appropriate nucleic acid search algorithm as provided by, for example, in such readily available programs as BLAST.

Integrated Systems/Computer Assisted Methods

In one aspect of the invention, an integrated system such as a computer, software corresponding to the statistical models of the invention, and data sets corresponding to genetic markers and phenotypic values, facilitates mapping of phenotypic traits, including QTL. The phrase "integrated system" in the context of this invention refers to a system in which data entering a computer corresponds to physical objects or processes external to the computer, e.g., nucleic acid sequence hybridization, and a process that, within a computer, causes a physical transformation of the input signals to different output signals. In other words, the input data, e.g., hybridization on a specific region of an array is transformed to output data, e.g., the identification of the sequence hybridized. The process within the computer is a set of instructions, or "program," by which positive hybridization signals are recognized by the integrated system and attributed to individual samples as a genotype. Additional programs correlate the individual samples with phenotypic values, e.g., statistical methods as described herein. In particular, the integrated system is equipped with at least one instruction set useful for recursively updating estimates of QTL effects by replacing or combining an estimate of QTL effects with new and/or additional data correlating marker and phentoype. For example, the programs QTLCartographer® and MapQTL® are particularly suited to this type of analysis and can be extended to include the additional statistical methods described herein, e.g., HAPLO-MQM+ models. In addition there are numerous e.g., C/C++ programs for computing, Delphi and/or Java programs for GUI interfaces, and productivity tools (e.g., Microsoft Excel and/or SigmaPlot) for charting. Other useful software tools in the context of the integrated systems of the invention include statistical packages such as SAS, Genstat, Matlab, Mathematica, and S-Plus and genetic modeling packages such as QU-GENE. Furthermore additional programming languages such as Fortran and the like are also suitably employed in the integrated systems of the invention.

For example, phenotypic values assigned to a population of progeny descending from related or unrelated crosses are recorded in a computer readable medium, thereby establishing a database corresponding phenotypic values with unique identifiers for each member of the population of progeny. Any file or folder, whether custom-made or commercially available (e.g., from Oracle or Sybase) suitable for recording data in a computer readable medium is acceptable as a database in the context of the present invention. Data regarding genotype for one or more molecular markers, e.g., RFLP, AFLP, RAPD, ASH, SSR, SNP, isozyme markers or other markers as described herein, are similarly recorded in a computer accessible database. Optionally, marker data is obtained using an integrated system that automates one or more aspects of the assay (or assays) used to determine marker(s) genotype. In such a system, input data corresponding to genotypes for molecular markers are relayed from a device, e.g., an array, a scanner, a CCD, or other detection device directly to files in a computer readable medium accessible to the central processing unit. A set of instructions (embodied in one or more programs) encoding the statistical models of the invention is then executed by the computational device to identify correlations between phenotypic values and marker genotypes. Typically, the integrated system also includes a user input device, such as a keyboard, a mouse, a touchscreen, or the like, for, e.g., selecting files, retrieving data, etc., and an output device (e.g., a monitor, a printer, etc.) for viewing or recovering the product of the statistical analysis.

Thus, in one aspect, the invention provides an integrated system comprising a computer or computer readable medium comprising set of files and/or a database with at least one data set that corresponds to genotypes for genetic markers. The system also includes a user interface allowing a user to selectively view one or more databases. In addition, standard text manipulation software such as word processing software (e.g., Microsoft Word™ or Corel Wordperfect™) and database or spreadsheet software (e.g., spreadsheet software such as Microsoft Excel™, Corel Quattro Pro™, or database programs such as Microsoft Access™ or Paradox™) can be used in conjunction with a user interface (e.g., a GUI in a standard operating system such as a Windows, Macintosh, Unix or Linux system) to manipulate strings of characters.

The invention also provides integrated systems for sample manipulation incorporating robotic devices as previously described. A robotic liquid control armature for transferring solutions (e.g., plant cell extracts) from a source to a destination, e.g., from a microtiter plate to an array substrate, is optionally operably linked to the digital computer (or to an additional computer in the integrated system). An input device for entering data to the digital computer to control high throughput liquid transfer by the robotic liquid control armature and, optionally, to control transfer by the armature to the solid support is commonly a feature of the integrated system.

Integrated systems for molecular marker analysis of the present invention typically include a digital computer with one or more of high-throughput liquid control software, image analysis software, data interpretation software, a robotic liquid control armature for transferring solutions from a source to a destination operably linked to the digital computer, an input device (e.g., a computer keyboard) for entering data to the digital computer to control high throughput liquid transfer by the robotic liquid control armature and, optionally, an image scanner for digitizing label signals from labeled probes hybridized, e.g., to expression products on a solid support operably linked to the digital computer. The image scanner interfaces with the image analysis software to provide a measurement of, e.g., differentiating nucleic acid probe label intensity upon hybridization to an arrayed sample nucleic acid population, where the probe label intensity measurement is interpreted by the data interpretation software to show whether, and to what degree, the labeled probe hybridizes to a label. The data so derived is then correlated with phenotypic values using the statistical models of the present invention, to determine the correspondence between phenotype and genotype(s) for genetic markers, thereby, assigning chromosomal locations and estimated effects for QTL.

Optical images, e.g., hybridization patterns viewed (and, optionally, recorded) by a camera or other recording device (e.g., a photodiode and data storage device) are optionally further processed in any of the embodiments herein, e.g., by digitizing the image and/or storing and analyzing the image on a computer. A variety of commercially available peripheral equipment and software is available for digitizing, storing and analyzing a digitized video or digitized optical image, e.g., using PC (Intel x86 or Pentium chip-compatible DOS™, OS2™ WINDOWS™, WINDOWS NT™ or WINDOWS95™ based machines), MACINTOSH™, LINUX, or UNIX based (e.g., SUN™ work station) computers.

Positional Cloning of QTL

"Positional gene cloning" uses the proximity of a genetic marker to physically define a cloned chromosomal fragment that is linked to a QTL identified using the statistical methods of the invention. Clones of nucleic acids linked to QTL have a variety of uses, including as genetic markers for identification of additional QTL in subsequent applications of marker assisted selection (MAS). Markers which are adjacent to an open reading frame (ORF) associated with a phenotypic trait can hybridize to a DNA clone, thereby identifying a clone on which an ORF is located. If the marker is more distant, a fragment containing the open reading frame is identified by successive rounds of screening and isolation of clones which together comprise a contiguous sequence of DNA, a "contig." Protocols sufficient to guide one of skill through the isolation of clones associated with linked markers are found in, e.g., in the references cited in the section entitled "GENERAL MOLECULAR BIOLOGY REFERENCES" below.

For example, "Positional gene cloning" uses the proximity of a genetic marker to physically define an isolated chromosomal fragment that is linked to a QTL. The isolated chromosomal fragment can be produced by such well known methods as digesting chromosomal DNA with one or more restriction enzymes, or by amplifying a chromosomal region in a polymerase chain reaction (PCR), or alternative amplification reaction. The digested or amplified fragment is typically ligated into a vector suitable for replication, e.g., a plasmid, a cosmid, a phage, an artificial chromosome, or the like, and, optionally expression, of the inserted fragment. Markers which are adjacent to an open reading frame (ORF) associated with a phenotypic trait can hybridize to a DNA clone, thereby identifying a clone on which an ORF is located. If the marker is more distant, a fragment containing the open reading frame is identified by successive rounds of screening and isolation of clones which together comprise a contiguous sequence of DNA, a "contig." Protocols sufficient to guide one of skill through the isolation of clones associated with linked markers are found in, e.g. Berger, Sambrook and Ausubel, all supra.

Similarly, nucleic acids comprising a chromosome interval including a QTL identified according to the methods of the present invention can also be isolated and/or cloned. The QTL is localized within a chromosome interval defined by QTL markers, wherein each marker flanks and is genetically linked to the QTL. Such intervals can be utilized to identify homologous nucleic acids and/or can be used in the production of transgenic plants with desirable phenotypic attributes conferred by the introduced QTL. A chromosome interval comprising a QTL is isolated, e.g., cloned via positional cloning methods outlined above. A chromosome interval can contain one or more ORFs associated with the desired phenotypic trait, and can be cloned on one or more individual vectors, e.g., depending on the size of the chromosome interval.

It will be appreciated that numerous vectors are available in the art for the isolation and replication of the nucleic acids of the invention. For example, plasmids, cosmids and phage vectors are well known in the art, and are sufficient for many applications (e.g., in applications involving insertion of nucleic acids ranging from less than 1 to about 20 kilobases (kb)). In certain applications, it is advantageous to make or clone large nucleic acids to identify nucleic acids more distantly linked to a given marker, or to isolate nucleic acids in excess of 10-20 kb, e.g., up to several hundred kilobases or more, such as the entire interval between two linked markers, i.e., up to and including one or more centiMorgans (cM), linked to QTL as identified herein. In such cases, a number of vectors capable of accommodating large nucleic acids are available in the art, these include, yeast artificial chromosomes (YACs), bacterial artificial chromosomes (BACs), plant artificial chromosomes (PACs) and the like. For a general introduction to YACs, BACs, PACs and MACs as artificial chromosomes, see, e.g., Monaco and Larin (1994) *Trends Biotechnol* 12:280. In addition, methods for the in vitro amplification of large nucleic acids linked to genetic markers are widely available (e.g., Cheng et al. (1994) *Nature* 369: 684, and references therein). Cloning systems can be created or obtained from commercially; see, for example, Stratagene Cloning Systems, Catalogs 2000 (La Jolla, Calif.).

Vectors, Promoters and Expression Systems

The present invention includes recombinant constructs incorporating one or more of the nucleic acid sequences described above. Such constructs include a vector, for example, a plasmid, a cosmid, a phage, a virus, a bacterial artificial chromosome (BAC), a yeast artificial chromosome (YAC), etc., into which one or more polynucleotide sequences of interest (e.g., a QTL marker or QTL) has been inserted, in a forward or reverse orientation. For example, the inserted nucleic acid can include a chromosomal sequence or cDNA including all or part of at least one QTL or open reading frame ("ORF") associated with a QTL or QTL marker. In a preferred embodiment, the construct further comprises regulatory sequences, including, for example, a promoter, operably linked to the sequence. Large numbers of suitable vectors and promoters are known to those of skill in the art, and are commercially available.

As desired, the polynucleotides of the present invention, e.g., a QTL identified according to the methods described herein, can be included in any one of a variety of vectors suitable for generating sense or antisense RNA, and optionally, polypeptide expression products. Such vectors include chromosomal, nonchromosomal and synthetic DNA sequences, e.g., derivatives of SV40; bacterial plasmids; phage DNA; baculovirus; yeast plasmids; vectors derived from combinations of plasmids and phage DNA, viral DNA such as vaccinia, adenovirus, fowl pox virus, pseudorabies, adenovirus, adeno-associated virus, retroviruses and many others. Any vector that is capable of introducing genetic material into a cell, and, if replication is desired, which is replicable in the relevant host can be used.

In an expression vector or expression cassette, the polynucleotide sequence of interest is physically arranged in proximity and orientation to an appropriate transcription control sequence (promoter, and optionally, one or more enhancers) to direct mRNA synthesis. That is, the polynucleotide sequence of interest is "operably linked" to an appropriate transcription control sequence. Examples of such promoters include: LTR or SV40 promoter, *E. coli* lac or trp promoter, phage lambda $P_L$ promoter, and other promoters known to control expression of genes in prokaryotic or eukaryotic cells or their viruses. The expression vector also contains a ribosome binding site for translation initiation, and a transcription terminator. The vector optionally includes appropriate sequences for amplifying expression. In addition, the expression vectors optionally comprise one or more selectable marker genes to provide a phenotypic trait for selection of transformed host cells, such as dihydrofolate reductase or neomycin resistance for eukaryotic cell culture, or such as tetracycline or ampicillin resistance in *E. coli*.

Additional Expression Elements

Where translation of polypeptide encoded by a nucleic acid comprising a polynucleotide sequence of the invention is desired, additional translation specific initiation signals can improve the efficiency of translation. These signals can include, e.g., an ATG initiation codon and adjacent sequences. In some cases, for example, full-length cDNA molecules or chromosomal segments including a coding sequence incorporating, e.g., a QTL or an ORF associated with a QTL or QTL marker, a translation initiation codon and associated sequence elements are inserted into the appropriate expression vector simultaneously with the polynucleotide sequence of interest. In such cases, additional translational control signals frequently are not required. However, in cases where only a polypeptide coding sequence, or a portion thereof, is inserted, exogenous translational control signals, including an ATG initiation codon must be provided. Furthermore, the initiation codon must be in the correct reading frame to ensure transcription of the polynucleotide sequence of interest. Exogenous transcriptional elements and initiation codons can be of various origins, both natural and synthetic. The efficiency of expression can be enhanced by the inclusion of enhancers appropriate to the cell system in use (Scharf D et al. (1994) *Results Probl Cell Differ* 20:125-62; Bittner et al. (1987) *Methods in Enzymol* 153:516-544).

Generation of Transgenic Plants and Cells

The present invention also relates to host cells and organisms which are transformed with nucleic acids corresponding to QTL and other genes identified according to the methods of the invention. For example, such nucleic acids include chromosome intervals, ORFs, and/or cDNAs or corresponding to a sequence or subsequence included within the identified chromosome interval or ORF. Additionally, the invention provides for the production of polypeptides corresponding to QTL by recombinant techniques. Host cells are genetically engineered (i.e., transduced, transfected or transformed) with the vectors of this invention (i.e., vectors which comprise QTL or other nucleic acids identified according to the methods of the invention and as described above) which are, for example, a cloning vector or an expression vector. Such vectors include, in addition to those described above, e.g., an *agrobacterium*, a virus (such as a plant virus), a naked polynucleotide, or a conjugated polynucleotide. The vectors are introduced into plant tissues, cultured plant cells or plant protoplasts by a variety of standard methods including electroporation (From et al. (1985) *Proc. Natl. Acad. Sci. USA* 82;5824), infection by viral vectors such as cauliflower mosaic virus (CaMV) (Hohn et al. (1982) *Molecular Biology of Plant Tumors* (Academic Press, New York, pp. 549-560; Howell U.S. Pat. No. 4,407,956), high velocity ballistic penetration by small particles with the nucleic acid either within the matrix of small beads or particles, or on the surface (Klein et al. (1987) *Nature* 327;70), use of pollen as vector (WO 85/01856), or use of *Agrobacterium tumefaciens* or *A. rhizogenes* carrying a T-DNA plasmid in which DNA fragments are cloned. The T-DNA plasmid is transmitted to plant cells upon infection by *Agrobacterium tumefaciens*, and a portion is stably integrated into the plant genome (Horsch et al. (1984) *Science* 233;496; Fraley et al. (1983)*Proc. Natl. Acad. Sci. USA* 80;4803). The method of introducing a nucleic acid of the present invention into a host cell is not critical to the present invention. Thus, any method, e.g., including but not limited to the above examples, which provides for effective introduction of a nucleic acid into a cell or protoplast can be employed.

The engineered host cells can be cultured in conventional nutrient media modified as appropriate for such activities as, for example, activating promoters or selecting transformants. These cells can optionally be cultured into transgenic plants. Plant regeneration from cultured protoplasts is described in Evans et al. (1983) "Protoplast Isolation and Culture," *Handbook of Plant Cell Cultures* 1, 124-176 (MacMillan Publishing Co., New York; Davey (1983) "Recent Developments in the Culture and Regeneration of Plant Protoplasts," *Protoplasts*, pp. 12-29, (Birkhauser, Basel); Dale (1983) "Protoplast Culture and Plant Regeneration of Cereals and Other Recalcitrant Crops," *Protoplasts* pp. 31-41, (Birkhauser, Basel); Binding (1985) "Regeneration of Plants," *Plant Protoplasts*, pp. 21-73, (CRC Press, Boca Raton,).

The present invention also relates to the production of transgenic organisms, which may be bacteria, yeast, fungi, or plants, transduced with the nucleic acids, e.g., cloned QTL of the invention. A thorough discussion of techniques relevant to bacteria, unicellular eukaryotes and cell culture may be found in references enumerated above and are briefly outlined as follows. Several well-known methods of introducing target nucleic acids into bacterial cells are available, any of which may be used in the present invention. These include: fusion of the recipient cells with bacterial protoplasts containing the DNA, treatment of the cells with liposomes containing the DNA, electroporation, projectile bombardment (biolistics), carbon fiber delivery, and infection with viral vectors (discussed further, below), etc. Bacterial cells can be used to amplify the number of plasmids containing DNA constructs of this invention. The bacteria are grown to log phase and the plasmids within the bacteria can be isolated by a variety of methods known in the art (see, for instance, Sambrook). In addition, numerous kits are commercially available and can be employed according to the manufacturers instructions for the purification of plasmids from bacteria (and other cells). For their proper use, follow the manufacturer's instructions (see, for example, EasyPrep™, FlexiPrep™, both from Pharmacia Biotech; StrataClean™, from Stratagene; and, QIAprep™ from Qiagen). The isolated and purified plasmids are then further manipulated to produce other plasmids, used to transfect plant cells or incorporated into *Agrobacterium tumefaciens* related vectors to infect plants. Typical vectors contain transcription and translation terminators, transcription and translation initiation sequences, and promoters useful for regulation of the expression of the particular target nucleic acid.

The vectors optionally comprise generic expression cassettes containing at least one independent terminator sequence, sequences permitting replication of the cassette in eukaryotes, or prokaryotes, or both, (e.g., shuttle vectors) and selection markers for both prokaryotic and eukaryotic systems. Vectors are suitable for replication and integration in prokaryotes, eukaryotes, or preferably both. See, Giliman & Smith (1979) *Gene* 8:81; Roberts et al. (1987) *Nature* 328: 731; Schneider et al. (1995) *Protein Expr. Purif.* 6435:10; Ausubel, Sambrook, Berger (all supra). A catalogue of Bacteria and Bacteriophages useful for cloning is provided, e.g., by the ATCC, e.g., *The ATCC Catalogue of Bacteria and Bacteriophage* (1992) Gherna et al. (eds) published by the ATCC. Additional basic procedures for sequencing, cloning and other aspects of molecular biology and underlying theoretical considerations are also found in Watson et al. (1992) *Recombinant DNA*, Second Edition, Scientific American Books, N.Y.

Transforming Nucleic Acids into Plants

Embodiments of the present invention pertain to the production of transgenic plants comprising the cloned nucleic acids, e.g., chromosome intervals, isolated ORFs, and cDNAs associated with QTL, of the invention. Techniques for transforming plant cells with nucleic acids are generally available and can be adapted to the invention by the use of nucleic acids encoding or corresponding to QTL, QTL homologs, isolated chromosome intervals, and the like. In addition to Berger, Ausubel and Sambrook (infra), useful general references for plant cell cloning, culture and regeneration include Jones (ed) (1995) *Plant Gene Transfer and Expression Protocols—Methods in Molecular Biology, Volume* 49 Humana Press Towata N.J.; Payne et al. (1992) *Plant Cell and Tissue Culture in Liquid Systems* John Wiley & Sons, Inc. New York, N.Y. (Payne); and Gamborg and Phillips (eds) (1995) *Plant Cell, Tissue and Organ Culture: Fundamental Methods* Springer Lab Manual, Springer-Verlag (Berlin Heidelberg New York) (Gamborg). A variety of cell culture media are described in Atlas and Parks (eds) *The Handbook of Microbiological Media* (1993) CRC Press, Boca Raton, Fla. (Atlas). Additional information for plant cell culture is found in available commercial literature such as the *Life Science Research Cell Culture Catalogue* (1998) from Sigma-Aldrich, Inc (St Louis, Mo.) (Sigma-LSRCCC) and, e.g., the *Plant Culture Catalogue* and supplement (1997) also from Sigma-Aldrich, Inc (St Louis, Mo.) (Sigma-PCCS). Additional details regarding plant cell culture are found in Croy, (ed.) (1993) *Plant Molecular Biology* Bios Scientific Publishers, Oxford, U.K.

The nucleic acid constructs of the invention, e.g., plasmids, cosmids, artificial chromosomes, DNA and RNA polynucleotides, are introduced into plant cells, either in culture or in the organs of a plant by a variety of conventional techniques. Where the sequence is expressed, the sequence is optionally combined with transcriptional and translational initiation regulatory sequences which direct the transcription or translation of the sequence from the exogenous DNA in the intended tissues of the transformed plant.

Isolated nucleic acids can be introduced into plants according to any of a variety of techniques known in the art. Techniques for transforming a wide variety of higher plant species are well known and described in the technical, scientific, and patent literature. See, for example, Weising et al. (1988) *Ann. Rev. Genet.* 22:421-477.

For example plasmids, cosmids, phage, naked or variously conjugated-DNA polynucleotides, (e.g., polylysine-conjugated DNA, peptide-conjugated DNA, liposome-conjugated DNA, etc.), or artificial chromosomes, can be introduced directly into the genomic DNA of the plant cell using techniques such as electroporation and microinjection of plant cell protoplasts, or the DNA constructs can be introduced directly to plant cells using ballistic methods, such as DNA particle bombardment.

Microinjection techniques for injecting e.g., cells, embryos, callus and protoplasts, are known in the art and well described in the scientific and patent literature. For example, a number of methods are described in Jones (ed) (1995) *Plant Gene Transfer and Expression Protocols—Methods in Molecular Biology, Volume* 49 Humana Press Towata N.J., as well as in the other references noted herein and available in the literature.

For example, the introduction of DNA constructs using polyethylene glycol precipitation is described in Paszkowski, et al., *EMBO J.* 3:2717 (1984). Electroporation techniques are described in Fromm, et al., *Proc. Nat'l. Acad. Sci. USA* 82:5824 (1985). Ballistic transformation techniques are described in Klein, et al., *Nature* 327:70-73 (1987). Additional details are found in Jones (1995) and Gamborg and Phillips (1995), supra, and in U.S. Pat. No. 5,990,387.

Alternatively, and in some cases preferably, *Agrobacterium* mediated transformation is employed to generate transgenic plants. *Agrobacterium*-mediated transformation techniques, including disarming and use of binary vectors, are also well described in the scientific literature. See, for example Horsch, et al. (1984) *Science* 233:496; and Fraley et al. (1984) *Proc. Nat'l. Acad. Sci. USA* 80:4803 and recently reviewed in Hansen and Chilton (1998) *Current Topics in Microbiology* 240:22 and Das (1998) *Subcellular Biochemistry* 29: Plant Microbe Interactions pp343-363.

The DNA constructs may be combined with suitable T-DNA flanking regions and introduced into a conventional *Agrobacterium tumefaciens* host vector. The virulence functions of the *Agrobacterium tumefaciens* host will direct the insertion of the construct and adjacent marker into the plant cell DNA when the cell is infected by the bacteria. See, U.S. Pat. No. 5,591,616. Although *Agrobacterium* is useful primarily in dicots, certain monocots can be transformed by *Agrobacterium*. For instance, *Agrobacterium* transformation of maize is described in U.S. Pat. No. 5,550,318.

Other methods of transfection or transformation include (1) *Agrobacterium rhizogenes*-mediated transformation (see, e.g., Lichtenstein and Fuller (1987) In: *Genetic Engineering*, vol. 6, PWJ Rigby, Ed., London, Academic Press; and Lichtenstein; C. P., and Draper (1985) In: *DNA Cloning*, Vol. II, D. M. Glover, Ed., Oxford, IRI Press; WO 88/02405, published Apr. 7, 1988, describes the use of *A. rhizogenes* strain A4 and its R1 plasmid along with *A. tumefaciens* vectors pARC8 or pARC16 (2) liposome-mediated DNA uptake (see, e.g., Freeman et al. (1984) *Plant Cell Physiol.* 25:1353), (3) the vortexing method (see, e.g., Kindle (1990) *Proc. Natl. Acad. Sci., (USA)* 87:1228.

DNA can also be introduced into plants by direct DNA transfer into pollen as described by Zhou et al. (1983) *Methods in Enzymology*, 101:433; D. Hess (1987) *Intern Rev. Cytol.* 107:367; Luo et al. (1988) *Plant Mol. Biol. Reporter* 6:165. Expression of polypeptide coding genes can be obtained by injection of the DNA into reproductive organs of a plant as described by Pena et al. (1987) *Nature* 325:274. DNA can also be injected directly into the cells of immature embryos and the desiccated embryos rehydrated as described by Neuhaus et al.(1987) *Theor. Appl. Genet.* 75:30; and Benbrook et al.(1986) in *Proceedings Bio Expo* Butterworth, Stoneham, Mass., pp. 27-54. Additionally, a variety of plant viruses that can be employed as vectors are known in the art and include cauliflower mosaic virus (CaMV), geminivirus, brome mosaic virus, and tobacco mosaic virus.

Regeneration of Transgenic Plants

Transformed plant cells which are derived by any of the above transformation techniques can be cultured to regenerate a whole plant which possesses the transformed genotype and thus the desired phenotype. Such regeneration techniques rely on manipulation of certain phytohormones in a tissue culture growth medium, typically relying on a biocide and/or herbicide marker which has been introduced together with the desired nucleotide sequences. Plant regeneration from cultured protoplasts is described in Evans et al. (1983) *Protoplasts Isolation and Culture, Handbook of Plant Cell Culture* pp. 124-176, Macmillian Publishing Company, New York; and Binding (1985) *Regeneration of Plants, Plant Protoplasts* pp. 21-73, CRC Press, Boca Raton. Regeneration can also be obtained from plant callus, explants, somatic embryos (Dandekar et al. (1989) *J. Tissue Cult. Meth.* 12:145; McGranahan, et al. (1990) *Plant Cell Rep.* 8:512) organs, or parts thereof. Such regeneration techniques are described generally in Klee et al. (1987)., *Ann. Rev. of Plant Phys.* 38:467-486. Additional details are found in Payne (1992) and Jones (1995), both supra, and Weissbach and Weissbach, eds.(1988) *Methods for Plant Molecular Biology* Academic Press, Inc., San Diego, Calif. This regeneration and growth process includes the steps of selection of transformant cells and shoots, rooting the transformant shoots and growth of the plantlets in soil. These methods are adapted to the invention to produce transgenic plants bearing QTL and other genes isolated according to the methods of the invention.

In addition, the regeneration of plants containing the polynucleotide of the present invention and introduced by *Agrobacterium* into cells of leaf explants can be achieved as described by Horsch et al. (1985) *Science* 227:1229-1231. In this procedure, transformants are grown in the presence of a selection agent and in a medium that induces the regeneration of shoots in the plant species being transformed as described by Fraley et al. (1983) *Proc. Natl. Acad. Sci.* (U.S.A.) 80:4803. This procedure typically produces shoots within two to four weeks and these transformant shoots are then transferred to an appropriate root-inducing medium containing the selective agent and an antibiotic to prevent bacterial growth. Transgenic plants of the present invention may be fertile or sterile.

In construction of recombinant expression cassettes of the invention, which include, for example, an ORF associated with a QTL or QTL marker, a plant promoter fragment is optionally employed which directs expression of a nucleic acid in any or all tissues of a regenerated plant. Examples of constitutive promoters include the cauliflower mosaic virus (CaMV) 35S transcription initiation region, the 1'- or 2'-promoter derived from T-DNA of *Agrobacterium tumefaciens*, and other transcription initiation regions from various plant genes known to those of skill. Alternatively, the plant promoter may direct expression of the polynucleotide of the invention in a specific tissue (tissue-specific promoters) or may be otherwise under more precise environmental control (inducible promoters). Examples of tissue-specific promoters under developmental control include promoters that initiate transcription only in certain tissues, such as fruit, seeds, or flowers.

Any of a number of promoters which direct transcription in plant cells can be suitable. The promoter can be either constitutive or inducible. In addition to the promoters noted above, promoters of bacterial origin which operate in plants include the octopine synthase promoter, the nopaline synthase promoter and other promoters derived from native Ti plasmids. See, Herrara-Estrella et al. (1983), *Nature,* 303: 209. Viral promoters include the 35S and 19 S RNA promoters of cauliflower mosaic virus. See, Odell et al. (1985) *Nature,* 313:810. Other plant promoters include the ribulose-1,3-bisphosphate carboxylase small subunit promoter and the phaseolin promoter. The promoter sequence from the E8 gene and other genes may also be used. The isolation and sequence of the E8 promoter is described in detail in Deikman and Fischer (1988) *EMBO J.* 7:3315. Many other promoters are in current use and can be coupled to an exogenous DNA sequence to direct expression of the nucleic acid.

If expression of a polypeptide, including those encoded by QTL or other nucleic acid, is desired, a polyadenylation region at the 3'-end of the coding region is typically included. The polyadenylation region can be derived from the natural gene, from a variety of other plant genes, or from, e.g., T-DNA.

The vector comprising the sequences (e.g., promoters or coding regions) from genes encoding expression products and transgenes of the invention will typically include a nucleic acid subsequence, a marker gene which confers a selectable, or alternatively, a screenable, phenotype on plant cells. For example, the marker may encode biocide tolerance, particularly antibiotic tolerance, such as tolerance to kanamycin, G418, bleomycin, hygromycin, or herbicide tolerance, such as tolerance to chlorosluforon, or phosphinothricin (the active ingredient in the herbicides bialaphos or Basta). See, e.g., Padgette et al. (1996) In: *Herbicide-Resistant Crops* (Duke, ed.), pp 53-84, CRC Lewis Publishers, Boca Raton ("Padgette, 1996"). For example, crop selectivity to specific herbicides can be conferred by engineering genes into crops which encode appropriate herbicide metabolizing enzymes from other organisms, such as microbes. See, Vasil (1996) In: *Herbicide-Resistant Crops* (Duke, ed.), pp 85-91, CRC Lewis Publishers, Boca Raton) ("Vasil", 1996).

One of skill will recognize that after the recombinant expression cassette is stably incorporated in transgenic plants and confirmed to be operable, it can be introduced into other plants by sexual crossing. Any of a number of standard breeding techniques can be used, depending upon the species to be crossed. In vegetatively propagated crops, mature transgenic plants can be propagated by the taking of cuttings or by tissue culture techniques to produce multiple identical plants. Selection of desirable transgenics is made and new varieties are obtained and propagated vegetatively for commercial use. In seed propagated crops, mature transgenic plants can be self crossed to produce a homozygous inbred plant. The inbred plant produces seed containing the newly introduced heterologous nucleic acid. These seeds can be grown to produce plants that would produce the selected phenotype. Parts obtained from the regenerated plant, such as flowers, seeds, leaves, branches, fruit, and the like are included in the invention, provided that these parts comprise cells comprising the isolated nucleic acid of the present invention. Progeny and variants, and mutants of the regenerated plants are also included within the scope of the invention, provided that these parts comprise the introduced nucleic acid sequences.

Transgenic plants expressing a polynucleotide of the present invention can be screened for transmission of the nucleic acid of the present invention by, for example, standard immunoblot and DNA detection techniques. Expression at the RNA level can be determined initially to identify and quantitate expression-positive plants. Standard techniques for RNA analysis can be employed and include PCR amplification assays using oligonucleotide primers designed to amplify only the heterologous RNA templates and solution hybridization assays using heterologous nucleic acid-specific probes. The RNA-positive plants can then analyzed for protein expression by Western immunoblot analysis using the specifically reactive antibodies of the present invention. In addition, in situ hybridization and immunocytochemistry according to standard protocols can be done using heterologous nucleic acid specific polynucleotide probes and antibodies, respectively, to localize sites of expression within transgenic tissue. Generally, a number of transgenic lines are usually screened for the incorporated nucleic acid to identify and select plants with the most appropriate expression profiles.

A preferred embodiment is a transgenic plant that is homozygous for the added heterologous nucleic acid; i.e., a transgenic plant that contains two added nucleic acid sequences, one gene at the same locus on each chromosome of a chromosome pair. A homozygous transgenic plant can be obtained by sexually mating (selfing) a heterozygous transgenic plant that contains a single added heterologous nucleic acid, germinating some of the seed produced and analyzing the resulting plants produced for altered expression of a polynucleotide of the present invention relative to a control plant (i.e., native, non-transgenic). Back-crossing to a parental plant and out-crossing with a non-transgenic plant are also contemplated.

General Molecular Biology References

In the context of the invention, e.g., identifying QTL markers and/or loci, monitoring selected QTL markers, cloning and isolation of ATL and other nucleic acids, etc., nucleic acids and/or proteins are manipulated according to well known molecular biology techniques. Detailed protocols for numerous such procedures are described in, e.g., in Ausubel et al. *Current Protocols in Molecular Biology* (supplemented through 2000) John Wiley & Sons, New York ("Ausubel"); Sambrook et al. *Molecular Cloning—A Laboratory Manual* (2nd Ed.), Vol. 1-3, Cold Spring Harbor Laboratory, Cold Spring Harbor, N.Y., 1989 ("Sambrook"), and Berger and Kimmel *Guide to Molecular Cloning Techniques, Methods in Enzymology* volume 152 Academic Press, Inc., San Diego, Calif. ("Berger").

In addition to the above references, protocols for in vitro amplification techniques, such as the polymerase chain reaction (PCR), the ligase chain reaction (LCR), Qβ-replicase amplification, and other RNA polymerase mediated techniques (e.g., NASBA), useful e.g., for amplifying cDNA probes of the invention, are found in Mullis et al. (1987) U.S. Pat. No. 4,683,202; *PCR Protocols A Guide to Methods and Applications* (Innis et al. eds) Academic Press Inc. San Diego, Calif. (1990) ("Innis"); Arnheim and Levinson (1990) *C&EN* 36; *The Journal Of NIH Research* (1991) 3:81; Kwoh et al. (1989) *Proc Natl Acad Sci USA* 86, 1173; Guatelli et al. (1990) *Proc Natl Acad Sci USA* 87:1874; Lomell et al. (1989) *J Clin Chem* 35:1826; Landegren et al. (1988) *Science* 241: 1077; Van Brunt (1990) *Biotechnology* 8:291; Wu and Wallace (1989) *Gene* 4: 560; Barringer et al. (1990) *Gene* 89:117, and Sooknanan and Malek (1995) *Biotechnology* 13:563. Additional methods, useful for cloning nucleic acids in the context of the present invention, include Wallace et al. U.S. Pat. No. 5,426,039. Improved methods of amplifying large nucleic acids by PCR are summarized in Cheng et al. (1994) *Nature* 369:684 and the references therein.

Certain polynucleotides of the invention, e.g., oligonucleotides can be synthesized utilizing various solid-phase strategies involving mononucleotide- and/or trinucleotide-based phosphoramidite coupling chemistry. For example, nucleic acid sequences can be synthesized by the sequential addition of activated monomers and/or trimers to an elongating polynucleotide chain. See e.g., Caruthers, M. H. et al. (1992) *Meth Enzymol* 211:3.

In lieu of synthesizing the desired sequences, essentially any nucleic acid can be custom ordered from any of a variety of commercial sources, such as The Midland Certified Reagent Company (mcrc@oligos.com), The Great American Gene Company (www.genco.com), ExpressGen, Inc. (www.expressgen.com), Operon Technologies, Inc. (www.operon.com), and many others.

Similarly, commercial sources for nucleic acid and protein microarrays are available, and include, e.g., Affymetrix, Santa Clara, Calif. (http://www.affymetrix.com/); and Incyte, Palo Alto, Calif. (http://www.incyte.com); and Ciphergen Biosciences, Fremont, Calif. (http://www.ciphergen.com/).

High Throughput Screening

In one aspect of the invention, the determination of genetic marker alleles is performed by high throughput screening. High throughput screening involves providing a library of genetic markers, e.g., RFLPs, AFLPs, isozymes, specific alleles and variable sequences, including SSR, RAPD and the like. Such libraries are then screened against plant genomes to generate a "fingerprint" for each plant under consideration. In some cases a partial fingerprint comprising a sub-portion of the markers is generated in an area of interest. Once the genetic marker alleles of a plant have been identified, the correspondence between one or several of the marker alleles and a desired phenotypic trait is determined through statistical associations based on the methods of this invention.

High throughput screening can be performed in many different formats. Hybridization can take place in a 96-, 324-, or a 1524-well format or in a matrix on a silicon chip or other format.

In one commonly used format, a dot blot apparatus is used to deposit samples of fragmented and denatured genomic or amplified DNA on a nylon or nitrocellulose membrane. After cross-linking the nucleic acid to the membrane, either through exposure to ultra-violet light or by heat, the membrane is incubated with a labeled hybridization probe. The labels are incorporated into the nucleic acid probes by any of a number of means well-known in the art. The membranes are washed to remove non-hybridized probes and the association of the label with the target nucleic acid sequence is determined.

A number of well-known robotic systems have been developed for high throughput screening, particularly in a 96 well format. These systems include automated workstations like the automated synthesis apparatus developed by Takeda Chemical Industries, LTD. (Osaka, Japan) and many robotic systems utilizing robotic arms (Zymate II, Zymark Corporation, Hopkinton, Mass.; ORCA™, Beckman Coulter, Fullerton Calif.). Any of the above devices are suitable for use with the present invention. The nature and implementation of modifications to these devices (if any) so that they can operate as discussed herein will be apparent to persons skilled in the relevant art.

In addition, high throughput screening systems themselves are commercially available (see, e.g., Zymark Corp., Hopkinton, Mass.; Air Technical Industries, Mentor, Ohio; Beckman Instruments, Inc. Fullerton, Calif.; Precision Systems, Inc., Natick, Mass., etc.). These systems typically automate entire procedures including all sample and reagent pipetting, liquid dispensing, timed incubations, and final readings of the microplate or membrane in detector(s) appropriate for the assay. These configurable systems provide high throughput and rapid start up as well as a high degree of flexibility and customization. The manufacturers of such systems provide detailed protocols for the use of their products in high throughput applications.

In one variation of the invention, solid phase arrays are adapted for the rapid and specific detection of multiple polymorphic nucleotides. Typically, a nucleic acid probe is linked to a solid support and a target nucleic acid is hybridized to the probe. Either the probe, or the target, or both, can be labeled, typically with a fluorophore. If the target is labeled, hybridization is evaluated by detecting bound fluorescence. If the probe is labeled, hybridization is typically detected by quenching of the label by the bound nucleic acid. If both the probe and the target are labeled, detection of hybridizaiton is typically performed by monitoring a color shift resulting from proximity of the two bound labels.

In one embodiment, an array of probes are synthesized on a solid support. Using chip masking technologies and photoprotective chemistry, it is possible to generate ordered arrays of nucleic acid probes. These arrays, which are known, e.g., as "DNA chips" or as very large scale immobilized polymer arrays (VLSIPS™ arrays) can include millions of defined probe regions on a substrate having an area of about 1 cm$^2$ to several cm$^2$.

In another embodiment, capillary electrophoresis is used to analyze polymorphism. This technique works best when the polymorphism is based on size, for example, AFLP and SSR. This technique is described in detail in U.S. Pat. Nos. 5,534,123 and 5,728,282. Briefly, capillary electrophoresis tubes are filled with the separation matrix. The separation matrix contains hydroxyethyl cellulose, urea and optionally formamide. The AFLP or SSR samples are loaded onto the capillary tube and electrophoresed. Because of the small amount of sample and separation matrix required by capillary electrophoresis, the run times are very short. The molecular sizes and therefore, the number of nucleotides present in the nucleic acid sample is determined by techniques described herein. In a high throughput format, many capillary tubes are placed in a capillary electrophoresis apparatus. The samples are loaded onto the tubes and electrophoresis of the samples is run simultaneously. See, Mathies and Huang, (1992) Nature 359:167.

EXAMPLES

The simulation examples described herein are for illustrative purposes only, numerous modifications and changes in light thereof will be suggested to persons skilled in the art and are to be included within the spirit and purview of this application and scope of the appended claims. Accordingly, the following examples are offered to illustrate, but not to limit the claimed invention.

The results of the simulations indicated that on average the Mapping As-You-Go method outperformed the Mapping Start Only method over a large range of genetic models and breeding scenarios. As is discussed in more detail in the following examples, the difference in performance between the two methods increased over the duration of the breeding program, and was influenced by the frequency at which updating of QTL effects was conducted. The method that updated QTL estimates every cycle of the breeding program had the highest response and the method that updated QTL estimates the least had the lowest response. Several factors influenced the magnitude of the difference in performance between the two methods. These were: the complexity of the genetic architecture of the trait, the heritability of the trait, and the MAS weighting level used in the selection. Most notably, there was little to no difference between the two methods for the scenarios where additive genetic models were considered. There was a significant difference between the two methods for the scenarios where epistatic genetic models were considered. In addition, the environment type used in the selection process influenced the difference in performance between the two methods. For example, a greater difference in performance was observed for the Severe Terminal Stress and Mild Terminal Stress environments compared to the Mid-season Stress environment.

The QU-GENE software was used to conduct the following breeding and selection simulation. The development of the E(NK) model and its implementation in QU-GENE has enabled an evaluation of the effects of epistasis and genotype x environment interaction effects in mapping and selection (Cooper and Podlich (2002) The E(NK) Model: Extending the NK Model to Incorporate Gene-by-Environment Interactions and Epistasis for Diploid Genomes *Complexity* Wiley Periodicals, Inc., Vol. 7, No.6:31-47). This software is fully described in Podlich and Cooper (1998) QU-GENE: a simulation platform for quantitative analysis of genetic models *Bioinformatics* 14:632-653, which is incorporated herein for all purposes.

Figure 3:
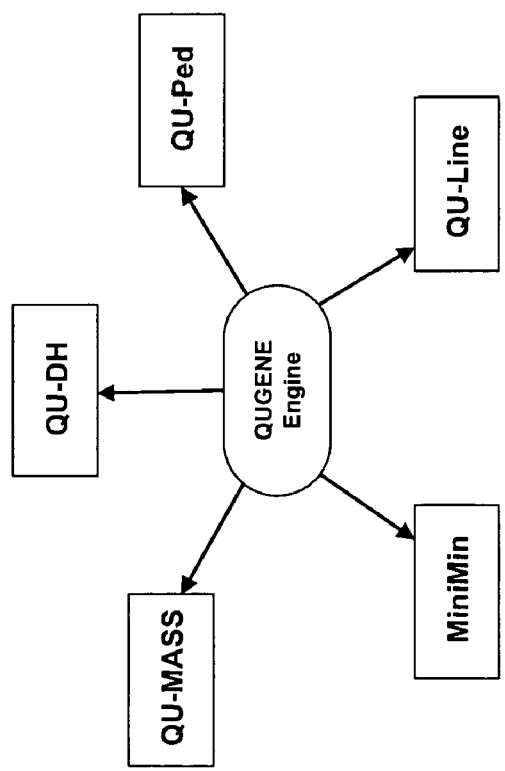
FIG. 3: Schematic representation of the operation of the QU-GENE software.

Briefly, the QU-GENE software consists of two main components: i) the engine; referred to as QUGENE, and ii) the application modules (FIG. 3). The role of the engine is to define the genetics of the system under evaluation. Numerous parameters are used to define the genetics. These include: the number of genes/QTL, location of genes/QTL on chromosomes, genetic effects of QTL including additive, dominance, epistatic, and gene x environment interaction effects, pleiotropic genes, molecular markers, heritability of the traits, and environmental information in the form of a target population of environments (Comstock, 1977; Cooper and Hammer, 1996). See Podlich and Cooper (1998) for additional details.

Figure 2:
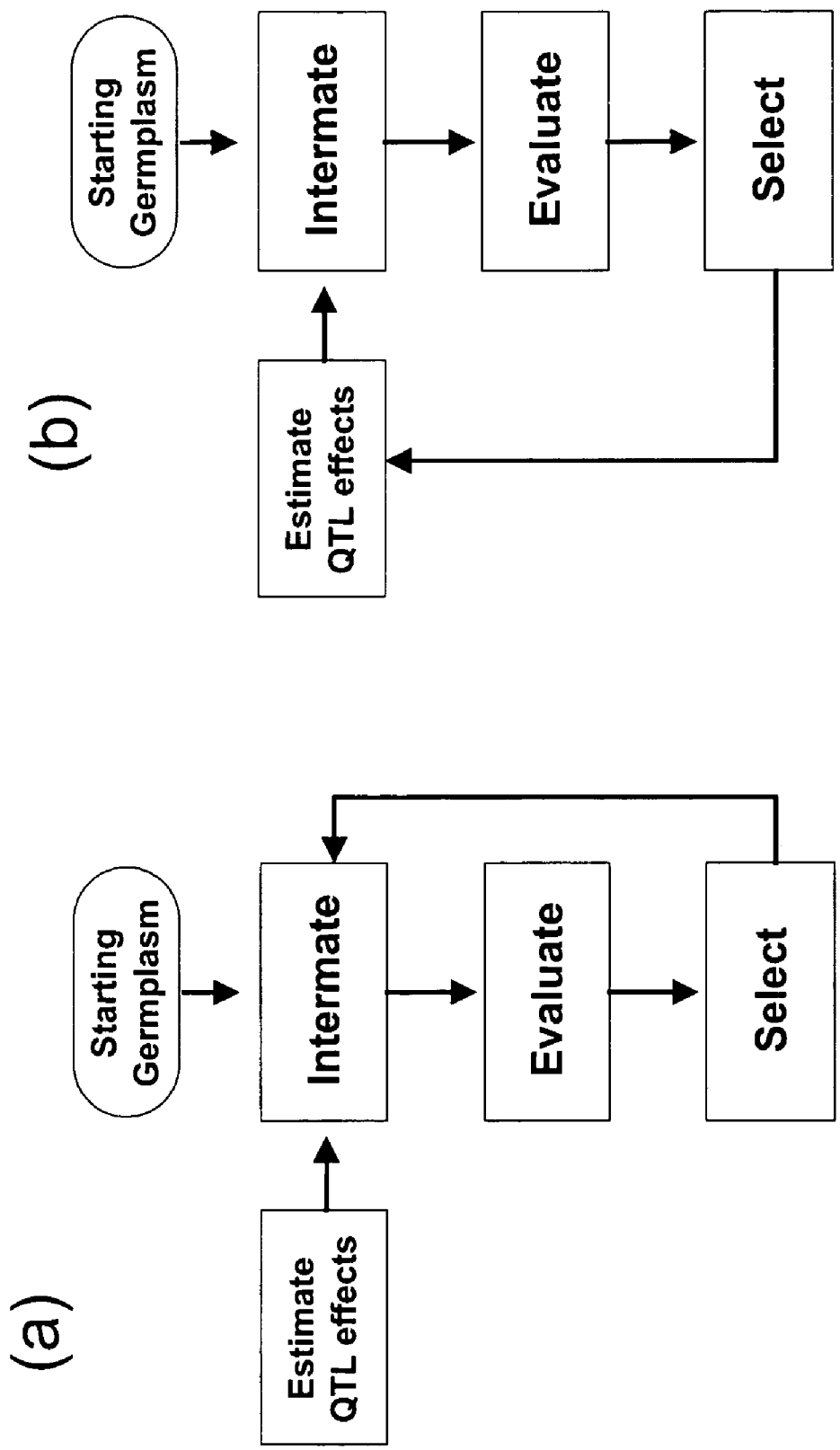
FIG. 2: Schematic representation the basic structure of a breeding program using (a) Mapping Start Only and (b) Mapping As-You-Go approaches to marker assisted selection.

The role of the application modules is to investigate properties of genotypes that exist in the genetic system as defined by the parameters in the engine. Usually, an application module encodes the operation of a plant breeding program. MAS was implemented in the breeding program by evaluating hybrid performance based on an index of phenotypic and genotypic information. The phenotypic information used in the index was based on the average performance of the hybrid combinations across the ten locations sampled in the MET. For the genotypic evaluation, a molecular score was assigned to each hybrid combination according to the genetic similarity of the hybrid with the target configuration of marker alleles as defined by the QTL analysis. Genotypic scores of individual loci were weighted based on the magnitude of the allele effect as defined by the QTL analysis. For example, the top 100 inbreds in each germplasm pool were selected based on the combined index of hybrid phenotypic and genotypic information and retained for the next breeding cycle. The process of pedigree breeding, hybrid evaluation and selection was conducted over, e.g., 30 cycles of the breeding program. For the Mapping Start Only approach, the QTL effects were estimated in cycle 1 of the breeding program and used throughout the 30 cycles of selection. For the Mapping As-You-Go approach, the QTL effects were re-estimated at selected intervals, e.g., (i) every cycle of the breeding program (i.e., Update=Every cycle), (ii) every 5 cycles of the breeding program (i.e., Update=5 cycles), and (iii) every 10 cycles of the breeding program (i.e., Update=10 cycles). In all cases, the older QTL estimates were completely replaced by the newer QTL estimates. Thus, no information was retained from one QTL mapping analysis to the next. The application modules shown in FIG. 3 represent the encoding of a few types of breeding strategies or breeding programs. Each of these modules has the basic structure shown in FIG. 2 (i.e. the evaluation, selection and intermating of genotypes). It should be noted that the Mapping As-You-Go method can be applied to any of these breeding strategies and/or modules.

Example 1

Simulation of the Mapping-As-You-Go Strategy

Figure 4:
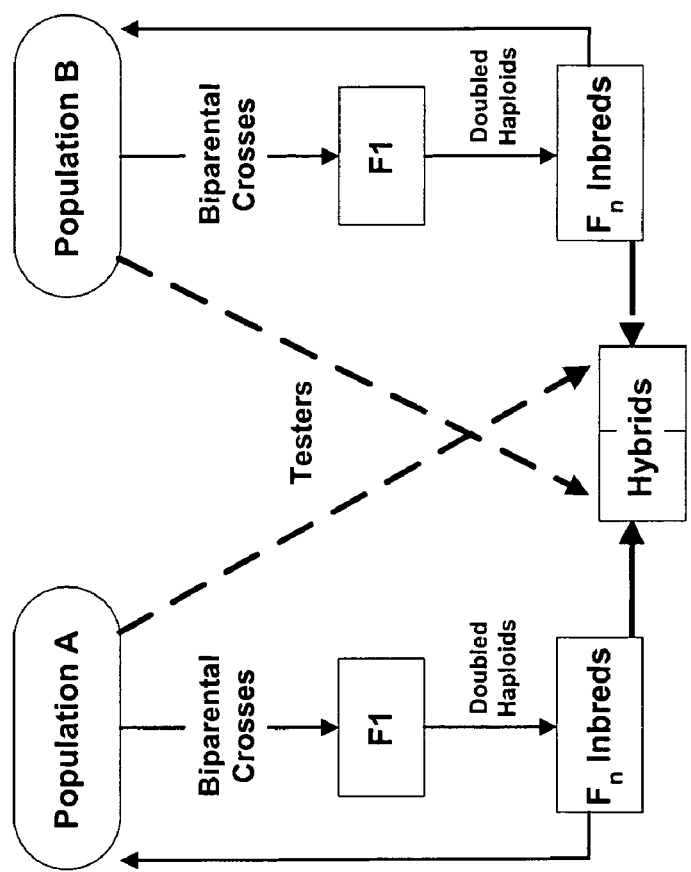
FIG. 4: Schematic representation of operation of the MiniMin module.

In this simulation, the MiniMin application module was run a series of times using a factorial combination of parameter values from the engine and application module. The MiniMin module implements a reciprocal recurrent breeding strategy as shown in FIG. 4. All genetic models have 24 independently segregating QTL (2 alleles per locus), each of which influences the trait on which selection was conducted.

Genetic effects were defined using the E(NK) notation (Cooper and Podlich, 2002). The value of K indicates the average number of loci that interact with a specified gene. For example, K=0 indicates that no other loci influence the genetic effects of the specified gene, that is, K=0 corresponds to an additive gene system. For K=1, digenic networks are in operation. For K=2, trigenic networks are in operation, etc. Heritability defines the level of error associated with the phenotype. Higher heritability values correspond to lower error levels. See Podlich and Cooper (1998) for a description of how this parameter is implemented within QU-GENE.

Figure 5:
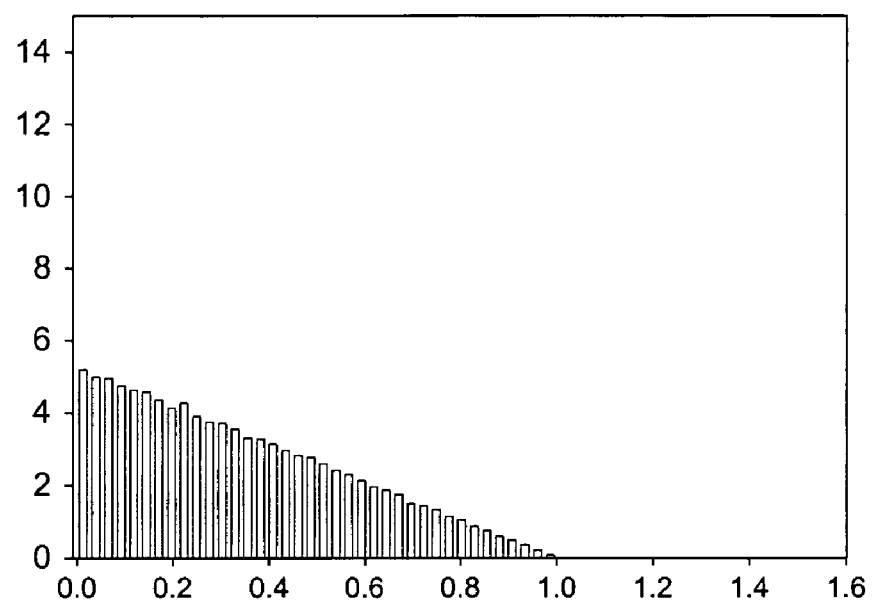
FIG. 5: Bar graph illustrating distribution of gene effects for (a) additive and (b) epistatic systems using an E(NK) ensemble approach. Number of genes (%) is indicated on the vertical axis. Gene value is indicated on the horizontal axis.
Figure 5:
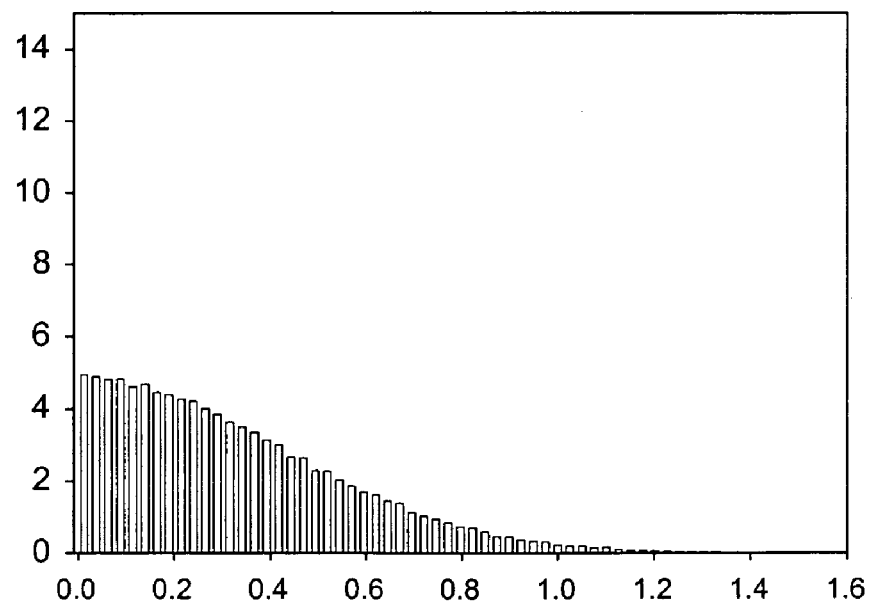

An ensemble approach was used in the simulation. See Cooper and Podlich (2002) for description of how this approach is implemented in QU-GENE. Briefly, an ensemble approach refers to the creation of many genetic systems, in which the gene effects for each system are drawn at random from the same underlying statistical distribution. This approach generates a continuum of gene effects, such that genetic systems contain genes with major and minor effect (FIG. 5). In this simulation, 25 independent genetic models were created per level of K. That is, for each of the 25 genetic systems, a new and independent set of gene effects were defined.

All breeding strategies were implemented with the following parameters (see, FIG. 4): 20 cycles of selection, 200 individuals in each base population, 100 F1 bi-parental crosses, 5 Fn plants per F1, 10 testers per cross, doubled haploids used to get the Fn generation and 50% of the base population replaced each cycle. Each breeding strategy was run 10 times from the same starting population of genotypes. Each run was independent from the previous ones.

QTL mapping was conducted at either the Start Only or Updated As-You-Go. Based on the QTL mapping analysis, marker scores were computed. A simple approach to the estimation of the QTL effects was adopted in that a molecular marker was perfectly linked to each of the QTL contributing to trait variation; i.e. perfect markers and complete linkage disequilibrium. Thus, each QTL allele could be uniquely identified by a marker allele within every genotype at every stage in the simulation experiment. Estimated QTL effects were obtained for each genotype (e.g. AA, Aa, aa) by averaging the phenotypic values of all individuals in the hybrid populations that contained that genotype. The best performing genotype combinations was assigned a score of 2, the second-best performing genotype was assigned a score of 1 and the lowest performing genotype was given a score of 0. This was done for each of the QTL in the system. The marker score for a given individual plant was then computed as the sum of the individual marker scores. QTL estimates were reset after each cycle of the breeding program such that no information was carried from one cycle to the next. The effects were then contrasted for each genotype. For example, the average performances of all individuals with the AA genotype combination at a locus were compared to all individuals with Aa and aa genotype combinations. For each locus, the magnitude of the effect was estimated and the favorable genotype identified.

It should be noted that the method used to estimate QTL effects in this experiment was one of many possible analysis methods that could be considered and was chosen because of its ease of implementation. It should also be noted that by virtue of implementing a model of perfect linkage between the QTL and markers and using a large number of individuals in the estimation process, relatively accurate estimates of QTL and their effects were obtained. The simulation was constructed in this way so that the QTL estimates were of relatively high quality in any single mapping analysis to insure a focused comparison of the MAS strategies. In the event that the initial estimate was inaccurate, the Mapping As-You-Go strategy will have obvious advantages (i.e., refinement of the initial inaccurate QTL estimates).

Selection was conducted by combining the phenotypic and marker information at each cycle of the breeding program. The phenotypic and marker information can be weighted in different ways. In this experiment, 21 different weighting levels were considered, ranging from phenotypic weightings of 0% to 100%, in steps of 5%. A phenotype weighting of 0% indicates Marker Selection (MS) alone, phenotype weighting of 100% indicates Phenotype Selection (PS) alone, phenotype weighting between 0% and 100% indicates Marker-assisted selection (MAS).

The following parameter values were used.

| Engine parameters (Genetic model parameters): | |
|---|---|
| Epistasis levels: | 5 levels; K = 0, K = 0.5, K = 1, K = 2, K = 3 |
| Heritability: | 3 levels; H = 0.05, 0.5 and 0.95 |
| E(NK) ensemble: | 25 parameterizations per model |
| Total number of genetic models: | 375 |

| MiniMin parameters (Breeding strategy parameters): | |
|---|---|
| Update frequency: | 2 levels; Mapping Start Only; Mapping As-You-Go |
| MAS weighting: | 21 levels; Phenotypic weighting: 0% to 100% in steps of 5% |
| Runs: | 10 times; Reps per combination |
| Total number of breeding strategy parameters: | 42 |
| Total number of runs of MiniMin: | 375 × 42 × 10 = 157,500 times |

Results

Figure 6:
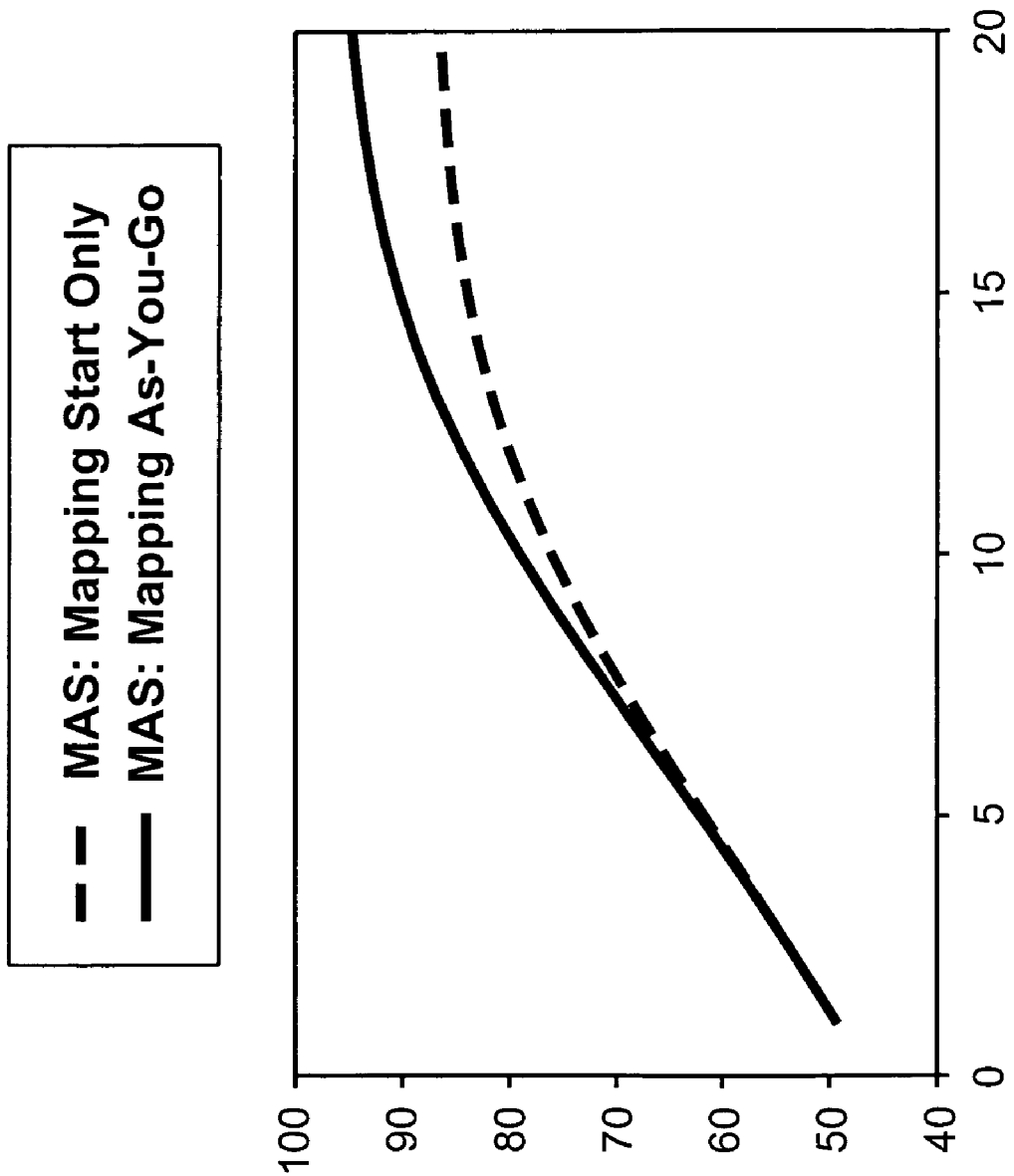
FIG. 6: Line graph illustrating average performance of Mapping As-You-Go and Mapping Start Only strategies averaged over all other parameters (78,750 runs of MiniMin encompassing all levels of epistasis, heritability and MAS weighting). Performance is indicated on the vertical axis. Cycle of the breeding program is indicated on the horizontal axis.
Figure 7:
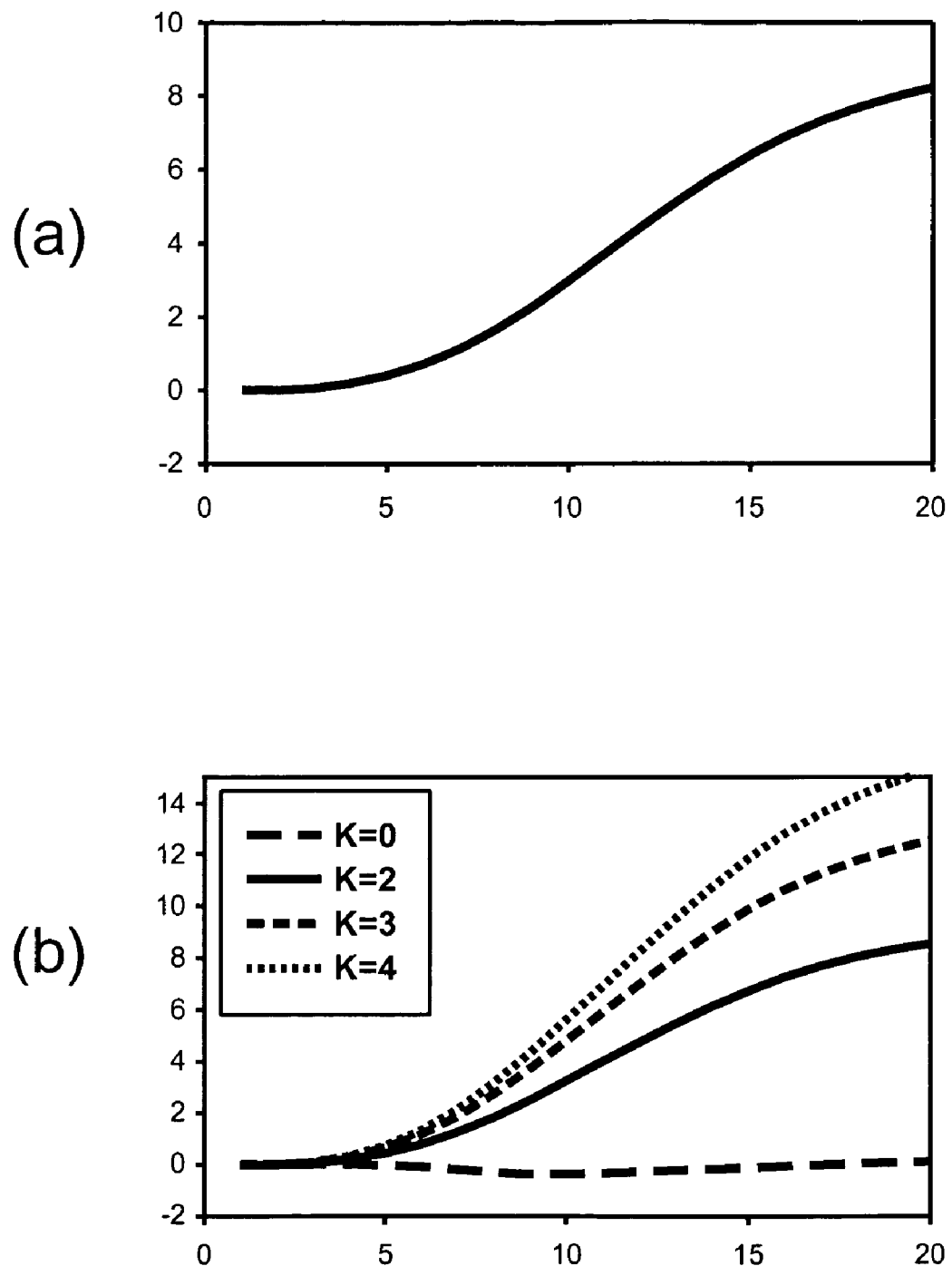
FIG. 7 (*a* and *b*): Line graphs illustrating performance of Mapping As-You-Go strategy relative to Mapping Start Only strategy (a) averaged over all parameters; (b) for different levels of K, averaged over levels of heritability and MAS weighting. Performance relative to Mapping Start Only is indicated on the vertical axis. Cycle of breeding program is indicated on the horizontal axis.

As shown in FIG. 6, the Mapping As-You-Go method generally outperformed the Mapping Start Only method on average. Differences in performance between Mapping As-You-Go and Mapping Start Only increased with progressive breeding cycles. There was little difference in average performance between the two methods in the first 5 cycles (FIG. 7a). After cycle 5, the difference in performance between the two methods increased at each cycle.

Similarly, while the Mapping As-You-Go strategy was effective, even where epistasis was low, e.g., K=0, it significantly out-performed the Mapping Start Only, as the value of K increased (FIG. 7b). Where, K=0, there was little difference in performance between the two methods. This result indicates that the initial QTL effects estimated at the start of the breeding program were effective over a long period of breeding and the updated estimates of the Mapping As-You-Go method provided little additional information to improve selection response. In contrast, for genetic models that contained epistasis (K=1, 2, 3), the Mapping As-You-Go method achieved a higher average level of response than the Mapping Start Only method. Where epistasis plays a significant role, the recursive estimation of QTL effects over cycles using the Mapping As-You-Go method provided a more effective understanding of the genetic architecture of the trait enabling higher responses to be achieved. The advantage that was observed using the Mapping As-You-Go method increased as more epistasis was introduced into the genetic model.

Figure 8:
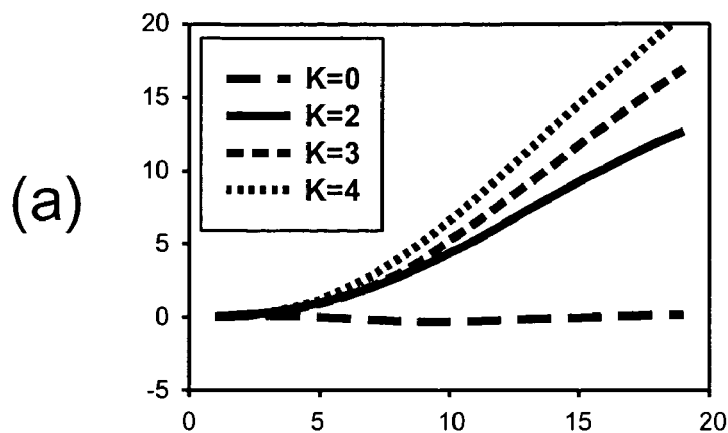
FIG. 8: Line graphs illustrating performance of Mapping As-You-Go strategy relative to Mapping Start Only strategy for four levels of K at levels of heritability equal to (a) 0.1; (b) 0.5 and (c) 0.95. MAS weighting of 50%. Performance relative to Mapping Start Only is indicated on the vertical axis. Cycle of breeding program is indicated on the horizontal axis.
Figure 8:
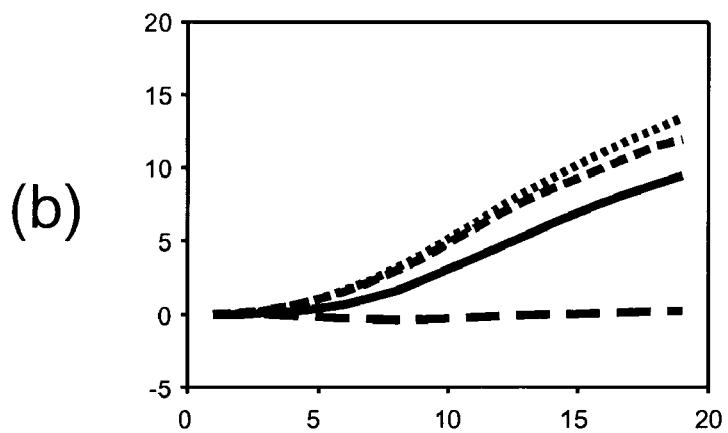
Figure 8:
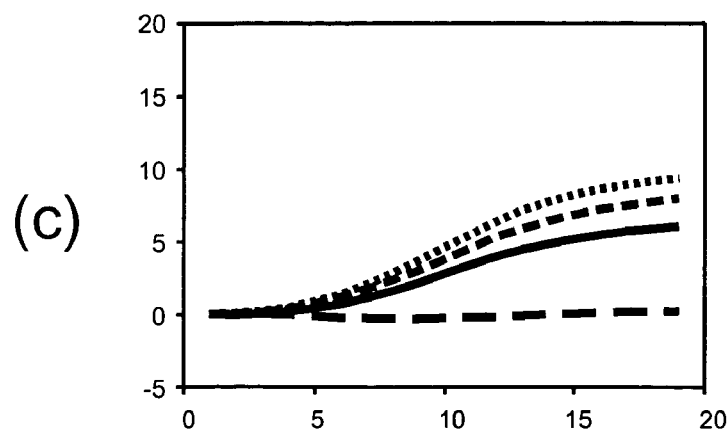

The level of heritability also influenced the difference in performance between the Mapping As-You-Go and Mapping Start Only methods (FIG. 8). The most significant improvement in performance between the Mapping As-You-Go strategy and Mapping Start Only was at the lowest levels of heritability.

Figure 9:
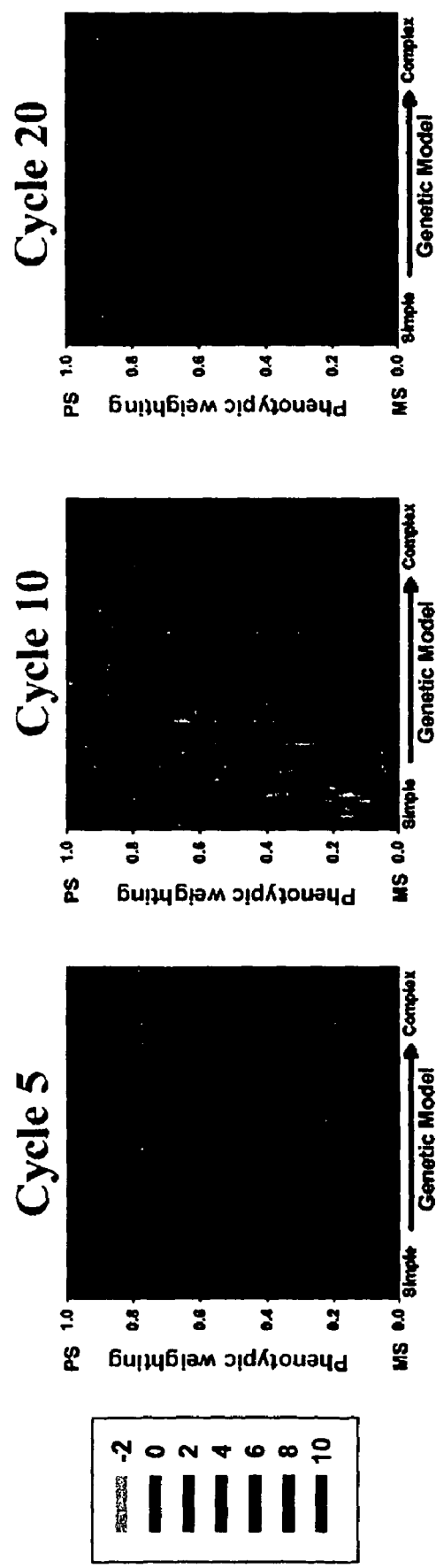
FIG. 9: Graphic snapshot of the performance of the Mapping As-You-Go method relative to the Mapping Start Only method at cycles (a) 5; (b) 10 and (c) 20 of the breeding program. Performance is averaged over all genetic models and MAS weighting levels. Horizontal axis shows performance for all 125 genetic models, ordered from left to right with respect to K value (1-25: K=0; 26-50: K=0.5; 51-75: K=1; 76-100: K=2; 101-125: K=3). Vertical axis shows performance for all individual MAS weighting levels (21 total), ranging from marker selection alone (MS=0%) to phenotypic selection alone (PS=100%). Performance is indicated along a color scale. Yellow-Green indicates that the methods performed equally, increased relative performance is indicated by a shift in the color scale towards violet. In no instances was Mapping As-You-Go inferior to Mapping Start Only.

The MAS weighting level had a large influence on the difference in performance between the two methods (FIG. 9). The difference in performance between the two methods increased as the MAS weighting level gave more emphasis to the marker scores (i.e., low MAS weighting levels). This is represented by the large dark blue panel in the bottom half of FIG. 9 (Cycle 20). For the higher MAS weighting levels, the phenotypic values were given more emphasis and hence the QTL estimates had less influence on response to selection. This is represented by the lighter color component in the top half of FIG. 9 (Cycle 20).

Example 2

Comparison of Updating at Different Cycle Intervals in the Mapping-As-You-Go Strategy This simulation investigated the power of the Mapping As-You-Go approach using different intervals of cycles to update QTL information. QTL effects were estimated at the start only, updated every cycle of the breeding program, or updated intermittently over the course of the breeding program (FIG. 1c). As described above, response was considered for a large range of genetic models and breeding scenarios.

As described in Example 1, the MiniMin module was run using a factorial combination of parameter values from the engine and application module. As above, all genetic models have 24 independently segregating QTL (2 alleles per locus), each of which exerts an influence on the phenotype.

Multiple levels of epistasis were evaluated: K=0 (additive) indicates that all genes were defined to have additive effects (i.e. the values of genotypes for one gene were not context dependent on the genotypes of other genes and the performance of the Aa genotype was half way between the performances of AA and aa). The K=0 (add, dom, over-dom) model indicates that genes were permitted to have additive, dominance and over-dominance effects. In this experiment, 500 independent genetic models were created per level of K. That is, for each of the 500 genetic systems, a new and independent set of gene effects were defined.

All breeding strategies were implemented with the following parameters: 50 cycles of selection, 200 individuals in each base population, 100 F1 bi-parental crosses, 5 Fn plant per F1, 10 testers per cross, doubled haploids used to get the Fn generation and 50% of the base population replaced each cycle.

For purpose of comparison, QTL mapping was conducted at either the Start Only or Updated As-You-Go. Marker scores were computed as described in Example 1. For the Mapping As-You-Go strategy, 4 different updating rates were considered: i) update estimates every cycle, ii) update estimates every 2 cycles, iii) update estimates every 5 cycles, and iv) update estimates every 10 cycles (FIG. 1c).

Selection was conducted by combining the phenotypic and marker information at each cycle of the breeding program as described in Example 1. A phenotype weighting of 0% indicates Marker Selection (MS) alone, phenotype weighting of 100% indicates Phenotype Selection (PS) alone, phenotype weighting between 0% and 100% indicates Marker-assisted selection (MAS).

Each breeding strategy was run 25 times from the same starting population of genotypes. Each run was independent from the previous ones. The parameter values in this simulation were as follows:

| Engine parameters (Genetic model parameters): | |
| --- | --- |
| Epistasis levels: | 5 levels; K = 0 (additive), K = 0 (add, dom, over-dom), K = 1, K = 2, K = 5 |
| Heritability: | 2 levels; H = 0.1 and H = 0.7 |
| E(NK) ensemble: | 500 parameterizations per model |
| Total number of genetic models: | 5000 |

| MiniMin parameters (Breeding strategy parameters): | |
| --- | --- |
| Update frequency: | 5 Start Only; Mapping As-You-Go: Updated (cycles): 1, 2, 5, 10 |
| MAS weighting: | 5 Phenotypic weighting: 0% (MS), 25%, 50%, 75%, 100% (PS) |
| Runs: | 25 times; Reps per combination |
| Total number of breeding strategy parameters: | 25 |
| Total number of runs of MiniMin: | 5000 × 25 × 25 = 3,125,000 times |

Results

Figure 10:
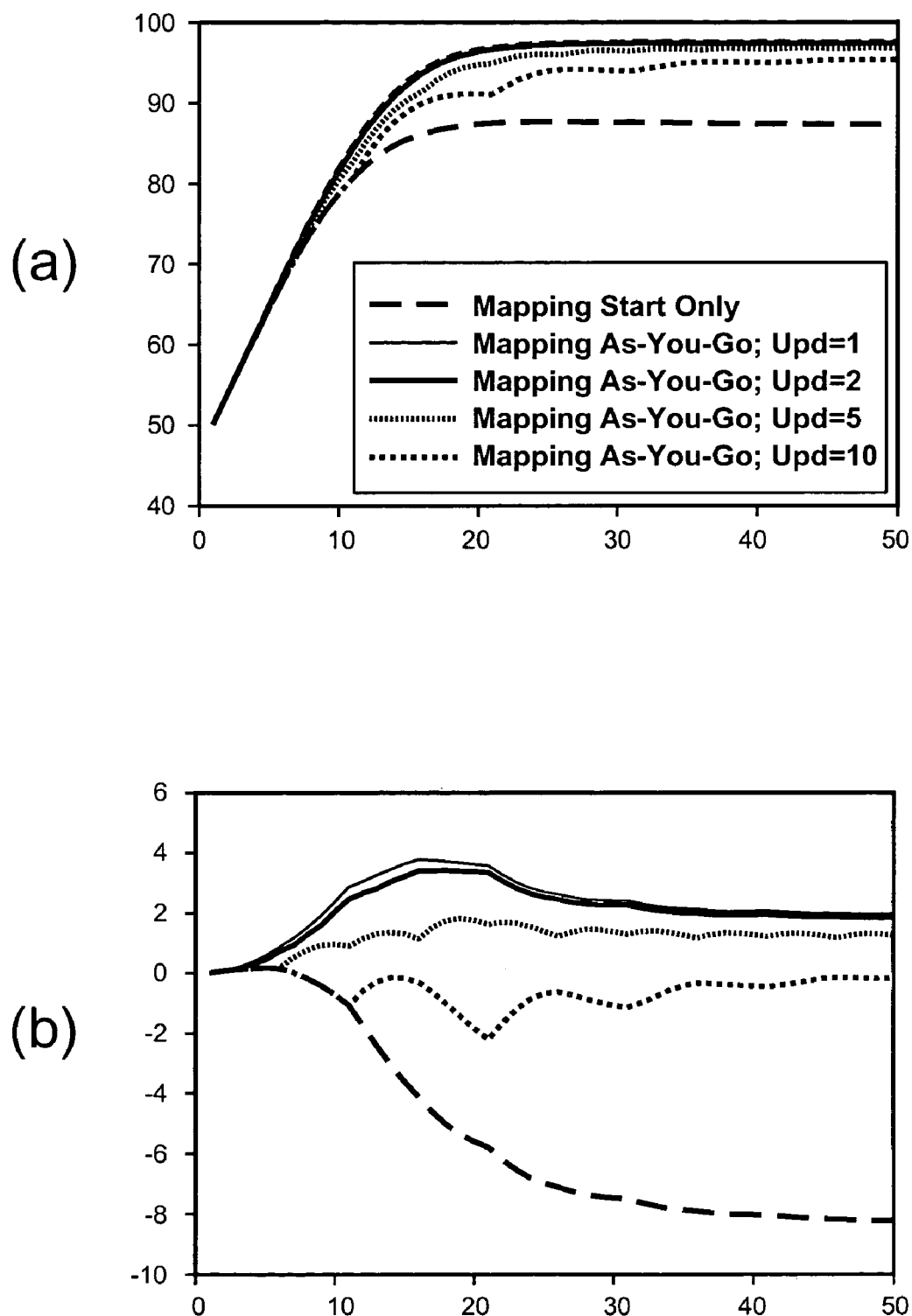
FIG. 10 (*a* and *b*): Line graphs comparing performance of the Mapping Start Only and Mapping As-You-Go strategies with QTL effects updated at different intervals. (a) Results averaged across all other parameters. (b) Results standardized relative to the average response across runs. Standardized performance is indicated on the vertical axis (625,000 runs of MiniMin encompassing all levels of epistasis, heritability and MAS weighting for each updating strategy). Cycle of breeding program is indicated on the horizontal axis. Positive values indicate that the response was higher than the average, whereas negative values indicate a lower than average response.

The Mapping As-You-Go method generally outperformed the Mapping Start Only method (FIG. 10). The performance of the Mapping As-You-Go method was influenced by the frequency at which QTL mapping was conducted. The highest response was obtained by updating QTL estimates every cycle of the breeding program (Upd=1). The lowest response relative to Mapping Start Only was obtained when QTL estimates were updated the least (Upd=10). The response profiles of the four Mapping As-You-Go methods clearly show where the QTL mapping was conducted over the course of the breeding program, as indicated by the sharp jumps in performance (FIG. 10b).

Figure 11:
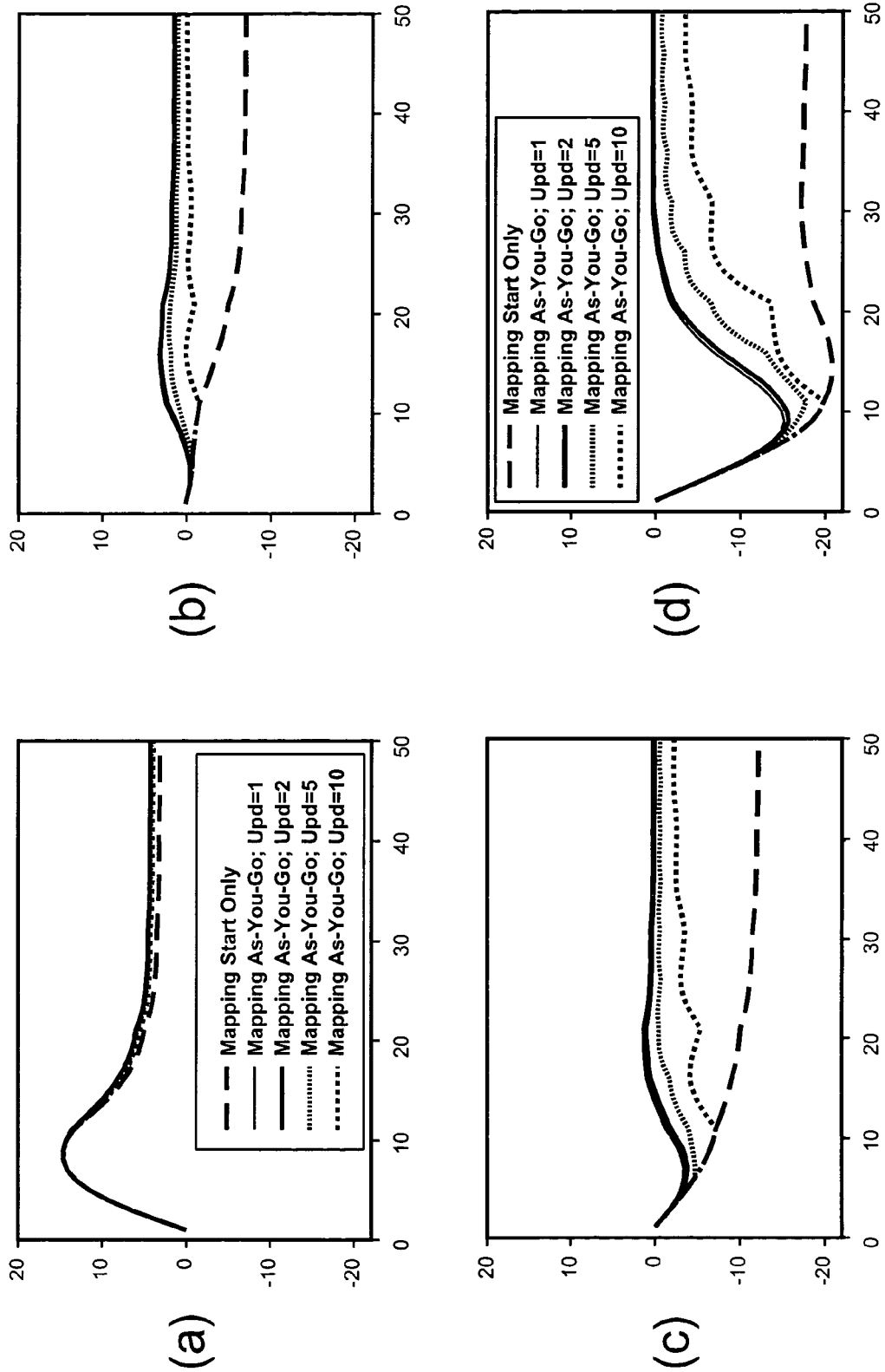
FIG. 11 (*a-d*): Line graphs illustrating standardized performance of the Mapping Start Only and four Mapping As-You-Go approaches for different levels of K: (a) K=0; (b) K=1; (c) K=2; (d) K=3. Standardized performance (%) is indicated on the vertical axis. Cycle of breeding program is indicated on the horizontal axis. Performance has been standardized relative to the average response across all runs.

As described in Example 1, relative performance of the Mapping As-You-Go method increased as the amount of epistasis in the system increased (FIG. 11). For the K=0 genetic models, there was little difference in performance between the Mapping Start Only and the four Mapping As-You-Go methods. In contrast, for genetic models that contained epistasis (K=1,2,3), the Mapping As-You-Go methods achieved a higher average level of response than the Mapping Start Only method.

Figure 12:
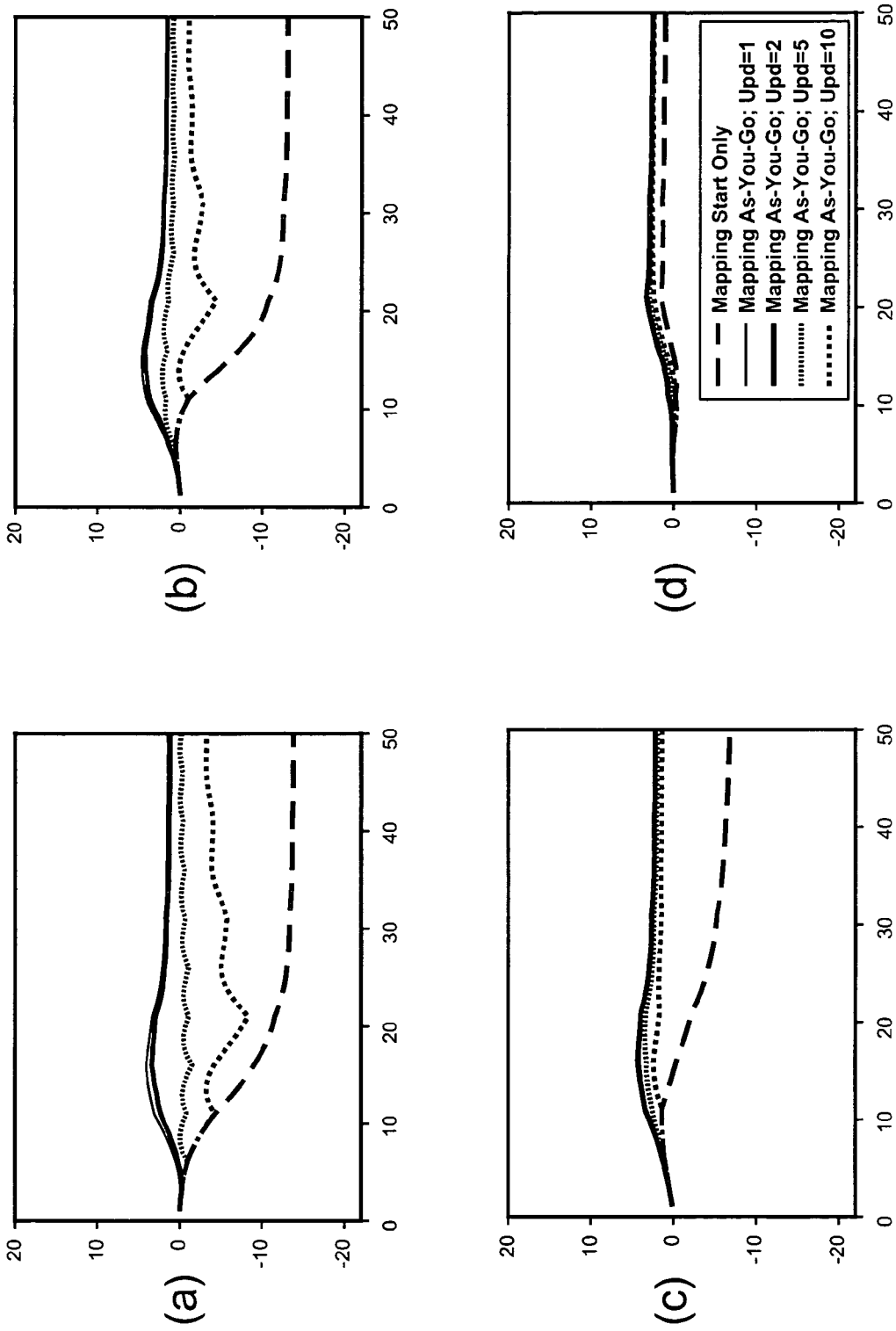
FIG. 12 (*a-d*): Line graphs illustrating standardized performance of the Mapping Start Only and four Mapping As-You-Go approaches for different levels of MAS weighting, averaged over levels of K and heritability: (a) MAS weighting=0%; (b) 25%; (c) 50%; (d) 75%. Standardized performance (%) is indicated on the vertical axis. Cycle of breeding program is indicated on the horizontal axis. Performance has been standardized relative to the average response across all runs.
Figure 13:
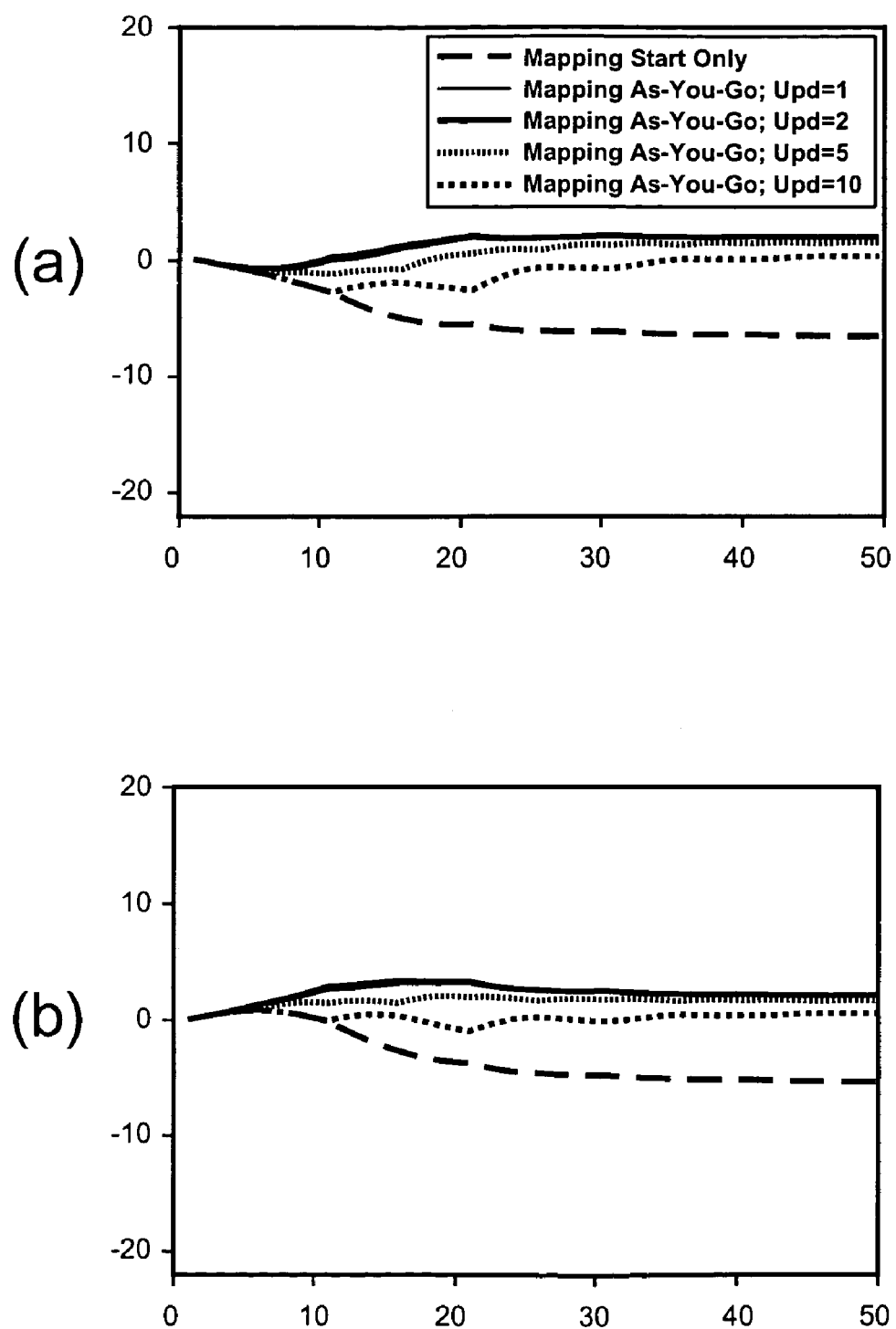
FIG. 13 (*a* and *b*): Line graphs illustrating standardized performance of the Mapping Start Only and four Mapping As-You-Go approaches for heritability levels set at (a) 0.1 and (b) 0.7, averaged over levels of K and MAS weighting. Standardized performance (%) is indicated on the vertical axis. Cycle of breeding program is indicated on the horizontal axis. Performance has been standardized relative to the average response across all runs.

Similarly, the MAS weighting level had a large influence on the performance of the methods (FIG. 12). The greatest difference in performance between the Mapping Start Only and Mapping As-You-Go methods was observed for the breeding strategy that used marker selection alone (i.e., MAS weighting=0%). For strategies that gave greater emphasis to the phenotypic values (e.g., MAS weighting=75%), the difference between the different methods was less prominent. The level of heritability also had a slight influence on the performance of the different mapping methods (FIG. 13).

Example 3

Application of the Mapping-As-You-Go Strategy to a Crop Growth and Development Model Computer simulation using the QU-GENE software was employed to evaluate the Mapping As-You-Go approach to marker-assisted selection in a crop growth and development model. Gene-to-phenotype relationships were defined as described in Cooper et al (2002). Briefly, a look-up table of yield phenotypic values was computed prior to the simulation experiment. This table was created using a crop growth and development model to integrate the expression of four component traits (Transpiration Efficiency, Phenology, Osmotic Adjustment, Stay-green) within three general classes of environment type (Severe Terminal Stress, Mid-season Stress, Mild-terminal Stress). Numbers of genes and genetic effects were defined for each of the four component traits. The genetic effects were categorized into expression states for each of the traits. Thus, the gene-to-phenotype model was constructed such that specific genes influenced specific component traits and these component traits were integrated using a crop growth model to give estimates for the trait yield. Selection was based on the performance of the yield trait.

In this simulation, all genetic models have 15 independently segregating QTL (2 alleles per locus). It was assumed that the four component traits were influenced by 5 (Transpiration Efficiency), 3 (Phenology), 2 (Osmotic Adjustment), and 5 (Stay-green) genes. Gene effects for the traits were defined as additive and equal.

The sorghum crop growth model described in detail in Cooper et al. (2002) was used. The crop growth model was considered in three types of environment. Response to selection was considered in each of these environment types.

All breeding strategies were implemented with the following parameters: 30 cycles of selection, 200 individuals in each base population, 100 F1 bi-parental crosses, 5 Fn plants per F1, 10 testers per cross, doubled haploids used to get the Fn generation and 50% of the base population replaced each cycle.

QTL mapping was conducted at either the Start Only or updated recursively at each cycle of the breeding and selection program as described in Example 1. Marker scores were assigned to all of the genes regardless of which trait they influenced. Selection was conducted by combining the phenotypic and marker information at each cycle of the breeding program as described in Example 1.

QTL estimates were generated in one of two ways: i) using the phenotypic values of the genotypes in an environment type for a given cycle of the breeding program (i.e. phenotypic errors incorporated), or ii) using the explicit value of genotypes in an environment type for a given cycle of the breeding program (i.e., no phenotypic errors incorporated).

Each breeding strategy was run 25 times from the same starting population of genotypes. Each run was independent from the previous ones.

| Engine parameters (Genetic model parameters): | |
| --- | --- |
| Genetic model: | 1 Sorghum crop growth model |
| Environment Type: | 3 Severe Terminal Stress, Mid-season Stress, Mild-terminal Stress |
| Heritability: | 2 levels H = 0.05 and H = 1.0 |
| Total number of genetic models: | 6 |

| MiniMin parameters (Breeding strategy parameters): | |
| --- | --- |
| Update frequency: | 2 types; Mapping Start Only; Mapping As-You-Go |
| MAS weighting: | 5 levels; Phenotypic weighting: 0% (MS), 25%, 50%, 75%, 100% (PS) |
| QTL estimates: | 2 types; Phenotypic; Explicit |

-continued

| MiniMin parameters (Breeding strategy parameters): | |
| --- | --- |
| Runs: | 100 times; Reps per combination |
| Total number of breeding strategy parameters: | 20 |
| Total number of runs of MiniMin: | 6 × 20 × 100 = 12,000 times |

Results

Figure 14:
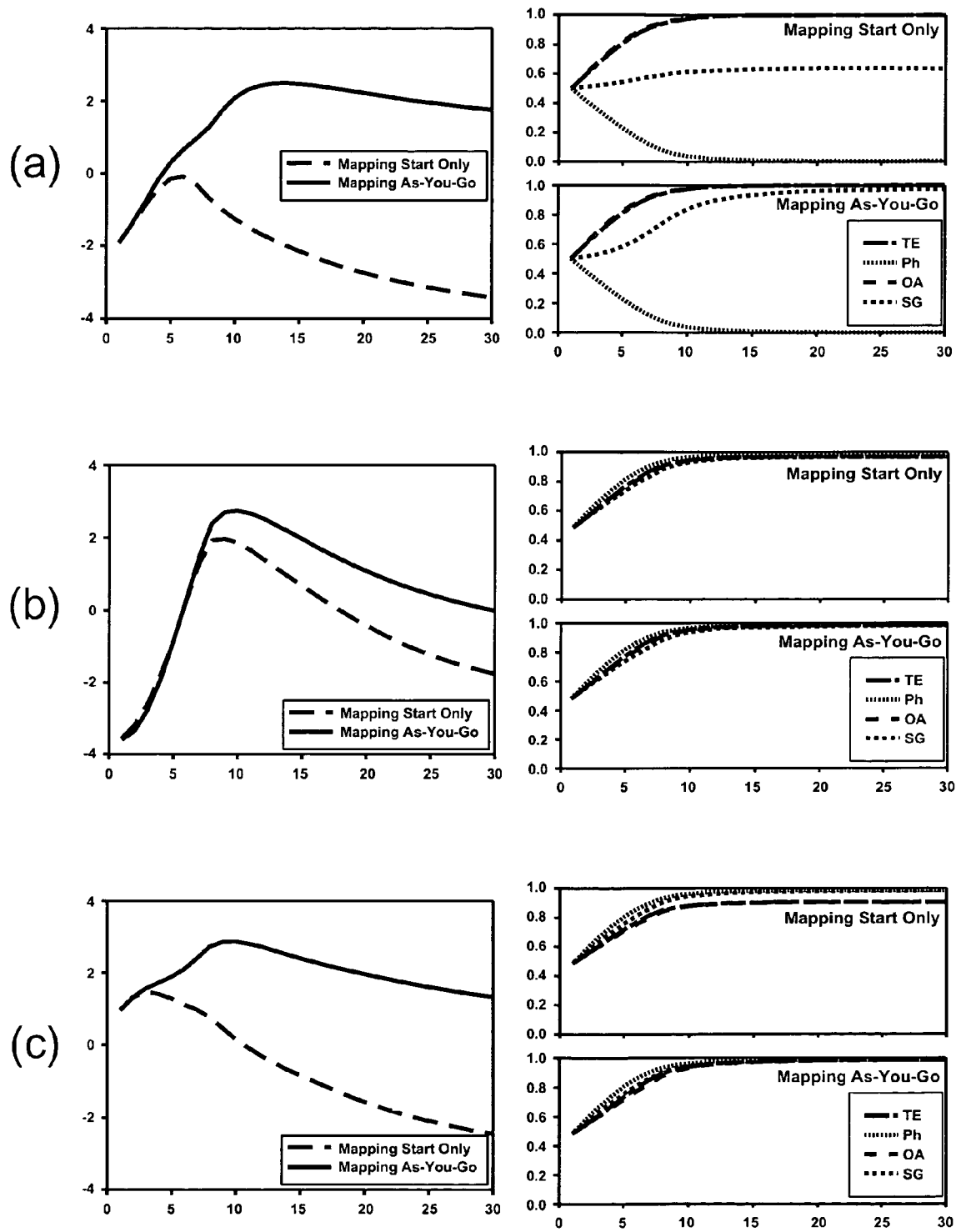
FIG. 14: Line graphs illustrating performance of the Mapping Start Only and four Mapping As-You-Go approaches for three types of environment (a) severe terminal stress, (b) mid season stress, and (c) mild terminal stress. Standardized performance, relative to the average response across all runs is shown in the left panel. The change in gene frequency of the four component traits for the two methods is shown in the right panel.

As in previous simulations, on average the Mapping As-You-Go method outperformed the Mapping Start Only method (FIG. 14). The environment type used in the selection process influenced the difference in performance between the two methods. A greater difference in performance was observed for the Severe Terminal Stress and Mild Terminal Stress environments compared to the Mid-season Stress environment.

The different response profiles of the two methods can be explained by the change in gene frequencies for the component traits (FIG. 14; right panel). Within the Severe Terminal Stress environment, the change in gene frequency for the trait Stay-green was much slower for the Mapping Start Only method than for the Mapping As-You-Go method. Within the Mid-season Stress environment, where the least difference in performance between the two methods was observed, the change in gene frequencies for the two methods was relatively similar across the component traits. The exception to this was a slight difference in gene frequency for the trait Stay-green. Within the Mild Terminal Stress environment, the change in gene frequencies for the traits Transpiration Efficiency and Osmotic Adjustment was much slower for the Mapping Start Only method than for the Mapping As-You-Go method.

Figure 15:
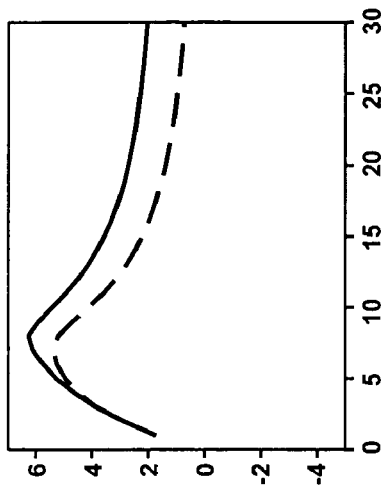
FIG. 15 (*a* and *b*): Line graphs illustrating standardized performance of the Mapping Start Only and four Mapping As-You-Go approaches for different levels of heritability (a) 1.0; and (b) 0.05, averaged over levels of MAS weighting and QTL estimation type, in three different environments: severe terminal stress (left panel); mid season stress (center panel) and mild terminal stress (right panel). Standardized performance (%) is indicated on the vertical axis. Cycle of breeding program is indicated on the horizontal axis.
Figure 15:
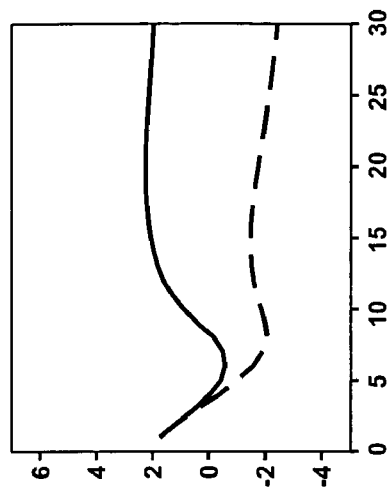
Figure 15:
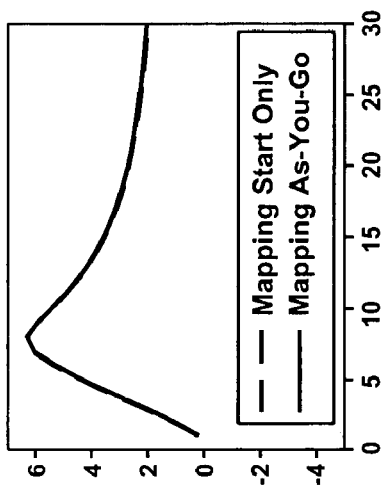
Figure 15:
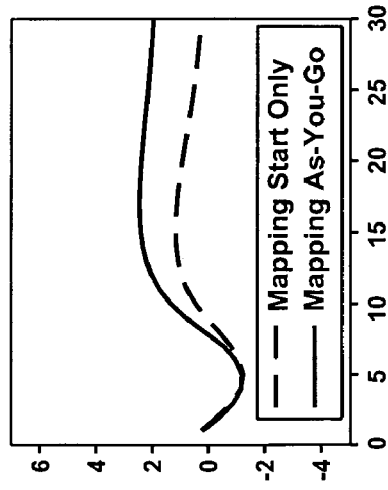
Figure 15:
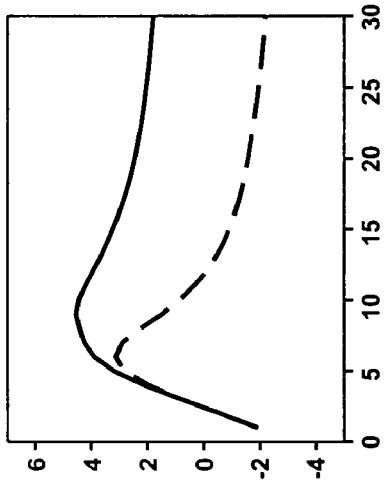
Figure 15:
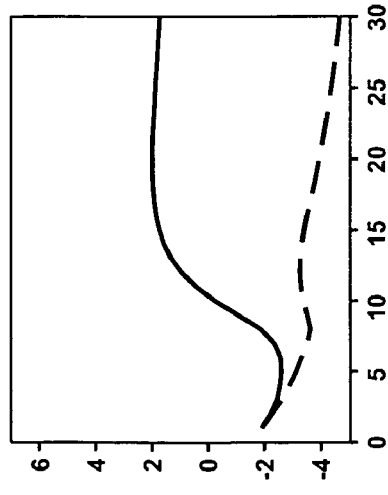

As in the previous examples, there was a difference in performance for the two methods for the different levels of heritability (FIG. 15). The results showed that there was a greater difference in performance at the low heritability level (H=0.05). The difference was greater for the Severe Terminal Stress and Mild Terminal Stress environments.

Figure 16:
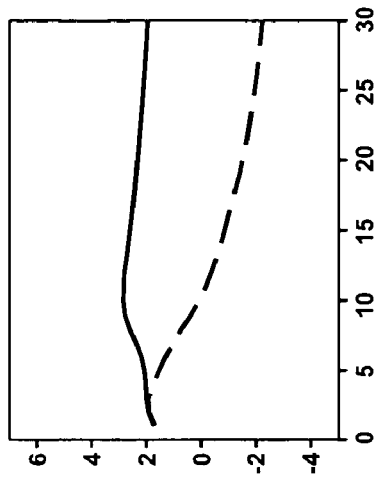
FIG. 16 (*a* and *b*): Line graphs illustrating standardized performance of the Mapping Start Only and four Mapping As-You-Go approaches where QTL estimates are generated by (a) using phenotypic QTL estimates; and (b) using explicit QTL estimates, (averaged over levels of MAS weighting and heritability) in three different environments: severe terminal stress (left panel); mid season stress (center panel) and mild terminal stress (right panel). Standardized performance (%) is indicated on the vertical axis. Cycle of breeding program is indicated on the horizontal axis.
Figure 16:
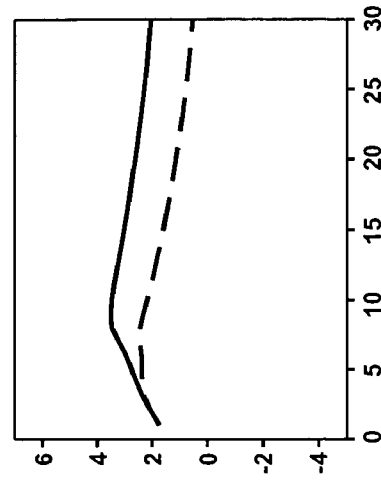
Figure 16:
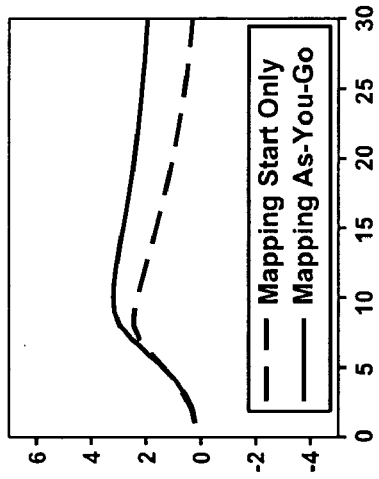
Figure 16:
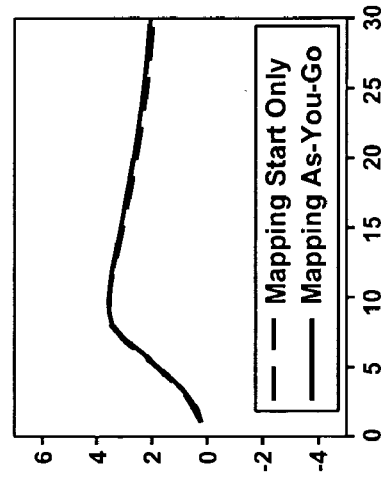

There was a difference in performance for the two methods for the different ways in which the QTL effects were estimated (FIG. 16). For the scenarios where QTL effects were estimated using explicit effects, there was a slightly less difference in performance between the two methods compared to scenarios where QTL effects were estimated using phenotypic information (i.e., environmental error incorporated).

Figure 17:
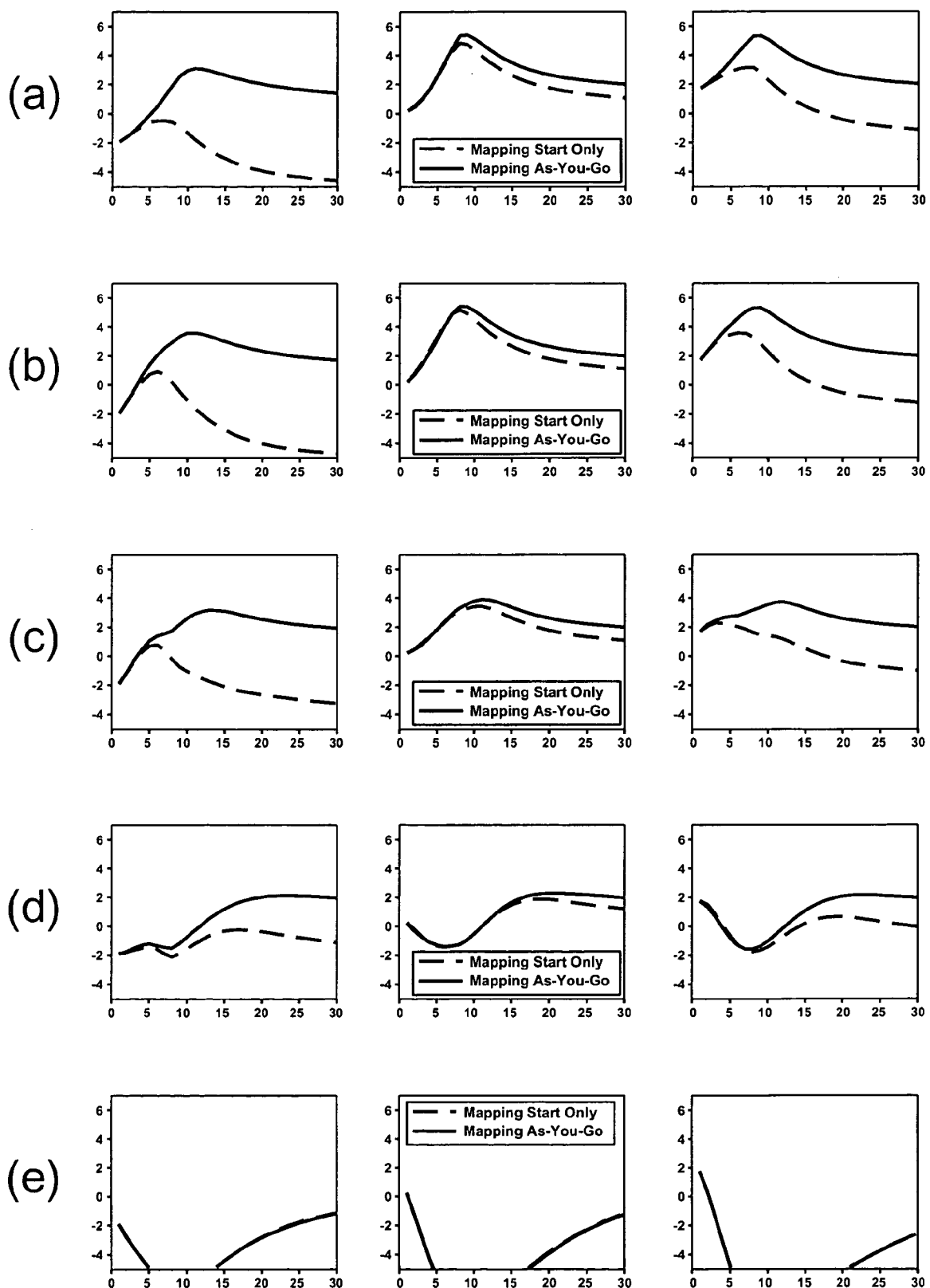
FIG. 17 (*a-e*): Line graphs illustrating standardized performance of the Mapping Start Only and four Mapping As-You-Go approaches for different levels of MAS weighting: (a) 0%; (b) 25%; (c) 50%; (d) 75%; (e) 100% (averaged over heritability levels and QTL estimation type) in three different environments: severe terminal stress (left panel); mid season stress (center panel) and mild terminal stress (right panel). Standardized performance (%) is indicated on the vertical axis. Cycle of breeding program is indicated on the horizontal axis.

The MAS weighting level also influenced the relative performance of the methods (FIG. 17). The greatest difference in performance between the Mapping Start Only and Mapping As-You-Go methods was observed for the breeding strategy that used marker selection alone (i.e., MAS weighting=0%). For strategies that gave greater emphasis to the phenotypic values (e.g. MAS weighting=75%), the difference between the different methods was minimal. As expected, there was no difference in the two methods for the strategy that conducted phenotypic selection alone (i.e. MAS weighting=100%).

Example 4

The Efficiency of the Mapping-As-You-Go Strategy for Different Levels of Epistasis and Gene-By-Environment Interaction In this simulation experiment, the efficiency of the Mapping As-You-Go approach was considered for different levels of epistasis and gene-by-environment interaction. QTL effects were estimated at the start only, updated every cycle of the breeding program, or updated intermittently over the course of the breeding program. This experiment is an extension of those described in Examples 1 and 2.

As described in Examples 1 and 2, the MiniMin module was run using a factorial combination of parameter values from the engine and application module. The genetic models were created using the E(NK) model ensemble approach (Podlich and Cooper, 1998; Cooper and Podlich, 2002), where E refers to the number of different environment types conditioning gene-by-environment interactions in the target population of environments, N refers to the number of genes influencing the trait and K is a measure of the level of epistasis. For a given number of N genes, different levels of context dependency due to gene-by-environment interaction and epistasis can be introduced by varying the E and K parameters. Increased levels of E indicate more gene-by-environment interaction and larger values of K indicate more epistasis. In this experiment, a total of nine general classes of genetic model were considered (Table 1).

TABLE 1

Summary of Genetic Models

| | | E values | | |
|---|---|---|---|---|
| | | 1 | 5 | 10 |
| K values | 0 | Additive Models | Gene-b-environment Models only | |
| | 1 | Epistatic Models only | Gene-by-environment and epistatic Models | |
| | 2 | | | |

The first general class of genetic model had only additive effects; i.e. E=1, K=0 (a classical finite locus additive model). Two of the general classes of genetic model had epistatic effects and no gene-by-environment interaction effects; i.e. E=1, K=1, 2. Two of the general classes of genetic model had gene-by-environment effects and no epistatic effects; i.e. K=0, E=5, 10. The remaining four general classes of genetic model had a combination of gene-by-environment and epistatic effects; i.e. all combinations of E=5, 10; K=1, 2. For each class of genetic model, four levels of N were considered; N=12, 24, 48, 96. In all cases, the genetic effects for the QTL alleles were sampled at random from an underlying uniform distribution according to the description given in Cooper and Podlich (2002). For each general class of genetic model, a total of 500 different random parameterizations of the E(NK) model were considered. Scenarios were run for heritability levels of 0.1 and 0.7 on a single plant basis.

All breeding strategies were implemented with the following parameters: 30 cycles of selection, 200 individuals in each base population, 100 F1 bi-parental crosses, 5 Fn plants per F1, 10 testers per cross, doubled haploids used to get the Fn generation and 50% of the base population replaced each cycle. Each of the hybrid combinations was evaluated in a simulated multi-environment trial (MET) with ten locations. The environment types represented at each location were sampled at random from a target population of environments (Comstock, 1977; Cooper and Hammer, 1996; Cooper and Podlich, 2002). The phenotypic values of the hybrids across the ten locations were used to estimate the QTL allele effects. The QTL analysis method employed in the experiment was the same as that described in Examples 1 and 2.

MAS was implemented in the breeding program by evaluating hybrid performance based on an index of phenotypic and genotypic information. The phenotypic information used in the index was based on the average performance of the hybrid combinations across the ten locations sampled in the MET. For the genotypic evaluation, a molecular score was assigned to each hybrid combination according to the genetic similarity of the hybrid with the target configuration of marker alleles as defined by the QTL analysis. Genotypic scores of individual loci were weighted based on the magnitude of the allele effect as defined by the QTL analysis. The top 100 inbreds in each germplasm pool were selected based on the combined index of hybrid phenotypic and genotypic information and retained for the next breeding cycle. The process of pedigree breeding, hybrid evaluation and selection was conducted over 30 cycles of the breeding program. For the Mapping Start Only approach, the QTL effects were estimated in cycle 1 of the breeding program and used throughout the 30 cycles of selection. For the Mapping As-You-Go approach, the QTL effects were re-estimated: (i) every cycle of the breeding program (i.e. Update=Every cycle), (ii) every 5 cycles of the breeding program (i.e. Update=5 cycles), and (iii) every 10 cycles of the breeding program (i.e. Update=10 cycles). In all cases, the older QTL estimates were completely replaced by the newer QTL estimates. Thus, no information was retained from one QTL mapping analysis to the next. Each of the MAS strategies was independently replicated 25 times for each parameterization of the E(NK) model. In total, the breeding program was run 3.6 million times, encompassing 108 million cycles of selection.

The following parameter values were used.

| Engine parameters (Genetic model parameters): | |
|---|---|
| Epistasis levels: | 3 levels; K = 0, K = 1, K = 2 |
| GxE levels: | 3 levels; E = 1, 5, 10 |
| Gene no. levels: | 4 levels; N = 12, 24, 48, 96 |
| Heritability levels: | 2 levels; H = 0.1, 0.7 |
| E(NK) ensemble: | 500 parameterizations per model |
| Total number of genetic models: | 36,000 |

| MiniMin parameters (Breeding strategy parameters): | |
|---|---|
| Update frequency: | 4 levels Mapping Start Only; Mapping As-You-Go: Updated (cycles): 1, 5, 10 |
| Runs: | 25 times; Reps per combination |
| Total number of breeding strategy parameters: | 4 |
| Total number of runs of MiniMin: | 36,000 × 4 × 25 = 3,600,000 times |

Results

Figure 18:
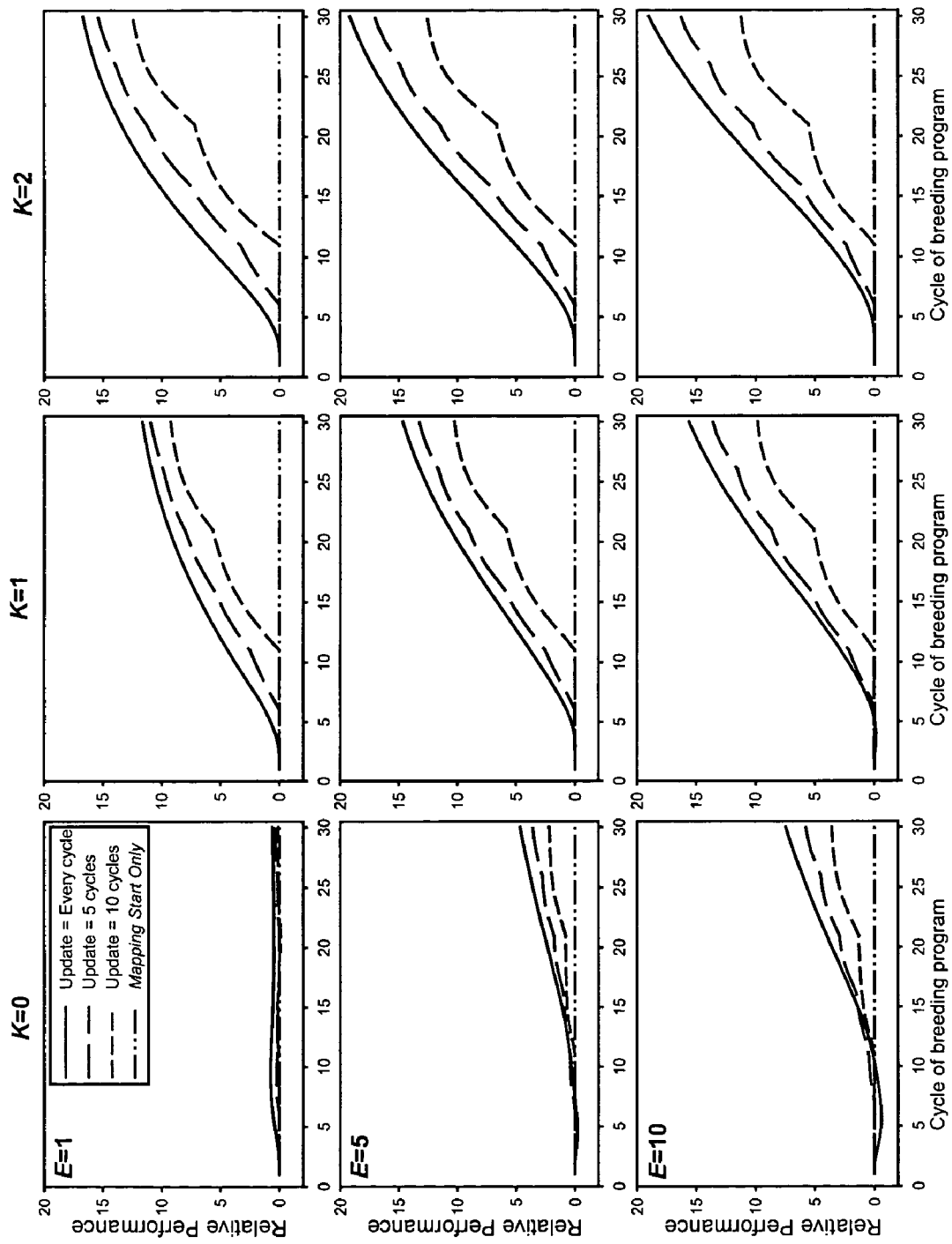
FIG. 18: The relative performance of the Mapping Start Only and three versions of the Mapping As-You-Go approach for nine general classes of genetic model (Table 1); Additive genetic models: E=1, K=0; Epistatic effects models: E=1, K=1, 2; Gene-by-environment effects models: K=0, E=5, 10; Epistasis and gene-by-environment effects models: E=5, 10, K=1, 2. In all cases, performance is represented as the difference in response between a given breeding strategy and the Mapping Start Only method. Positive values indicate the breeding strategy had a higher response than the Mapping Start Only method, and negative values indicate the breeding strategy had a lower response than the Mapping Start Only method. The performance differences are expressed in terms of normalized trait value.

The progress from selection for the Mapping Start Only and Mapping As-You-Go approaches to MAS was evaluated in terms of the average performance of the hybrids at each cycle of the breeding program. On average across all genetic models, the Mapping As-You-Go method outperformed the Mapping Start Only method to MAS. The greatest response was observed for the strategy that updated the QTL allele effects the most frequently (i.e. Update=every cycle). The next highest levels of response were achieved by the strategies that updated the QTL allele effects every 5 and 10 cycles, respectively (Update=5 and 10 cycles; FIG. 18). For these latter two Mapping As-You-Go strategies, there were large increases in relative response immediately after the QTL alleles were re-estimated (e.g. for Update=10 cycles, a jump in performance occurred at cycle 11 and then again at cycle 21). In all cases, the Mapping As-You-Go method outperformed the Mapping Start Only method.

There was a substantial difference in the relative performances of the Mapping Start Only and Mapping As-You-Go methods among the nine general classes of genetic model (FIG. 18). For the class of genetic model where only additive effects were present (i.e. E=1, K=0; top left panel of FIG. 18), there were relatively small differences in performance for the different MAS strategies. This result indicates that the initial estimates of QTL effects were effective over a long period of breeding and hence the updated estimates provided by the Mapping As-You-Go methods offered little additional information to improve selection response. In contrast, for the classes of genetic models that contained epistasis but no gene-by-environment interaction (i.e. E=1; K=1,2; top middle and right panels of FIG. 18), the Mapping As-You-Go methods had higher levels of response than the Mapping Start Only method. Here, the cyclical re-estimation of QTL effects over cycles of selection using the Mapping As-You-Go method provided a more effective estimation of the genetic architecture of the trait within the context of the current germplasm, enabling higher responses to be achieved in the medium to long-term. The size of the advantage that was observed using the Mapping As-You-Go approach increased with K (i.e. more context dependency), or when the QTL effects were estimated more frequently. For genetic models with gene-by-environment interaction effects but no epistasis (i.e. K=0; E=5,10; middle and lower left panels of FIG. 18), the Mapping As-You-Go methods generally achieved higher levels of response compared to the Mapping Start Only method. The Mapping As-You-Go approach had the desirable aspect of using a new sample of environment types in each QTL analysis and thus outperformed the Mapping Start Only approach because the QTL estimates were not fixed indefinitely based on a single sample of environment types from the target population of environments. However, it should be noted that the Mapping Start Only method initially outperformed the Mapping As-You-Go methods for genetic models with gene-by-environment interaction effects only. This was due to the fact that the Mapping As-You-Go method was continually chasing a moving target based on the set of environments sampled in any given cycle (i.e. the 'yo-yo' effect; Rathjen, 1994), thus leading to an initial less desirable response to selection in the target population of environments. When both epistasis and gene-by-environment interaction effects were present (i.e. K=1, 2; E=5, 10; lower right four panels of FIG. 18), the Mapping As-You-Go method on average outperformed the Mapping Start Only method.

Figure 19:
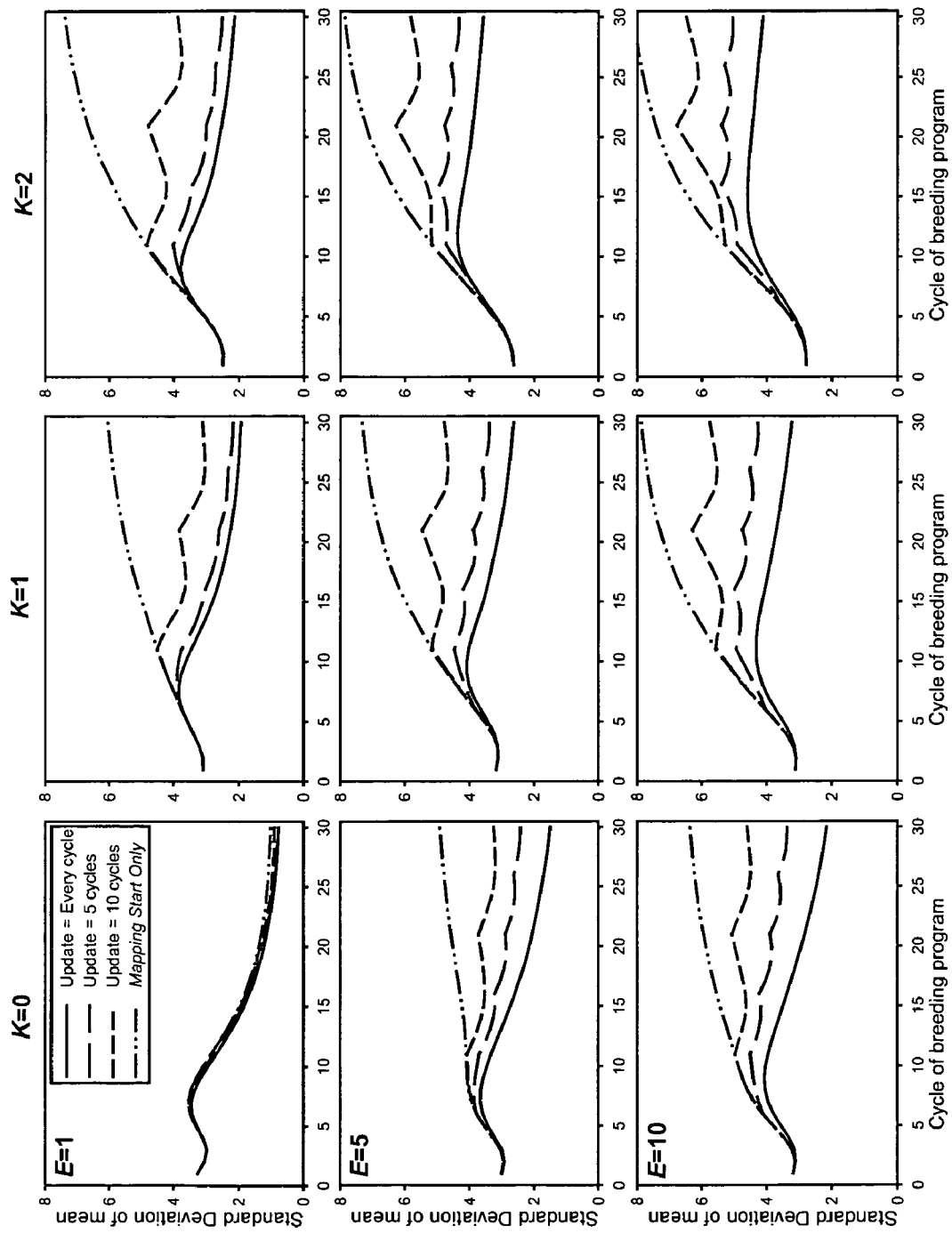
FIG. 19: The standard deviation of performance (FIG. 18) for nine general classes of genetic model (Table 1); Additive genetic models: E=1, K=0; Epistatic effects models: E=1, K=1, 2; Gene-by-environment effects models: K=0, E=5, 10; Epistasis and gene-by-environment effects models: E=5, 10, K=1, 2.

There were differences in the variation of response among the different breeding strategies for the different classes of genetic models (FIG. 19). For the class of genetic model where only additive effects were present (FIG. 19; top left panel), the variation in the response was consistent between the Mapping Start Only method and versions of the Mapping As-You-Go method. In contrast, when context dependencies were present (FIG. 19; all panels except top left), the two approaches show progressively different patterns of variation in the mean response, with the Mapping Start Only method having the most variation, particularly at later cycles.

Figure 20:
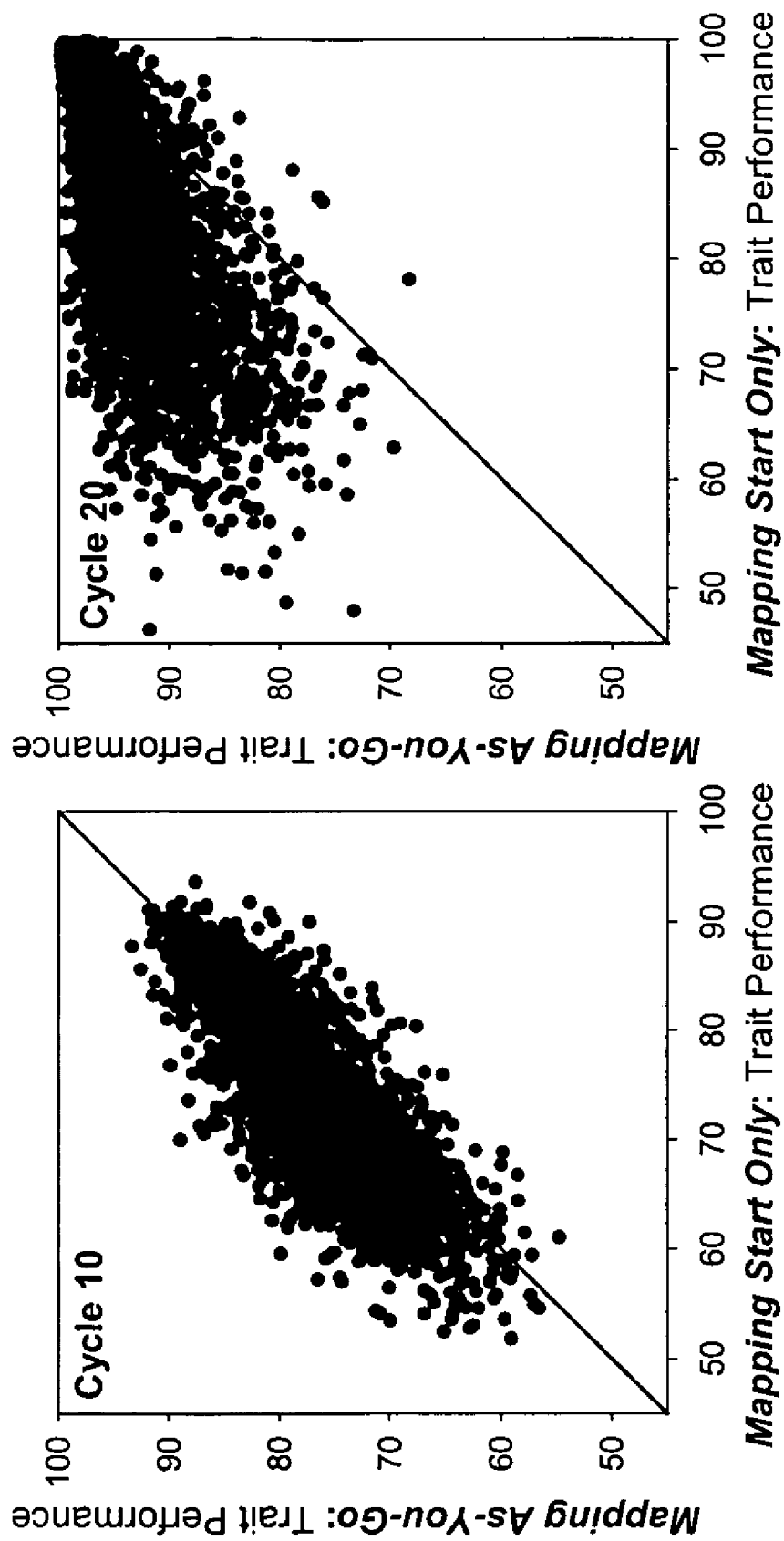
FIG. 20: The performance of the Mapping Start Only and Mapping As-You-Go (Update=every cycle) approaches to MAS at cycles 10 and 20 of the breeding program. Each point represents the response for a single genetic model and a single run of the breeding program. All nine classes of genetic model (Table 1) are shown (250 points per class).

Despite the advantages of the Mapping As-You-Go method as shown in FIGS. 18 and 19, there were still individual occurrences where the Mapping Start Only method outperformed the Mapping As-You-Go method. For example, FIG. 20 shows the performance of individual runs of the Mapping Start Only and Mapping As-You-Go (Update=every cycle) methods, where each point on the figure represents an individual realization of the breeding program for a specific genetic model. Values above the 1:1 line indicate the Mapping As-You-Go method had a higher level of response compared to the Mapping Start Only method. Values below the 1:1 line indicate the Mapping As-You-Go method had a lower level of response compared to the Mapping Start Only method. When viewed from this perspective, there were individual occurrences where the Mapping Start Only method outperformed the Mapping As-You-Go method. Thus, in any given realization of the breeding process and for any given genetic model, the relative performances of the Mapping Start Only and Mapping As-You-Go method can not be guaranteed. However, there is a significant advantage to the Mapping As-You-Go method on average, which was more consistently achieved across individual scenarios when long-term genetic gain was considered (FIG. 20; cycle 10 cf. cycle 20).

Example 5

Simulation of the Mapping-As-You-Go Strategy Using a Mixed Model Analysis for QTL Estimation In this example, the Mapping As-You-Go method was implemented using a mixed model analysis for QTL estimation. In Examples 1 through 4, a relatively simple QTL analysis method was employed. The mixed model analysis considered here is a more advanced analysis technique that utilizes phenotypic and genotypic information, taking into consideration within and among cross information. A similar approach is described by Jannink and Jansen (2001).

In this experiment, a total of six general classes of genetic model were considered (Table 1; Example 4). The first general class of genetic model had only additive effects; i.e. E=1, K=0 (a classical finite locus additive model). Two of the general classes of genetic model had epistatic effects and no gene-by-environment interaction effects; i.e. E=1, K=1, 2. One class of genetic model had gene-by-environment effects and no epistatic effects; i.e. K=0, E=10. The remaining two general classes of genetic model had a combination of gene-by-environment and epistatic effects; i.e. all combinations of E=10; K=1, 2. For each class of genetic model, a single level of N was considered (N=24). In all cases, the genetic effects for the QTL alleles were sampled at random from an underlying uniform distribution according to the description given in Cooper and Podlich (2002). For each general class of genetic model, a total of 100 different random parameterizations of the E(NK) model were considered. Scenarios were run using a heritability level of 0.1 on a single plant basis.

The implementation of the breeding program was the same as that described in Example 4. All breeding strategies were implemented with the following parameters: 30 cycles of selection, 200 individuals in each base population, 100 F1 bi-parental crosses, 5 Fn plants per F1, 10 testers per cross, doubled haploids used to get the Fn generation and 50% of the base population replaced each cycle. Each of the hybrid combinations was evaluated in a simulated multi-environment trial (MET) with ten locations. The phenotypic values of the hybrids across the ten locations were used to estimate the QTL allele effects.

For the Mapping Start Only approach, the QTL effects were estimated in cycle 1 of the breeding program and used throughout the 30 cycles of selection. For the Mapping As-You-Go approach, the QTL effects were re-estimated: (i) every cycle of the breeding program (i.e. Update=Every cycle), (ii) every 5 cycles of the breeding program (i.e. Update=5 cycles), and (iii) every 10 cycles of the breeding program (i.e. Update=10 cycles). In all cases, the older QTL estimates were completely replaced by the newer QTL estimates. Thus, no information was retained from one QTL mapping analysis to the next. Each of the MAS strategies was independently replicated 10 times for each parameterization of the E(NK) model. In total, the breeding program was run 24,000 times, encompassing 720,000 cycles of selection. The following parameter values were used.

| Engine parameters (Genetic model parameters): | |
|---|---|
| Epistasis levels: | 3 levels; K = 0, K = 1, K = 2 |
| GxE levels: | 2 levels; E = 1, 10 |
| Heritability levels: | 1 level; H = 0.1 |
| E(NK) ensemble: | 100 parameterizations per model |
| Total number of genetic models: | 600 |

| MiniMin parameters (Breeding strategy parameters): | | |
|---|---|---|
| Update frequency: | 4 levels | Mapping Start Only; Mapping As-You-Go: Updated (cycles): 1, 5, 10 |
| Runs: | 10 times; | Reps per combination |
| Total number of breeding strategy parameters: 4 | | |
| Total number of runs of MiniMin: 600 × 4 × 10 = 24,000 times | | |

Results

Figure 21:
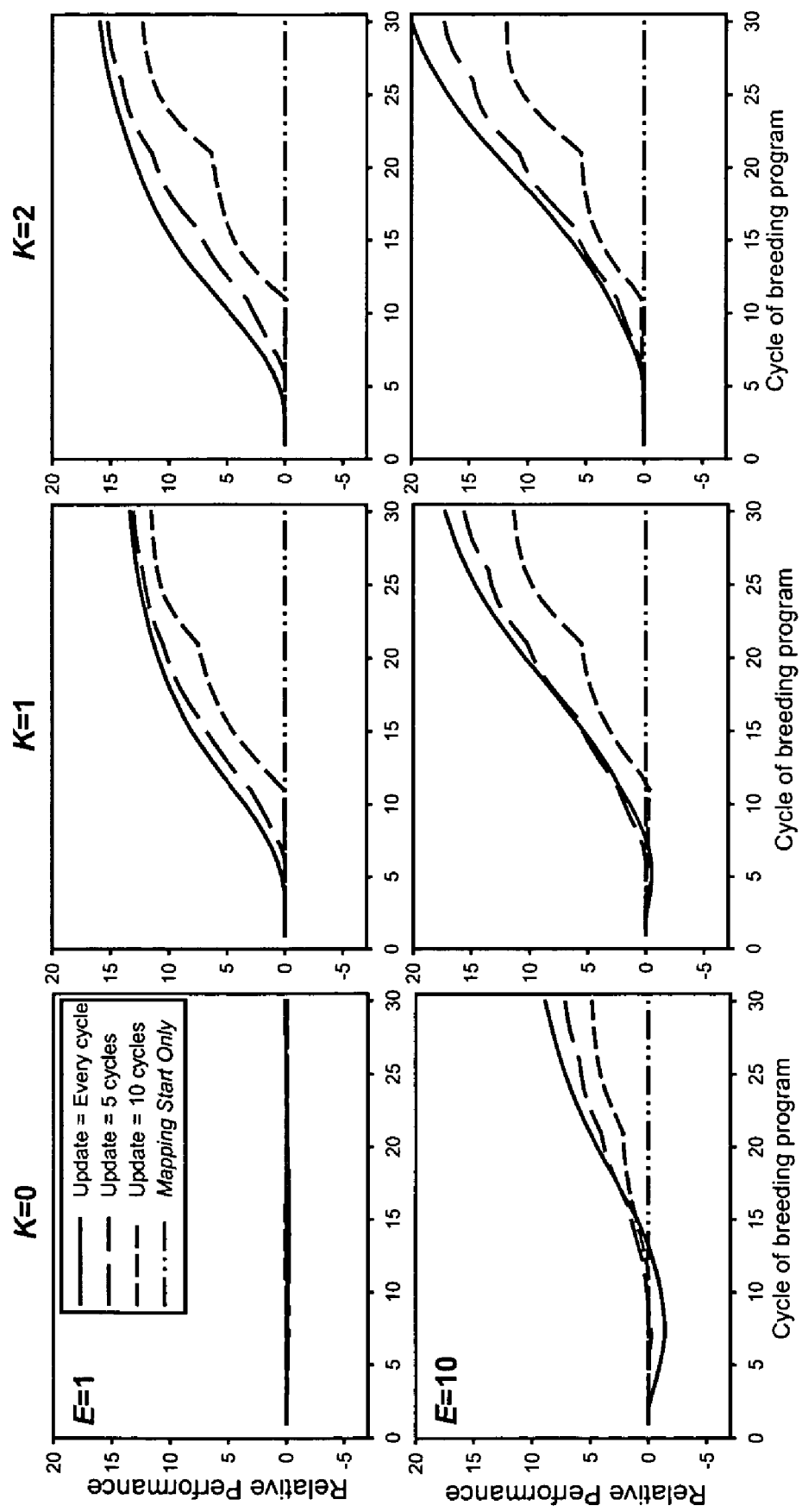
FIG. 21: The relative performance of the Mapping Start Only and Mapping As-You-Go methods for six general classes of genetic model. In all cases, performance is represented as the difference in response between a given breeding strategy and the Mapping Start Only method. The performance differences are expressed in terms of normalized trait value. Each line represents average performance across 1,000 runs of the breeding program (24,000 runs in total). A categorization of the E(NK) models considered is given in Table 1.

There was a substantial difference in the relative performances of the Mapping Start Only and Mapping As-You-Go methods among the six general classes of genetic model (FIG. 21). For the class of genetic model where only additive effects were present (i.e. E=1, K=0; top left panel of FIG. 21), there were relatively small differences in performance for the different MAS strategies. In contrast, for the classes of genetic models that contained epistasis but no gene-by-environment interaction (i.e. E=1; K=1,2; top middle and right panels of FIG. 21), the Mapping As-You-Go methods had higher levels of response than the Mapping Start Only method. The size of the advantage that was observed using the Mapping As-You-Go approach increased with K (i.e. more context dependency), or when the QTL effects were estimated more frequently. For the genetic model with gene-by-environment interaction effects but no epistasis (i.e. K=0; E=10; lower left panel of FIG. 21), the Mapping As-You-Go methods generally achieved higher levels of response compared to the Mapping Start Only method. When both epistasis and gene-by-environment interaction effects were present (i.e. K=1, 2; E=10; lower right two panels of FIG. 21), the Mapping As-You-Go method on average outperformed the Mapping Start Only method.

Example 6

Simulation of the Mapping-As-You-Go Strategy Using a Version of the HAPLO-MQM Approach for QTL Estimation The Mapping As-You-Go method was implemented using a version of the HAPLO-MQM method for QTL allele estimation (Jansen et al. 2003). In contrast to the previous examples, a genetic map was constructed. For this experiment, an 1800 cM genetic map with markers spaced every 5 cM was assumed. Effects were estimated for multiple-marker haplotype combinations, where a given haplotype was defined to span four adjacent marker locations. A high and low linkage disequilibrium situation was considered. A total of three general classes of genetic model were considered (Table 1; Example 4). One class of genetic model had gene-by-environment effects and no epistatic effects; i.e. K=0, E=10. The other two general classes of genetic model had a combination of gene-by-environment and epistatic effects; i.e. all combinations of E=10; K=1, 2. For each class of genetic model, a single level of N was considered (N=24). In all cases, the genetic effects for the QTL alleles were sampled at random from an underlying uniform distribution according to the description given in Cooper and Podlich (2002). For each general class of genetic model, a total of 100 different random parameterizations of the E(NK) model were considered. Scenarios were run using a heritability level of 0.1 on a single plant basis.

The implementation of the breeding program was the same as that described in Example 4. All breeding strategies were implemented with the following parameters: 30 cycles of selection, 200 individuals in each base population, 100 F1 bi-parental crosses, 5 Fn plants per F1, 10 testers per cross, doubled haploids used to get the Fn generation and 50% of the base population replaced each cycle. Each of the hybrid combinations was evaluated in a simulated multi-environment trial (MET) with ten locations. The phenotypic values of the hybrids across the ten locations were used to estimate the QTL allele effects.

For the Mapping Start Only approach, the QTL effects were estimated in cycle 1 of the breeding program and used throughout the 30 cycles of selection. For the Mapping As-You-Go approach, the QTL effects were re-estimated: (i) every cycle of the breeding program (i.e. Update=Every cycle), (ii) every 5 cycles of the breeding program (i.e. Update=5 cycles), and (iii) every 10 cycles of the breeding program (i.e. Update=10 cycles). In all cases, the older QTL estimates were completely replaced by the newer QTL estimates. Thus, no information was retained from one QTL mapping analysis to the next. Each of the MAS strategies was independently replicated 10 times for each parameterization of the E(NK) model. In total, the breeding program was run 24,000 times, encompassing 720,000 cycles of selection. The following parameter values were used.

| Engine parameters (Genetic model parameters): | | |
|---|---|---|
| Epistasis levels: | 3 levels; | K = 0, K = 1, K = 2 |
| GxE levels: | 1 levels; | E = 10 |
| Heritability levels: | 1 level; | H = 0.1 |
| E(NK) ensemble: | 100 parameterizations per model | |
| Total number of genetic models: 300 | | |

| MiniMin parameters (Breeding strategy parameters): | | |
|---|---|---|
| Update frequency: | 4 levels | Mapping Start Only; Mapping As-You-Go: Updated (cycles): 1, 5, 10 |
| Runs: | 10 times; | Reps per combination |
| Linkage Disequilibrium: | 2 levels | LD = High and LD |
| Total number of breeding strategy parameters: 8 | | |
| Total number of runs of MiniMin: 300 × 8 × 10 = 24,000 times | | |

Results

Figure 22:
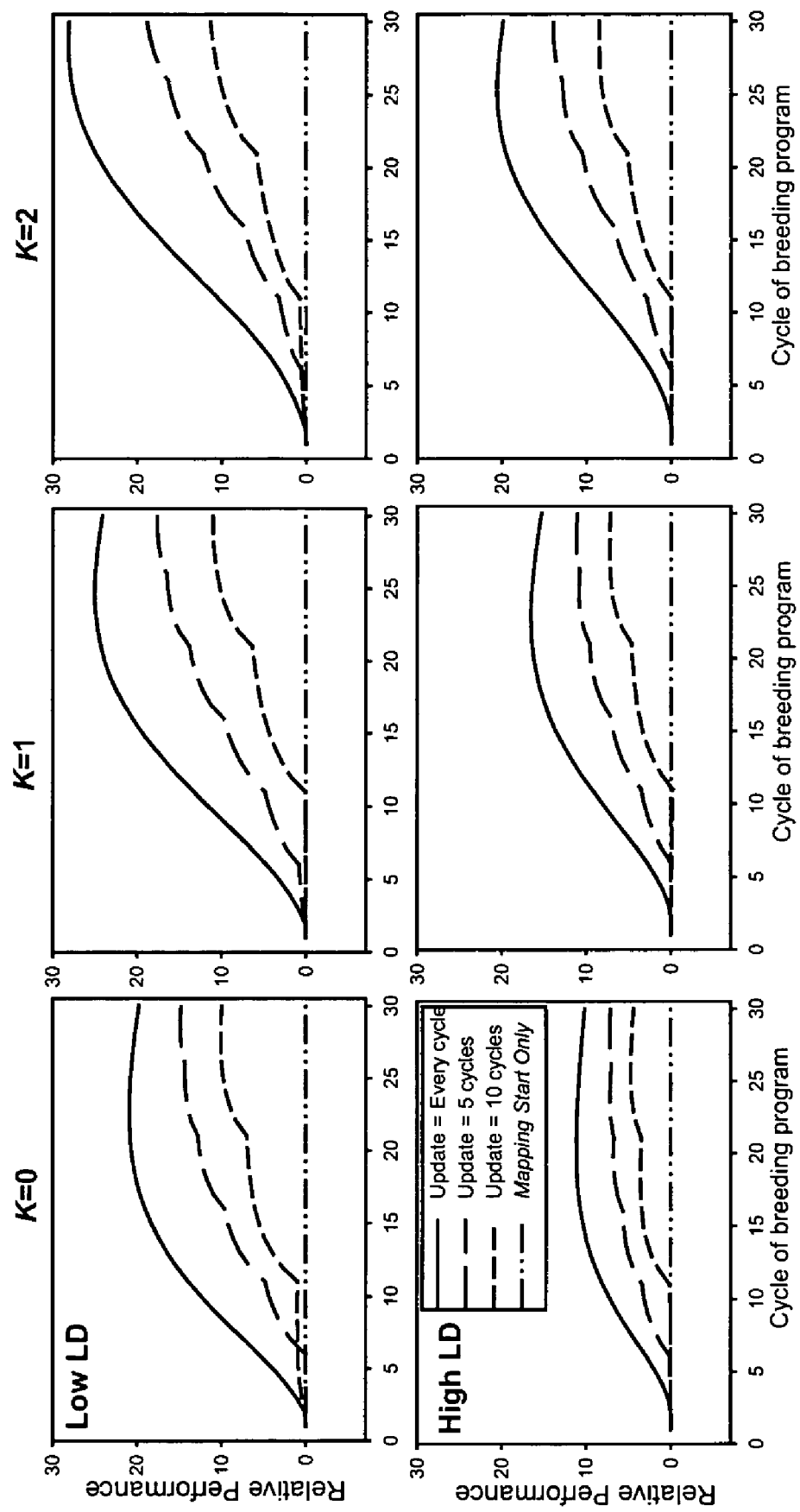
FIG. 22: The relative performance of the Mapping Start Only and Mapping As-You-Go methods for three general classes of genetic model (E=10; K=0,1,2) for two different starting population configurations (low and high linkage disequilibrium (LD) among markers). In all cases, performance is represented as the difference in response between a given breeding strategy and the Mapping Start Only method. The performance differences are expressed in terms of normalized trait value. Each line represents average performance across 1,000 runs of the breeding program (24,000 runs in total). A categorization of the E(NK) models considered is given in Table 1.

The results of the experiment were consistent with the results observed for the other implementations of the Mapping As-You-Go method. Namely, the Mapping As-You-Go method outperformed the Mapping Start Only when context dependencies were present, and the advantage displayed by the Mapping As-You-Go method increased as the frequency with which QTL estimates were updated was increased (FIG. 22). A greater difference in the performances of the Mapping As-You-Go and Mapping Start Only methods was observed when the starting population had low linkage disequilibrium compared to a situation where the starting population was constructed with high linkage disequilibrium.

Example 7

Comparison of the Performance of the Mapping as-You-Go Method to Phenotypic Selection In this simulation, the Mapping As-You-Go and Mapping Start Only methods were compared to phenotypic selection. In this experiment, a total of six general classes of genetic model were considered (Table 1; Example 4). The first general class of genetic model had only additive effects; i.e. E=1, K=0 (a classical finite locus additive model). Two of the general classes of genetic model had epistatic effects and no gene-by-environment interaction effects; i.e. E=1, K=1, 2. One class of genetic model had gene-by-environment effects and no epistatic effects; i.e. K=0, E=10. The remaining two general classes of genetic model had a combination of gene-by-environment and epistatic effects; i.e. all combinations of E=10; K=1, 2. For each class of genetic model, four levels of N were considered (N=12,24,48,96). In all cases, the genetic effects for the QTL alleles were sampled at random from an underlying uniform distribution according to the description given in Cooper and Podlich (2002). For each general class of genetic model, a total of 500 different random parameterizations of the E(NK) model were considered. Scenarios were run using a heritability level of 0.1 on a single plant basis.

The implementation of the breeding program was the same as that described in Example 4. All breeding strategies were implemented with the following parameters: 30 cycles of selection, 200 individuals in each base population, 100 F1 bi-parental crosses, 5 Fn plants per F1, 10 testers per cross, doubled haploids used to get the Fn generation and 50% of the base population replaced each cycle. Each of the hybrid combinations was evaluated in a simulated multi-environment trial (MET) with ten locations. The phenotypic values of the hybrids across the ten locations were used to estimate the QTL allele effects. For the phenotypic selection strategy, the average phenotypic performance of the hybrids across the ten locations was used to discriminate between the inbreds.

For the Mapping Start Only approach, the QTL effects were estimated in cycle 1 of the breeding program and used throughout the 30 cycles of selection. For the Mapping As-You-Go approach, the QTL effects were re-estimated: (i) every cycle of the breeding program (i.e. Update=Every cycle), (ii) every 5 cycles of the breeding program (i.e. Update=5 cycles), and (iii) every 10 cycles of the breeding program (i.e. Update=10 cycles). In all cases, the older QTL estimates were completely replaced by the newer QTL estimates. Thus, no information was retained from one QTL mapping analysis to the next. Each of the MAS strategies was independently replicated 10 times for each parameterization of the E(NK) model. In total, the breeding program was run 600,000 times, encompassing 18,000,000 cycles of selection. The following parameter values were used.

Engine parameters (Genetic model parameters):

| Epistasis levels: | 3 levels; | K = 0, K = 1, K = 2 |
| GxE levels: | 2 levels; | E = 1, 10 |

-continued

Engine parameters (Genetic model parameters):

| Gene no. levels: | 4 levels; | N = 12, 24, 48, 96 |
| Heritability levels: | 1 level; H = 0.1 | |
| E(NK) ensemble: | 500 parameterizations per model | |
| Total number of genetic models: 12000 | | |

MiniMin parameters (Breeding strategy parameters):

| Selection strategy: | 5 types | Mapping Start Only; |
| | | Mapping As-You-Go: Updated (cycles): |
| | | 1, 5, 10 |
| | | Phenotypic selection |
| Runs: | 10 times; | Reps per combination |
| Total number of breeding strategy parameters: 5 | | |
| Total number of runs of MiniMin: 12000 × 5 × 10 = 600,000 times | | |

Results

Figure 23:
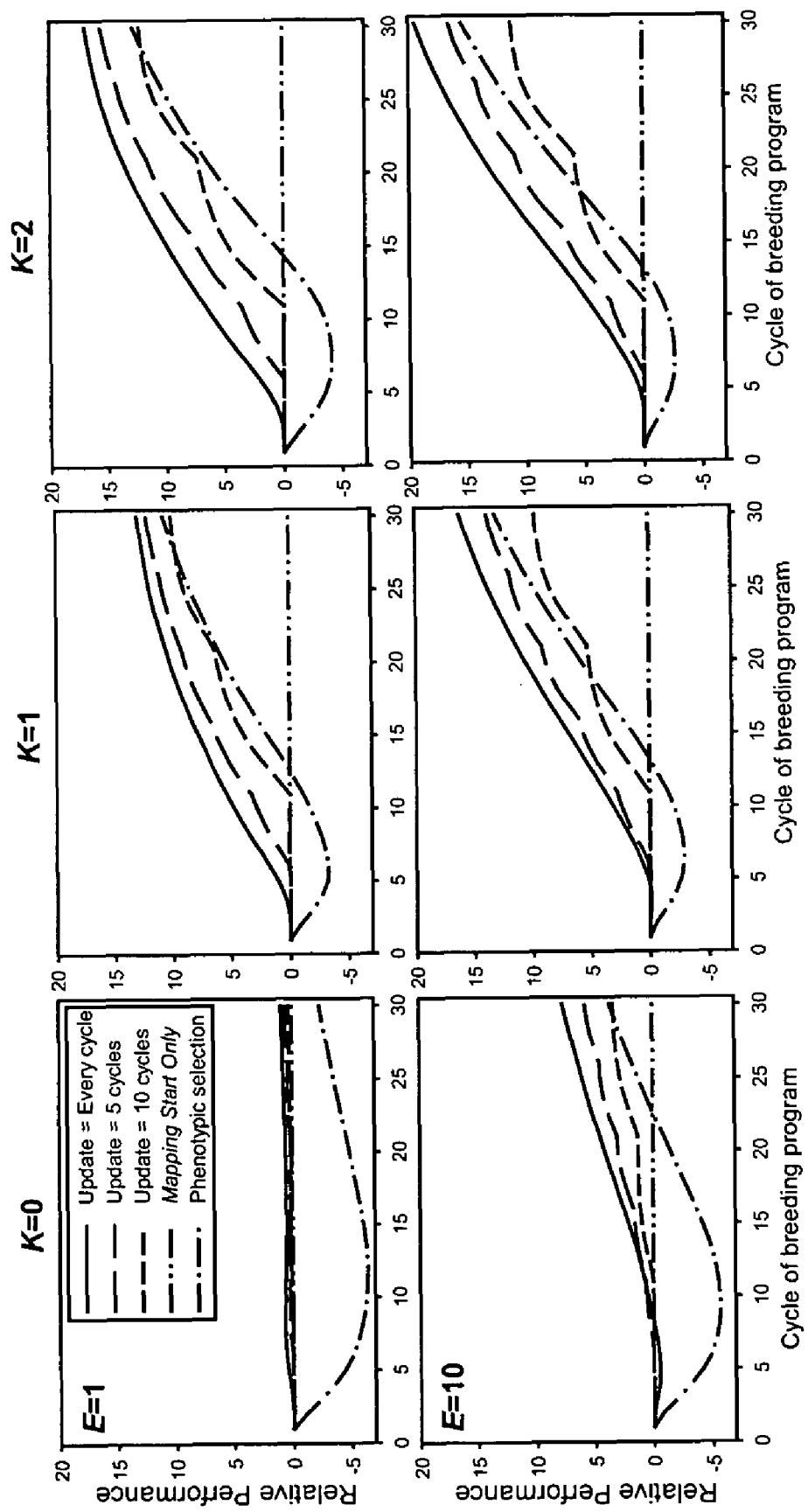
FIG. 23: The relative performance of five breeding strategies for six general classes of genetic model. In all cases, performance is represented as the difference in response between a given breeding strategy and the Mapping Start Only method. Positive values indicate the breeding strategy had a higher response than the Mapping Start Only method, and negative values indicate the breeding strategy had a lower response than the Mapping Start Only method. The performance differences are expressed in terms of normalized trait value. Each line represents average performance across 20,000 runs of the breeding program (600,000 runs in total). A categorization of the E(NK) models considered is given in Table 1.

For the models with no context dependencies (FIG. 23; top left panel) the two MAS strategies outperformed phenotypic selection for all of the cycles of selection considered here. However, when context dependencies were present (FIG. 23; all panels except top left), MAS outperformed phenotypic selection over the first 10 to 15 cycles. However, in the longer term, phenotypic selection outperformed Mapping Start Only, and in some cases, phenotypic selection outperformed versions of the Mapping As-You-Go method.

Example 8

Context Dependent Gene Effects

Figure 24:
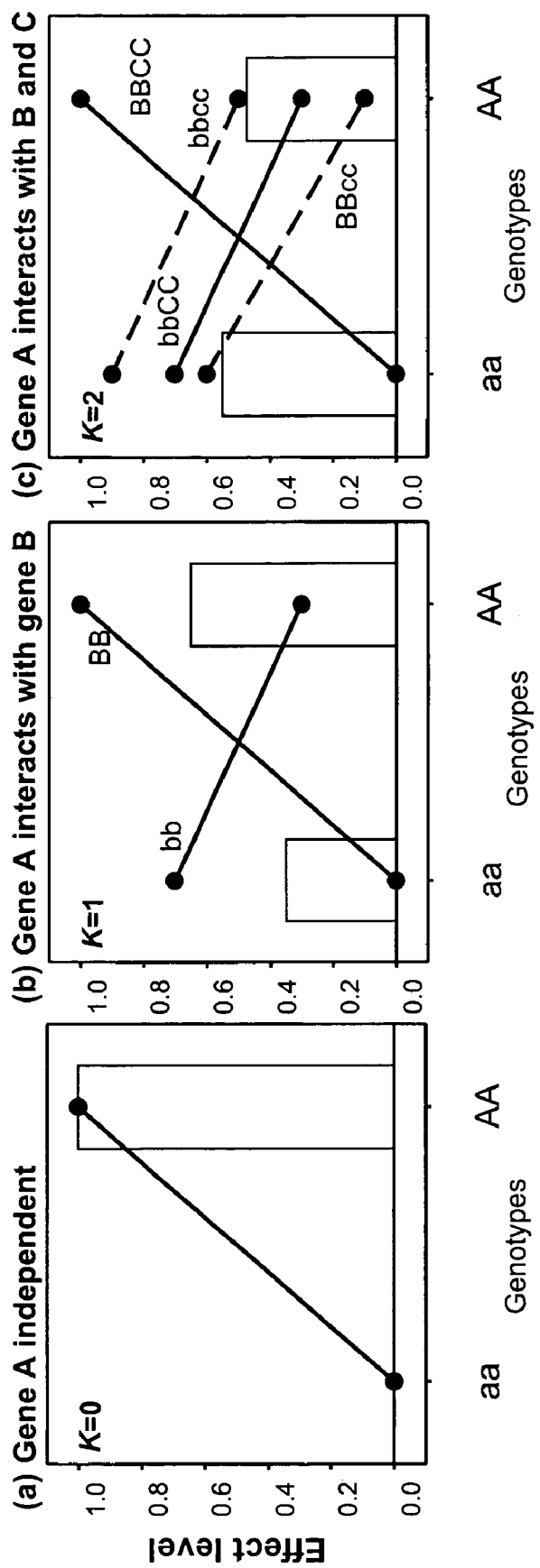
FIG. 24: Line plots representing the effect of genotype combinations referred to as "physiological epistasis," and bar graphs illustrating the average genotype effect of Gene A across the genetic background (vertical bars; statistical estimation of the average genotype value for the aa and AA genotypes of Gene A) Three hypothetical genetic models are illustrated in; (a) a single independent additive gene (Gene A); K=0, (b) a di-genic network where Gene A interacts with Gene B; K=1, and (c) a tri-genic network where Gene A interacts with Genes B and C; K=2, respectively. Values of the vertical bars show the effect of the two homozygous genotype classes for Gene A, averaged across all background genotype combinations in the network.

The presence of context dependency brings into question the value of a given QTL allele, the contrasts between the genotypes possessing different allele combinations, and the gene to phenotype relationship for traits. For example, in the case of epistasis, a QTL allele can have one effect in the presence of one genetic background and a different effect in the presence of another genetic background. In some cases, the presence of a given genetic background may change the definition of the favorable allele for the QTL. Epistasis can be characterized as physiological or as statistical epistasis. FIG. 24 illustrates features of both perspectives and emphasizes some of the complications that can arise with the existence of context dependencies due to epistasis. Here, three genetic models with different amounts of context dependency are considered: (i) gene A is independent of all other genes (FIG. 24a), (ii) gene A interacts with gene B (FIG. 24b), and (iii) gene A interacts with genes B and C (FIG. 24c).

There are many contrasts that can be used to study the influences of epistasis on the relative performance of multi-locus genotypes. Here we consider the contrast between the homozygous genotype classes at a single locus (i.e., taking a "gene's eye view" as described by Wade, (2002) supra). In the case where there is no context dependency (FIG. 24a), genotype AA always has the highest trait value, and hence there is a clear definition of the favorable homozygous class. However, in cases where Gene A interacts with other genes (i.e., FIGS. 24b,c), the value of the genotype classes and the definition of the favorable genotype class are less well defined. For example, in FIG. 24b the highest performing combination for Gene A is genotype AA when combination BB is present at Gene B, and genotype aa is the highest performing genotype when combination bb is present at Gene B. Genotype class AA has the highest effect when averaged across all combinations of Gene B (FIG. 24b; vertical bars). In FIG. 24c, the genotype combination AABBCC has the highest performance (line plot) but genotype aa has the highest value when averaged across all background genotypes for genes B and C (vertical bars).

Figure 25:
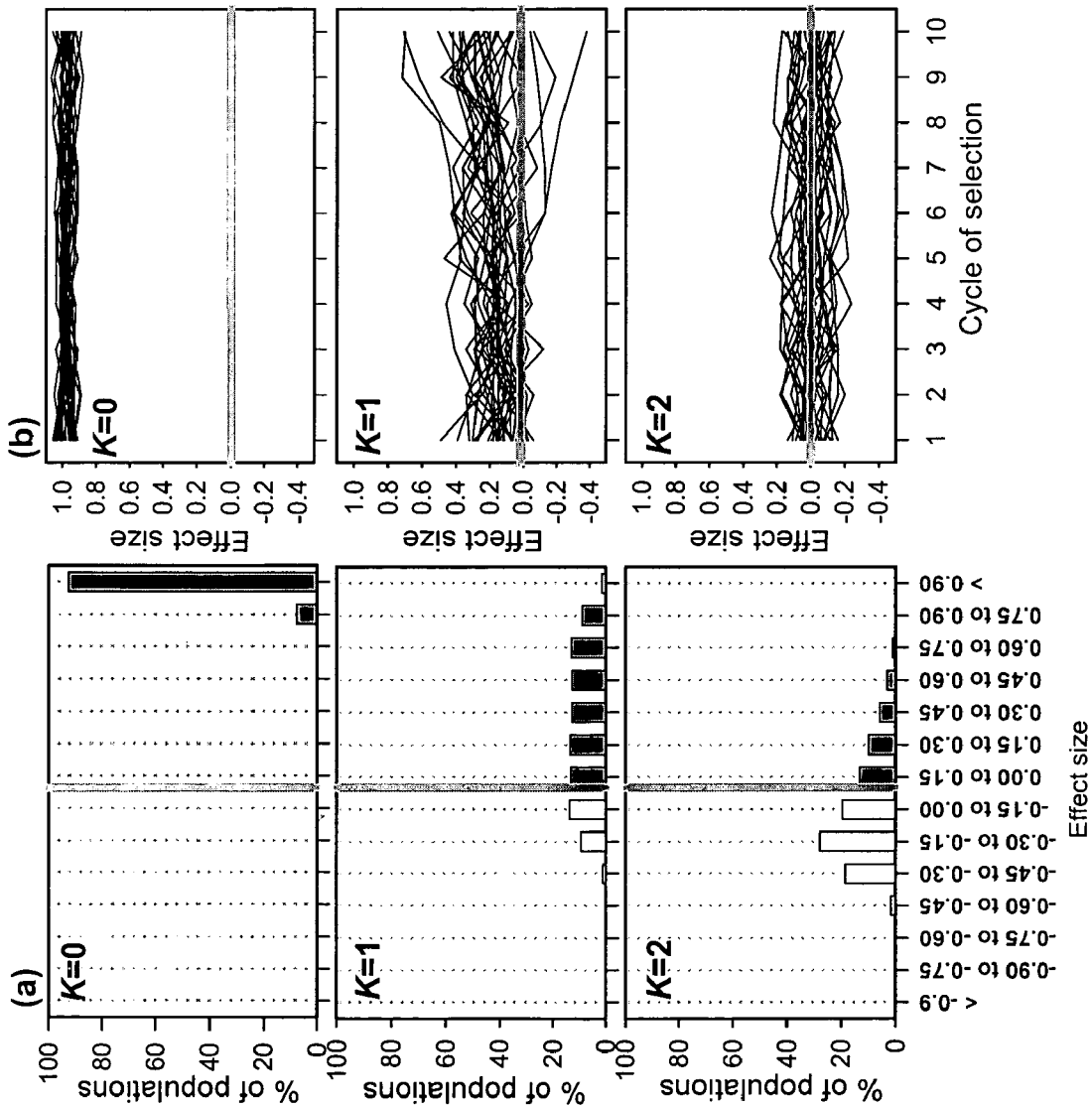
FIG. 25*a*: A series of bar graphs showing the distribution of allele effect size for Gene A estimated in 10,000 independent populations.
FIG. 25*b* shows the estimated allele effect for Gene A across 10 cycles of selection for thirty different runs of selection. A positive effect size indicates that genotype class AA was favorable and a negative effect size indicates that genotype class aa was favorable. The three genetic models used in the construction of this figure are an extension of those presented in Figure 24. In all cases, the genetic models had 10 genes. Genes not represented in FIG. 24 were defined as having additive effects (i.e. equivalent to FIG. 24a). For example, for genetic model (K=2), the first three genes were defined as in FIG. 24c and the remaining 7 genes were defined to have additive independent effects.

Within a population of individuals, the background effects are not represented equally since allele and genotype frequencies are not the same, or even in Hardy-Weinberg equilibrium. Furthermore, the frequency of alleles and genotype combinations can differ from one population to the next and from one generation to the next. When context dependencies due to epistasis are present, each population samples a different set and frequency of background effects resulting in distinct trait phenotypes and hence QTL allele effects will differ among populations. Therefore, the effect of a QTL allele or genotype combination is population specific and thus any estimate of QTL effect is in context with a given population of individuals in a given environment. To illustrate this property, 10,000 independent populations were created for each of the three genetic models considered in FIG. 24. A random set of allele frequencies were independently defined for each population. FIG. 25a shows the distribution of the estimated QTL effect size for Gene A, where the QTL effect was represented as the difference in value for the homozygous genotype classes for Gene A (i.e. average effect of AA minus the average effect of aa). A positive effect size indicates that genotype class AA was favorable and a negative effect size indicates that genotype class aa was favorable. For the genetic model where there were no context dependencies (FIG. 25a), the estimated effect of Gene A was relatively consistent across the 10,000 populations (FIG. 25a; K=0). In contrast, the genetic models that contained context dependencies (FIGS. 24b,c) had highly variable estimates for Gene A (FIGS. 25a; K=1 and K=2). In these two scenarios, both the magnitude of the effects and the definition of the favorable genotype class varied among the populations. These results illustrate how the definition of the highest value genotype and estimated effect of an allele can differ among random sets of genetic background.

The genetic backgrounds of germplasm generated over cycles of selection are not random. Thus, the variation shown in FIG. 25a is not necessarily representative of the variation that may be expected from germplasm generated over consecutive cycles of a breeding program. Instead, the change in frequencies of alleles in a population is likely to be more systematic. This is due to the coancestral or pedigree relationships that exist among individuals generated over cycles of the breeding program. FIG. 25b demonstrates this property for each genetic model shown in FIG. 24. Here, the effect of Gene A is estimated over 10 cycles of selection, where each estimate is independent and is based on the germplasm available in the current cycle of selection. Each line represents an independent run of selection. As was the case in FIG. 25a, there was variation among the estimates of QTL effects for the genetic models with context dependencies (FIGS. 25b; K=1 and K=2). In this case, the differences were less variable among consecutive cycles of selection than they were among the 10,000 random populations (FIG. 25a cf. FIG. 25b for K=1 and K=2). However, it is also important to emphasize that there were some differences among the cycles of selection. The figures show a deviation in the magnitude of QTL effects as well as intermittent change in the definition of the favorable genotype class from cycle to cycle. These results emphasize the presence of a QTL effect that is dependent on the evolving population structure at any point in the sequence of breeding cycles.

While the foregoing invention has been described in some detail for purposes of clarity and understanding, it will be clear to one skilled in the art from a reading of this disclosure that various changes in form and detail can be made without departing from the true scope of the invention. For example, alternative genetic markers can readily be applied in the methods of the invention. Additionally, both single gene and quantitative trait loci are suitable for mapping according to the methods of the invention. All publications, patents, patent applications, or other documents cited in this application are incorporated by reference in their entirety for all purposes to the same extent as if each individual publication, patent, patent application, or other document were individually indicated to be incorporated by reference for all purposes.

What is claimed is:

1. A method for ensuring the validity of a correspondence between at least one marker and at least one phenotype, the method comprising: providing a recursively determined estimate of correlation between at least one marker and at least one phenotype across a plurality of plant populations, which plant populations collectively comprise progeny of a plurality of biparental crosses, wherein the recursively determined estimate of correlation is provided by:
    a) providing a first estimate of QTL allele effects demonstrating a correlation between an allele of the at least one marker and the at least one phenotype in a plurality of plants;
    b) selecting at least one plant, which at least one plant is optionally selected from the plurality of plants of step a), with the allele of the at least one QTL marker;
    c) crossing the selected plant to generate a population of progeny;
    d) estimating a correlation between an allele of the same or different at least one marker and the at least one phenotype in the population of progeny of step c), thereby generating a second estimate of QTL allele effects;
    e) updating the first estimate of QTL allele effects to generate a first updated estimate of QTL allele effects, thereby ensuring the correspondence between the at least one marker and the phenotype;
    f) selecting at least one member of the population of progeny a desired allele of at least one marker validated according to the updated estimate of QTL allele effects; and,
    g) optionally repeating steps c) through f) one or more times to generate at least one subsequent population of progeny.

2. The method of claim 1, further comprising crossing the at least one selected plant.

3. The method of claim 2, comprising self-crossing, backcrossing, or outcrossing the at least one selected plant.

4. A method for ensuring the validity of a correspondence between at least one marker and at least one phenotype, the method comprising: providing a recursively determined estimate of correlation between at least one marker and at least one phenotype across a plurality of plant populations, which plant populations collectively comprise progeny of a plurality of biparental crosses, further comprising cloning a nucleic acid fragment in linkage disequilibrium with the at least one marker; and transducing the nucleic acid fragment into a plant.

5. The method of claim 4, comprising transducing the nucleic acid fragment into a plant in an expression cassette comprising a promoter operably linked to the nucleic acid fragment.

6. The method of claim 5, wherein the plant is sexually crossed with a second plant.

\* \* \* \* \*